US011130964B2

(12) United States Patent
Bean et al.

(10) Patent No.: US 11,130,964 B2
(45) Date of Patent: Sep. 28, 2021

(54) INSECT INHIBITORY PROTEINS

(71) Applicant: Monsanto Technology LLC, St. Louis, MO (US)

(72) Inventors: Gregory J. Bean, St. Louis, MO (US); David J. Bowen, Wildwood, MO (US); Catherine A. Chay, Ballwin, MO (US); Arlene R. Howe, Clarkson Valley, MO (US); Jason S. Milligan, Troy, IL (US); Yong Yin, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 7 days.

(21) Appl. No.: 16/205,426

(22) Filed: Nov. 30, 2018

(65) Prior Publication Data

US 2019/0153468 A1 May 23, 2019

Related U.S. Application Data

(63) Continuation-in-part of application No. 14/945,140, filed on Nov. 18, 2015, now Pat. No. 10,662,439.

(60) Provisional application No. 62/082,504, filed on Nov. 20, 2014.

(51) Int. Cl.
*C12N 15/82* (2006.01)
*C07K 14/195* (2006.01)
*A01N 63/50* (2020.01)

(52) U.S. Cl.
CPC ......... *C12N 15/8286* (2013.01); *A01N 63/50* (2020.01); *C07K 14/195* (2013.01)

(58) Field of Classification Search
CPC .......................... C12N 15/8286; C07K 14/195
See application file for complete search history.

(56) References Cited

U.S. PATENT DOCUMENTS 5,880,275 A 3/1999 Fischhoff et al.
6,033,874 A 3/2000 Baum et al.
6,501,009 B1 12/2002 Romano
6,713,063 B1 3/2004 Malvar et al.
6,962,705 B2 11/2005 Malvar et al.
7,064,249 B2 6/2006 Corbin et al.
7,070,982 B2 7/2006 Malvar et al.
7,510,878 B2 3/2009 Abad et al.
7,772,465 B2 8/2010 Abad et al.
7,812,129 B1 10/2010 Abad et al.
8,461,415 B2 6/2013 Sampson et al.
8,586,027 B2 11/2013 Escobar et al.
8,609,936 B2 12/2013 Baum et al.
2002/0199215 A1 12/2002 Boets et al.
2006/0112447 A1 5/2006 Bogdanova et al.
2008/0172762 A1 7/2008 Cerf et al.
2009/0313721 A1 12/2009 Abad et al.
2010/0017914 A1 1/2010 Kruse
2010/0077507 A1 3/2010 Abad et al.
2010/0077508 A1 3/2010 Abad et al.
2010/0192256 A1 7/2010 Abad et al.
2010/0269221 A1 10/2010 Abad et al.
2011/0030096 A1* 2/2011 Sampson ........... C12N 15/8286 800/279
2011/0030093 A1 3/2011 Dhugga
2011/0055968 A1 3/2011 Cerf et al.
2011/0112013 A1 5/2011 Abad et al.
2011/0154536 A1 6/2011 Abad et al.
2011/0191900 A1 8/2011 Song et al.
2012/0047606 A1 2/2012 Abad et al.
2012/0117690 A1 5/2012 Cerf et al.
2012/0167259 A1 6/2012 Liu et al.
2012/0192310 A1 7/2012 Abad et al.
2012/0233726 A1 9/2012 Abad et al.
(Continued)

FOREIGN PATENT DOCUMENTS

CL 1395-2009 6/2009
EP 2079314 B1 3/2010
(Continued)

OTHER PUBLICATIONS

Ruiu, Insects (2013) 4:476-492.*
De Oliveira et al (2004) 70:6657-6654.*
Arholo-Filho et al, Insects (2014) 5:62-91.*
UniProt Accession No. H0UDD3, integrated into UniProt on Feb. 22, 2012.*
UniProt Accession No. A0A075R7H4, integrated into UniProt on Oct. 29, 2014.*
UniProt Accession A0A177XJY5, integrated into the database on Sep. 7, 2016.*
Yin, Y., "Novel MTX2-like Proteins for Insect Control", presentation at the 47th Annual Meeting of the Society for Invertebrate Pathology, Mainz, Germany, Aug. 2014 [PowerPoint presentation]. 14 slides.
(Continued)

*Primary Examiner* — Mykola V. Kovalenko
(74) *Attorney, Agent, or Firm* — Dentons US LLP; Timothy K. Ball

(57) ABSTRACT

Insecticidal proteins exhibiting toxic activity against Coleopteran and Lepidopteran pest species are disclosed, and include, but are not limited to, TIC3668, TIC3669, TIC3670, TIC4076, TIC4078, TIC4260, TIC4346, TIC4826, TIC4861, TIC4862, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, TIC7535 and TIC-3668-type proteins. DNA molecules and constructs are provided which contain a polynucleotide sequence encoding one or more of the disclosed TIC3668-type proteins. Transgenic plants, plant cells, seed, and plant parts resistant to Lepidopteran and Coleopteran infestation are provided which contain polynucleotide sequences encoding the insecticidal proteins of the present invention. Methods for detecting the presence of the polynucleotides or the proteins of the present invention in a biological sample, and methods of controlling Coleopteran and Lepidopteran species pests using any of the TIC3668-type insecticidal proteins are also provided.

19 Claims, 3 Drawing Sheets

Specification includes a Sequence Listing.

(56) References Cited

U.S. PATENT DOCUMENTS

| | | | |
|---|---|---|---|
| 2013/0097735 | A1 | 4/2013 | Bowen et al. |
| 2013/0269060 | A1 | 10/2013 | Baum et al. |
| 2014/0007292 | A1 | 1/2014 | Cerf et al. |
| 2014/0033361 | A1 | 1/2014 | Altier et al. |
| 2020/0157561 | A1 | 5/2020 | Bean et al. |
| 2020/0157562 | A1 | 5/2020 | Bean et al. |

FOREIGN PATENT DOCUMENTS

| | | | |
|---|---|---|---|
| EP | 2455392 | A2 | 5/2012 |
| EP | 2671951 | A2 | 12/2013 |
| RU | 251286 | C2 | 4/2014 |
| UA | 98770 | C2 | 6/2012 |
| WO | WO 2010/099365 | | 9/2010 |
| WO | WO 2010/142055 | | 12/2010 |
| WO | WO 2011/014749 | | 2/2011 |
| WO | WO 2014/008054 | | 1/2014 |
| WO | WO 2014/045131 | | 3/2014 |

OTHER PUBLICATIONS

Crickmore, N., et al., "Revision of the nomenclature for the Bacillus thuringiensis pesticidal crystal proteins." *Microbiol Mol Biol Rev.* 1998;62(3):807-13.

Palma, L., et al., "Bacillus thuringiensis toxins: an overview of their biocidal activity," *Toxins* (Basel). Dec. 11, 2014;6(12):3296-325.

Moar, W., et al., "The structure/function of new insecticidal proteins and regulatory challenges for commercialization". *Journal of Invertebrate Pathology*, 2017, 142:1-4.

Maagd, R., "Structure, diversity, and evolution of protein toxins from spore-forming entomopathogenic bacteria," *Annu Rev Genet.* 2003;37:409-33.

Ruiu, L., "Emerging entomopathogenic bacteria for insect pest management," *Bulletin of Insectology* 66 (2): 181-186, 2013.

Bacillus thuringiensis Toxin Nomenclature, Full list of delta-endotoxins. Retrieved from http://www.lifesci.sussex.ac.uk/home/Neil_Crickmore/Bt/toxins2.html on Nov. 28, 2018.

International Search Report and Written Opinion regarding International Application No. PCT/US2015/061371, dated Mar. 9, 2016.

Ruiu, "*Brevibacillus laterosporus*, a Pathogen of Invertebrates and a Broad-Spectrum Antimicrobial Species," *Insects* 4:476-492, 2013.

Office Action regarding Chilean Application No. 1298-2017, dated Jun. 19, 2018.

USPTO: Non-Final Office Action regarding U.S. Appl. No. 14/945,140, dated Feb. 25, 2019.

Campbell et al., "Codon Usage in Higher Plants, Green Algae, and Cyanobacteria," *Plant Physiol.* 92:1-11, 1990.

De Oliveira et al., "Molecular Characterization of *Brevibacillus laterosporus* and Its Potential Use in Biological Control," *Applied and Environmental Microbiology* 70:6657-6654, 2004.

Declaration of David J. Bowen under 37 C.F.R § 1.132, dated Nov. 30, 2018.

Response to Non-Final Office Action regarding U.S. Appl. No. 16/205,426, dated Jun. 21, 2019.

USPTO: Notice of Allowance regarding U.S. Appl. No. 14/945,140 dated Mar. 10, 2020.

U.S. Appl. No. 16/684,007, filed Nov. 14, 2019, Bean et al.

U.S. Appl. No. 16/684,029, filed Nov. 14, 2019, Bean et al.

GenBank Accession No. WP_003343676, Jul. 21, 2013.

Sharma et al., "Genome Sequence of *Brevibacillus latersporis* Strain GI-9", Journal of Bacteriology, p. 1279, 2012.

Thanabalu et al., "A *Bacillus sphaericus* gene encoding a novel type of mosquitocidal toxin of 31.8 kDa", Institute of Molecular and Cell Biology, National University of Singapore, pp. 85-89, 1996.

Petit et al., "*Clostridium perfringens* Epsilon Toxin Induces a Rapid Change of Cell Membrane Permeability to Ions and Forms Channels in Artificial Lipid Bilayers*", The Journal of Biological Chemistry, 276(19):15736-15740, 2001.

GenPept Accession No. WP_003335736, Jan. 13, 2020.

GenPept Accession No. WP_022584503, Jan. 13, 2020.

USPTO Response to Non-Final Office Action regarding U.S. Appl. No. 16/684,007, filed Jun. 16, 2021.

USPTO: Response to Non-Final Office Action regarding U.S. Appl. No. 16/684,029, filed Jul. 1, 2021.

USPTO: Non-Final Office Action regarding U.S. Appl. No. 16/684,007, dated Mar. 16, 2021.

USPTO: Non-Final Office Action regarding U.S. Appl. No. 16/684,029, dated Apr. 1, 2021.

USPTO: Notice of Allowance regarding U.S. Appl. No. 16/684,029, dated Jul. 26, 2021.

USPTO: Notice of Allowance regarding U.S. Appl. No. 16/684,007, dated Aug. 9, 2021.

* cited by examiner

```
SEQ ID NO:  Toxin Protein
                                                24
 2  TIC3668   mkkfaslilt svflfsstqf vhaSSTDVQE RLRDLAREDE AGTENEAWNT NFKPSDEQQF SYSPTEGIVF LTPPKNVIGE   80
 4  TIC3669   mkkfaslili svflfsstqf vhaSSTDVQE RLRDLAREDE AGTENEAWNT NFKPSDEQQF SYSPTEGIVF LTPPKNVIGE   80
 6  TIC3670   mkkfaslilt svflfsstqf vhaSSTDVQE RLRDLAREDE AGTENEAWNT NFKPSDEQQF SYSPTEGIVF LTPPKNVIGE   80
 8  TIC4076   mkkfaslili svflfsstqf vhaSSTDVQE RLRDLARENE AGTLNEAWNT NFKPSDEQQF SYSPTEGIVF LTPPKNVIGE   80
10  TIC4078   mkkfaslilt svflfsstqf vhaSSTDVQE RLRDLARENE AGTLNVAWNT NFKPSDEQQF SYSPTEGFIF LTPPKNVIGE   80
12  TIC4260   mkkfaslilt svflfsstqf vhaSSIDVQE RLRDLAREDE AGTENVAWNT NFKPSDEQQF SYSPTEGFIF LTPPKNVIGE   80

 2  TIC3668   RRISQYKVNN AWATLVGSPT EASGTPLYAG KNVLDNSKGT MDQELLTPEF NYTYTESTSN TITHGLKLGV KTTATMKFPI  160
 4  TIC3669   RRISQYKVNN AWATLEGSPT EVSGTPLYAG KNVLDNSKGT IDQELLTPEF SYTYTESTSN TTTHGLKVGV KTTATMKFPI  160
 6  TIC3670   RRISQYKVNN AWATLEGSPT EASGTPLYAG KNVLDNSKGT MDQELLTPEF NYTYTESTSN TTTHGLKLGV KTTATMKFPI  160
 8  TIC4076   RRISQYKVNN AWATLEGSPT EMSGTPLYAG KNVLDNSKGT SDQELLTPEF TYTYTESTSN TTTHGLKLGV KTTATMKFPI  160
10  TIC4078   RRISHYKVNN AWATLEGSPT EVSGTPLYAG RNVLDNSKGT IDQEMLTPEF NYTYTEGTSN TTTHGLKLGV KTTATMKFPI  160
12  TIC4260   RRISHYKVNN AWATLVGSPT EASGTPLYAG RNVLDNSKGT MDQEMLTPEF SYTYTEGTSN TITHGLKVGV KTTATMKFPI  160

 2  TIC3668   AQGSMEASTE YNFQNSSTDT KTKQVSYKSP SQKIKVPAGK TYRVLAYLNT GSISGEANLY ANVGGIAWRV SPGYPNGGGV  240
 4  TIC3669   AQGSMEASTE YNFQNSSTDT KTKQVSYKSP SQKIKVPAGK TYRVLAYLNT GSISGEANLY ANVGGIAWRV SPGYPNGGGV  240
 6  TIC3670   AQGSMEASTE YNFQNSSTDT KTKQVSYKSP SQKIKVPAGK TYRVLAYLNT GSISGEANLY ANVGGIAWRV SPGYPNGGGV  240
 8  TIC4076   AQGSMEASTE YNFQNSSTDT KTKQVSYKSP SQKIKVPAGK TFRVLAYLNT GSISGEANLY ANVGGIAWGV LPGYPNGGGV  240
10  TIC4078   AQGSMEASTE YNFQNSSTDT KTKQVSYKSP SQKIKVPAGK TFRVLAYLNT GSISGEANLY ANVGGVAWGV LPGYPNGGGV  240
12  TIC4260   AQGSMEASTE YNFQNSSTDT KTKQVSYKSP SQKIKVPAGK TYRVLAYLNT GSISGEANLY ANVGGVAWKV SPGYPNGGGV  240

 2  TIC3668   NIGAVLTKCQ QKGWGDFRNF QPSGRDVIVK GQGTFKSNYG TDFILKIEDI TDSKLRNNNG SGTVVQEIKV PLIRTEI     317
 4  TIC3669   NIGAVLTKCQ QKGWGDFRNF QPSGRDVIVK GQGTFKSNYG TDFILKIEDI TDSKLRNNNG SGTVVQEIKV PLIRTEI     317
 6  TIC3670   NIGAVLTKCQ QKGWGDFRNF QPSGRDVIVK GQGTFKSNYG TDFILKIEDI TDSKLRNNNG SGTVVQEIKV PLIRTEI     317
 8  TIC4076   NIGAVLTKCQ QKGWGDFRNF QPSGRDVIVK GQGTFTSNYG TDFILKIEDI TDSKLRNNNG SGTVVQEIKV PLIRTEI     317
10  TIC4078   NIGAVLTKCQ QKGWGDFRNF QPSGRDVIVK GQGTFTSNYG TDFILKIEDI TDSKLRNNNG SGTVVQEIKV PLIRTEI     317
12  TIC4260   NIGAVLTKCQ QKGWGDFRNF QPSGRDVIVK GQGTFTSNYG TDFILKIEDI TDSKLRNNNG SGTVVQEIKV PLIRTEI     317
```

FIGURE 1

SEQUENCE LISTING

```
<160> NUMBER OF SEQ ID NOS: 132

<210> SEQ ID NO 1
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained
      from a Brevibacillus laterosporus species encoding a TIC3668
      protein from an open reading frame at nucleotide position 1-951
      and a translation termination codon.

<400> SEQUENCE: 1

atgaaaaaat ttgcaagttt aattcttaca agtgtgttcc ttttttcgag tacgcaattt     60

gttcatgcgt catccacaga tgttcaagaa agattacggg acttggcaag agaagatgaa    120

gctggaacct ttaatgaagc atggaatact aacttcaaac ccagtgatga acaacaattc    180

tcgtatagtc caactgaagg aattgttttc ttaacaccac ctaaaaatgt tattggcgaa    240

agaagaattt cacagtataa agtaaataat gcatgggcta cattagtagg aagtccaacc    300

gaagcatcgg ggacaccttt atatgcggga aaaaacgtat tagataactc aaaaggaaca    360

atggatcaag agctgttaac acccgagttt aactatacct atacggaaag cacttcaaat    420

acaataactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg gggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954


<210> SEQ ID NO 2
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: the amino acid sequence translation of the
      TIC3668 precursor protein from the open reading frame as set forth
      in SEQ ID NO:1.

<400> SEQUENCE: 2

Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30
```

-continued

```
Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Val
                85                  90                  95

Gly Ser Pro Thr Glu Ala Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Ile Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 3
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC3669 protein from an open reading frame at nucleotide position 1-951 and a translation termination codon.

<400> SEQUENCE: 3

```
atgaaaaaat ttgcaagttt aattcttata agtgtgttcc ttttttcgag tacgcaattt     60

gttcatgcgt catccacaga tgttcaagaa agattacggg acttggcaag agaagatgaa    120

gctggaacct ttaatgaagc atggaatact aacttcaaac ccagtgatga acaacaattc    180

tcgtatagtc caactgaagg aattgttttc ttaacaccac ctaaaaatgt tattggcgaa    240

agaagaattt cacagtataa agtaaataat gcatgggcta cattagaagg aagtccaacc    300
```

```
gaagtatcgg ggacaccttt atatgcggga aaaaacgtat tagataactc aaaaggaaca    360

atcgatcaag agctgttaac acccgagttt agttatacct atacggaaag cacttcaaat    420

acaacaactc atggattaaa agtaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 4
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
TIC3669 precursor protein from the open reading frame as set forth
in SEQ ID NO:3.

<400> SEQUENCE: 4

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Ile Asp Gln Glu Leu Leu Thr Pro
        115                 120                 125

Glu Phe Ser Tyr Thr Tyr Thr Glu Ser Thr Ser Asn Thr Thr Thr His
    130                 135                 140

Gly Leu Lys Val Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
```

```
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 5
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC3670 protein from an open reading frame at nucleotide position 1-951 and a translation termination codon.

<400> SEQUENCE: 5

```
atgaaaaaat ttgcaagttt aattcttaca agtgtgttcc ttttttcgag tacgcaattt     60

gttcatgcgt catccacaga tgttcaagaa agattacggg acttggcaag agaagatgaa    120

gctggaacct ttaatgaagc atggaatact aacttcaaac ccagtgatga acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagcatcgg ggacaccttt atatgcggga aaaaacgtat tagataactc aaaaggaaca    360

atggatcaag agctgttaac acccgagttt aactatacct atacggaaag cacttcaaat    420

acaacaaccc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg gggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 6
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC3670 precursor protein from the open reading frame as set forth in SEQ ID NO:5.

<400> SEQUENCE: 6

```
Met Lys Lys Phe Ala Ser Leu Ile Leu Thr Ser Val Phe Leu Phe Ser
```

-continued

```
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Ala Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 7
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4076 protein from an open reading frame at nucleotide position 1-951 and a translation termination codon.

<400> SEQUENCE: 7

```
atgaaaaaat ttgcaagttt aattcttata agtgtgttcc ttttttcgag tacgcaattt     60

gttcatgcgt catccacaga tgttcaagaa agattacggg acttggcaag agaaaatgaa    120

gctggaaccc ttaatgaagc atggaatact aacttcaaac ccagtgatga acaacaattc    180
```

-continued

```
tcttatagtc caactgaagg tattgttttc ttaacaccac ctaaaaatgt tattggcgaa    240

agaagaattt cacagtataa agtaaataat gcatgggcta cattagaagg aagtccaacc    300

gaaatgtcgg ggacaccttt atatgcggga aaaaacgtat tagataactc aaaaggaaca    360

agcgatcaag agctgttaac acccgagttt acctatacct atacggaaag cacttcaaat    420

acaacaactc atggattaaa attaggagtc aaaaccactg ctaccatgaa attccccgatt   480

gctcagggta gcatggaagc ttctactgaa tataactttc aaaattcttc cactgatact    540

aaaactaaac aagtatcata taaaagccca tcacaaaaga ttaaagtacc agcaggtaaa    600

acctttagag ttttagcata cctaaatact ggatctattt caggtgaagc taacctttac    660

gcaaatgttg ggggtatagc ttggggggtt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcacatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 8
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC4076 precursor protein from the open reading frame as set forth
      in SEQ ID NO:7.

<400> SEQUENCE: 8

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Met Ser Gly Thr Pro Leu Tyr Ala Gly Lys Asn
            100                 105                 110

Val Leu Asp Asn Ser Lys Gly Thr Ser Asp Gln Glu Leu Leu Thr Pro
        115                 120                 125

Glu Phe Thr Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205
```

```
Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Thr Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315


<210> SEQ ID NO 9
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained
      from a Brevibacillus laterosporus species encoding a TIC4078
      protein from an open reading frame at nucleotide position 1-951
      and a translation termination codon.

<400> SEQUENCE: 9

atgaaaaaat ttgcaagttt aattcttaca agtgtgttcc ttttttcgag tacacaattt     60

gttcatgcgt catccacaga tgttcaagaa agattacggg acttggcaag agaaaatgaa    120

gctggaaccc ttaatgtagc atggaatact aacttcaaac ccagtgatga acaacaattc    180

tcttatagtc caactgaagg ttttattttc ttaacaccac ctaaaaatgt tattggcgaa    240

agaagaattt cacattataa agtaaataat gcatgggcta cattagaagg aagtccaacc    300

gaagtatcgg ggacaccttt atatgcggga agaaacgtat tagataactc aaaaggaaca    360

atagatcaag agatgttaac acccgagttt aactatacct atacggaagg cacttcaaat    420

acaacaactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctttagag ttttagcata cctaaatact ggatctattt caggtgaagc taacctttac    660

gcaaatgttg gggtgtagc ttgggggggtt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcacatc taattatgga    840

acggacttca ttttaaaaat tgaagacatc acagattcaa agttacgaaa caataacggg    900

agtggaactg tcgttcaaga gattaaagtt ccactaatta gaactgaaat atag          954


<210> SEQ ID NO 10
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC4078 precursor protein from the open reading frame as set forth
```

in SEQ ID NO:9.

<400> SEQUENCE: 10

```
Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Val Ala Trp
        35                  40                  45

Asn Thr Asn Phe Lys Pro Ser Asp Glu Gln Gln Phe Ser Tyr Ser Pro
    50                  55                  60

Thr Glu Gly Phe Ile Phe Leu Thr Pro Pro Lys Asn Val Ile Gly Glu
65                  70                  75                  80

Arg Arg Ile Ser His Tyr Lys Val Asn Asn Ala Trp Ala Thr Leu Glu
                85                  90                  95

Gly Ser Pro Thr Glu Val Ser Gly Thr Pro Leu Tyr Ala Gly Arg Asn
            100                 105                 110

Val Leu Asp Asn Ser Lys Gly Thr Ile Asp Gln Glu Met Leu Thr Pro
        115                 120                 125

Glu Phe Asn Tyr Thr Tyr Thr Glu Gly Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Val Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Thr Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 11
<211> LENGTH: 954
<212> TYPE: DNA
<213> ORGANISM: Artificial Sequence
<220> FEATURE:
<223> OTHER INFORMATION: A recombinant polynucleotide sequence encoding a collage TIC4260 protein created by combining the natural sequence variation from six native sequences from a Brevibacillus laterosporus species.

<400> SEQUENCE: 11

```
atgaaaaaat ttgcaagttt aattcttaca agtgtgttcc ttttttcgag tacgcaattt      60
```

-continued

```
gttcatgcgt catccataga tgttcaagaa agattacggg acttggcaag agaagatgaa    120

gctggaacct ttaatgtagc atggaatact aacttcaaac ccagtgatga acaacaattc    180

tcgtatagtc caactgaagg ttttattttc ttaacaccac ctaaaaatgt tattggcgaa    240

agaagaattt cacattataa agtaaataat gcatgggcta cattagtagg aagtccaacc    300

gaagcatcgg ggacaccttt atatgcggga agaaacgtat tagataactc aaaaggaaca    360

atggatcaag agatgttaac acccgagttt agttatacct atacggaagg cacttcaaat    420

acaataactc atggattaaa agtaggagtc aaaaccactg ctaccatgaa attccccgatt   480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg ggggtgtagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcacatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 12
<211> LENGTH: 317
<212> TYPE: PRT
<213> ORGANISM: Artificial Sequence
<220> FEATURE:
<223> OTHER INFORMATION: The amino acid sequence translation of the open reading frame as set forth in SEQ ID NO:11.

<400> SEQUENCE: 12

```
Met Lys Lys Phe Ala Ser Leu Ile Leu Thr Ser Val Phe Leu Phe Ser
1               5                   10                  15

Ser Thr Gln Phe Val His Ala Ser Ser Ile Asp Val Gln Glu Arg Leu
            20                  25                  30

Arg Asp Leu Ala Arg Glu Asp Glu Ala Gly Thr Phe Asn Val Ala Trp
        35                  40                  45

Asn Thr Asn Phe Lys Pro Ser Asp Glu Gln Gln Phe Ser Tyr Ser Pro
    50                  55                  60

Thr Glu Gly Phe Ile Phe Leu Thr Pro Pro Lys Asn Val Ile Gly Glu
65                  70                  75                  80

Arg Arg Ile Ser His Tyr Lys Val Asn Asn Ala Trp Ala Thr Leu Val
                85                  90                  95

Gly Ser Pro Thr Glu Ala Ser Gly Thr Pro Leu Tyr Ala Gly Arg Asn
            100                 105                 110

Val Leu Asp Asn Ser Lys Gly Thr Met Asp Gln Glu Met Leu Thr Pro
        115                 120                 125

Glu Phe Ser Tyr Thr Tyr Thr Glu Gly Thr Ser Asn Thr Ile Thr His
    130                 135                 140

Gly Leu Lys Val Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205
```

```
Asn Thr Gly Ser Ile Ser Gly Glu Ala Asn Leu Tyr Ala Asn Val Gly
    210                 215                 220

Gly Val Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Thr Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 13
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4346 protein from an open reading frame at nucleotide position 1-951 and a translation termination codon.

<400> SEQUENCE: 13

```
atgaaaaaat ttgcaagttt aattcttata agtgtgttcc ttttttcgag tacgcaattt     60

gttcatgcgt catccacaga tgttcaagaa agattacggg acttagcaag agaaaatgaa    120

gctggaaccc ttaatgaagc atggaatact aacttcaaac ccagtgatga acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaataactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctttagag ttttagcata cctaaatact ggatctattt caggtgaagc taacctttac    660

gcaaatgttg gggtatagc ttggggggtt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcgaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 14
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC4346 precursor protein from the open reading frame as set forth in SEQ ID NO:13.

<400> SEQUENCE: 14

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Ile Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Glu Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 15
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4826 protein from an open reading frame at nucleotide position 1-951 and a translation termination codon.

<400> SEQUENCE: 15

-continued

```
atgaaaaaat ttgcaagttt aattcttata agtgtgttcc ttttttcgag tacgcaattt      60

gttcatgcgt catccacaga tgttcaagaa agattacggg acttggcaag agaaaatgaa     120

gctggaaccc ttaatgaagc atggaatact aacttcaaac ccagtgatga acaacaattc     180

tcttatagtc ccactgaagg tattgttttc ttaacaccac ctaaaaatgt tattggcgaa     240

agaagaattt cacagtataa agtaaataat gcatgggcta cattagaagg aagtccaacc     300

gaagtatcgg ggacaccttt atatgcggga aaaaacgtat tagataactc aaaaggaaca     360

atggatcaag agctgttaac acccgagttt aactatacct atacggaaag cacttcaaat     420

acaacaactc atggattaaa attaggagtc aaaaccactg ctaccatgaa attccccgatt    480

gctcagggta gcatggaagc ttctactgaa tataactttc aaaattcttc cactgatact     540

aaaactaaac aagtatcata taaaagccca tcacaaaaaa ttaaagtacc agcaggtaaa     600

acctatagag ttttagcata cctaaatact ggatctatat caggtgaagc taacctttac     660

gcaaatgttg ggggtatagc ttggggggtt ttaccaggtt atcccaatgg cggaggaata     720

aatataggtg ctgtacttac caaatgccaa caaaaaggat ggggagattt cagaaacttt     780

caacctagtg gaagagatgt aatcgttaaa ggccaaggta ctttcaaatc taattatgga     840

acggacttca ttttaaaaat tgaagacatc acagattcaa agttacgaaa caataacggg     900

agtggaactg tcgttcaaga gattaaagtt ccactaatta gaactgaaat atag           954
```

<210> SEQ ID NO 16
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC4826 precursor protein from the open reading frame as set forth in SEQ ID NO:15.

<400> SEQUENCE: 16

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175
```

-continued

```
Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Ile
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

```
<210> SEQ ID NO 17
<211> LENGTH: 921
<212> TYPE: DNA
<213> ORGANISM: Brevibacillus laterosporus
<220> FEATURE:
<221> NAME/KEY: misc_feature
<222> LOCATION: (1)..(921)
<223> OTHER INFORMATION: A recombinant polynucleotide sequence obtained
      from a Brevibacillus laterosporus species encoding a TIC4861
      protein from an open reading frame at nucleotide position 1-918
      and a translation termination codon.

<400> SEQUENCE: 17

atgttccttt tttcgagtac gcaatttgtt catgcgtcat ccacagatgt tcaagaacga      60

ttacgggact tggcaagaga aaatgaagct ggaaccctta atgaagcatg gaatactaac     120

ttcaaaccca gtgatgaaca acaattctct tatagtccaa ctgaaggtat tgttttctta     180

acaccaccta aaaatgttat tggcgaaaga agaatttcac agtataaagt aaataatgca     240

tgggctacat tagaaggaag tccaaccgaa gtatcgggga cacctttata tgcgggaaaa     300

aacgtattag ataactcaaa agggacaagc gatcaagagc tgttaacacc cgagtttaac     360

tatacctata cggaaagcac ttcaaataca acaactcatg gattaaaatt aggagtcaaa     420

accactgcta ccatgaaatt cccgattgct cagggtagca tggaagcttc tactgaatat     480

aactttcaaa attcttccac tgatactaaa actaaacaag tatcatataa aagcccatca     540

caaaaaaatta aagtaccagc aggtaaaacc tatagagttt tagcatacct aaatactgga     600

tctatttcag gtgaagctaa cctttacgca aatattgggg gtatagcttg ggggggttta     660

ccaggttatc ccaatggcgg aggagtaaat ataggtgctg tacttaccaa atgccaacaa     720

aaaggatggg gagatttcag aaactttcaa cctagtggaa gagatgtaat cgttaaaggc     780

caaggtactt tcaaatctaa ttatggaacg gacttcattt taaaaattga agacatcaca     840

gattcaaagt tacgaaacaa taacgggagt ggaactgtcg ttcaagagat taaagttcca     900

ctaattagaa ctgaaatata g                                               921


<210> SEQ ID NO 18
<211> LENGTH: 306
<212> TYPE: PRT
<213> ORGANISM: Brevibacillus laterosporus
```

-continued

<220> FEATURE:
<221> NAME/KEY: MISC_FEATURE
<222> LOCATION: (1)..(306)
<223> OTHER INFORMATION: The amino acid sequence translation of the
      TIC4861 precursor protein from the open reading frame as set forth
      in SEQ ID NO:17.

<400> SEQUENCE: 18

```
Met Phe Leu Phe Ser Ser Thr Gln Phe Val His Ala Ser Ser Thr Asp
1               5                   10                  15

Val Gln Glu Arg Leu Arg Asp Leu Ala Arg Glu Asn Glu Ala Gly Thr
            20                  25                  30

Leu Asn Glu Ala Trp Asn Thr Asn Phe Lys Pro Ser Asp Glu Gln Gln
        35                  40                  45

Phe Ser Tyr Ser Pro Thr Glu Gly Ile Val Phe Leu Thr Pro Pro Lys
    50                  55                  60

Asn Val Ile Gly Glu Arg Arg Ile Ser Gln Tyr Lys Val Asn Asn Ala
65                  70                  75                  80

Trp Ala Thr Leu Glu Gly Ser Pro Thr Glu Val Ser Gly Thr Pro Leu
                85                  90                  95

Tyr Ala Gly Lys Asn Val Leu Asp Asn Ser Lys Gly Thr Ser Asp Gln
            100                 105                 110

Glu Leu Leu Thr Pro Glu Phe Asn Tyr Thr Tyr Thr Glu Ser Thr Ser
        115                 120                 125

Asn Thr Thr Thr His Gly Leu Lys Leu Gly Val Lys Thr Thr Ala Thr
    130                 135                 140

Met Lys Phe Pro Ile Ala Gln Gly Ser Met Glu Ala Ser Thr Glu Tyr
145                 150                 155                 160

Asn Phe Gln Asn Ser Ser Thr Asp Thr Lys Thr Lys Gln Val Ser Tyr
                165                 170                 175

Lys Ser Pro Ser Gln Lys Ile Lys Val Pro Ala Gly Lys Thr Tyr Arg
            180                 185                 190

Val Leu Ala Tyr Leu Asn Thr Gly Ser Ile Ser Gly Glu Ala Asn Leu
        195                 200                 205

Tyr Ala Asn Ile Gly Gly Ile Ala Trp Gly Gly Leu Pro Gly Tyr Pro
    210                 215                 220

Asn Gly Gly Gly Val Asn Ile Gly Ala Val Leu Thr Lys Cys Gln Gln
225                 230                 235                 240

Lys Gly Trp Gly Asp Phe Arg Asn Phe Gln Pro Ser Gly Arg Asp Val
                245                 250                 255

Ile Val Lys Gly Gln Gly Thr Phe Lys Ser Asn Tyr Gly Thr Asp Phe
            260                 265                 270

Ile Leu Lys Ile Glu Asp Ile Thr Asp Ser Lys Leu Arg Asn Asn Asn
        275                 280                 285

Gly Ser Gly Thr Val Val Gln Glu Ile Lys Val Pro Leu Ile Arg Thr
    290                 295                 300

Glu Ile
305
```

<210> SEQ ID NO 19
<211> LENGTH: 948
<212> TYPE: DNA
<213> ORGANISM: Brevibacillus laterosporus
<220> FEATURE:
<221> NAME/KEY: misc_feature
<222> LOCATION: (1)..(948)
<223> OTHER INFORMATION: A recombinant polynucleotide sequence obtained
      from a Brevibacillus laterosporus species encoding a TIC4862 protein from an open reading frame at nucleotide position 1-945
and a translation termination codon.

<400> SEQUENCE: 19
atgtttgcaa gtttaattct tataagtgtg ttcctttttt cgagtacgca atttgttcat 60
gcgtcatcca cagatgttca agaacgatta cgggacttgg caagagaaaa tgaagctgga 120
acccttaatg aagcatggaa tactaacttc aaacccagtg atgaacaaca attctcttat 180
agtccaactg aaggtattgt tttcttaaca ccacctaaaa atgttattgg cgaaagaaga 240
atttcacagt ataaagtaaa taatgcatgg gctacattag aaggaagtcc aaccgaagta 300
tcggggacac ctttatatgc gggaaaaaac gtattagata actcaaaagg gacaagcgat 360
caagagctgt taacacccga gtttaactat acctatacgg aaagcacttc aaatacaaca 420
actcatggat taaaattagg agtcaaaacc actgctacca tgaaattccc gattgctcag 480
ggtagcatgg aagcttctac tgaatataac tttcaaaatt cttccactga tactaaaact 540
aaacaagtat catataaaag cccatcacaa aaaattaaag taccagcagg taaaacctat 600
agagttttag catacctaaa tactggatct atttcaggtg aagctaacct ttacgcaaat 660
attgggggta tagcttgggg gggtttacca ggttatccca atggcggagg agtaaatata 720
ggtgctgtac ttaccaaatg ccaacaaaaa ggatggggag atttcagaaa ctttcaacct 780
agtggaagag atgtaatcgt taaaggccaa ggtactttca aatctaatta tggaacggac 840
ttcattttaa aaattgaaga catcacagat tcaaagttac gaaacaataa cgggagtgga 900
actgtcgttc aagagattaa agttccacta attagaactg aaatatag 948

<210> SEQ ID NO 20
<211> LENGTH: 315
<212> TYPE: PRT
<213> ORGANISM: Brevibacillus laterosporus
<220> FEATURE:
<221> NAME/KEY: MISC_FEATURE
<222> LOCATION: (1)..(315)
<223> OTHER INFORMATION: The amino acid sequence translation of the
TIC4862 precursor protein from the open reading frame as set forth
in SEQ ID NO:19.

<400> SEQUENCE: 20

Met Phe Ala Ser Leu Ile Leu Ile Ser Val Phe Leu Phe Ser Ser Thr
1 5 10 15

Gln Phe Val His Ala Ser Ser Thr Asp Val Gln Glu Arg Leu Arg Asp
20 25 30

Leu Ala Arg Glu Asn Glu Ala Gly Thr Leu Asn Glu Ala Trp Asn Thr
35 40 45

Asn Phe Lys Pro Ser Asp Glu Gln Gln Phe Ser Tyr Ser Pro Thr Glu
50 55 60

Gly Ile Val Phe Leu Thr Pro Pro Lys Asn Val Ile Gly Glu Arg Arg
65 70 75 80

Ile Ser Gln Tyr Lys Val Asn Asn Ala Trp Ala Thr Leu Glu Gly Ser
85 90 95

Pro Thr Glu Val Ser Gly Thr Pro Leu Tyr Ala Gly Lys Asn Val Leu
100 105 110

Asp Asn Ser Lys Gly Thr Ser Asp Gln Glu Leu Leu Thr Pro Glu Phe
115 120 125

Asn Tyr Thr Tyr Thr Glu Ser Thr Ser Asn Thr Thr Thr His Gly Leu
130 135 140

Lys Leu Gly Val Lys Thr Thr Ala Thr Met Lys Phe Pro Ile Ala Gln

-continued

```
145                 150                 155                 160

Gly Ser Met Glu Ala Ser Thr Glu Tyr Asn Phe Gln Asn Ser Ser Thr
                165                 170                 175

Asp Thr Lys Thr Lys Gln Val Ser Tyr Lys Ser Pro Ser Gln Lys Ile
            180                 185                 190

Lys Val Pro Ala Gly Lys Thr Tyr Arg Val Leu Ala Tyr Leu Asn Thr
        195                 200                 205

Gly Ser Ile Ser Gly Glu Ala Asn Leu Tyr Ala Asn Ile Gly Gly Ile
    210                 215                 220

Ala Trp Gly Gly Leu Pro Gly Tyr Pro Asn Gly Gly Gly Val Asn Ile
225                 230                 235                 240

Gly Ala Val Leu Thr Lys Cys Gln Gln Lys Gly Trp Gly Asp Phe Arg
                245                 250                 255

Asn Phe Gln Pro Ser Gly Arg Asp Val Ile Val Lys Gly Gln Gly Thr
            260                 265                 270

Phe Lys Ser Asn Tyr Gly Thr Asp Phe Ile Leu Lys Ile Glu Asp Ile
        275                 280                 285

Thr Asp Ser Lys Leu Arg Asn Asn Asn Gly Ser Gly Thr Val Val Gln
    290                 295                 300

Glu Ile Lys Val Pro Leu Ile Arg Thr Glu Ile
305                 310                 315
```

<210> SEQ ID NO 21
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4863 protein from an open reading frame at nucleotide position 1-951 and a translation termination codon.

<400> SEQUENCE: 21

```
atgaaaaaat ttgcaagttt aattcttata agtgtgttcc ttttttcgag tacgcaattt     60

gttcatgcgt catccacaga tgttcaagaa cgattacggg acttggcaag agaaaatgaa    120

gctggaaccc ttaatgaagc atggaatact aacttcaaac ccagtgatga acaacaattc    180

tcttatagtc caactgaagg tattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgcggga aaaaacgtat tagataactc aaaagggaca    360

agcgatcaag agctgttaac acccgagttt aactatacct atacggaaag cacttcaaat    420

acaacaactc atggattaaa attaggagtc aaaaccactg ctaccatgaa attccccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatattg gggtatagc ttgggggggt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 22
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC4863 precursor protein from the open reading frame as set forth in SEQ ID NO:21.

<400> SEQUENCE: 22

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Ser Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Ile Gly
    210                 215                 220

Gly Ile Ala Trp Gly Gly Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 23
<211> LENGTH: 295
<212> TYPE: PRT
<213> ORGANISM: Artificial Sequence
<220> FEATURE:
<223> OTHER INFORMATION: An amino acid sequence of a mature TIC3668 protein, mTIC3688.

<400> SEQUENCE: 23

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Val Gly Ser Pro Thr Glu Ala
65 70 75 80

Ser Gly Thr Pro Leu Tyr Ala Gly Lys Asn Val Leu Asp Asn Ser Lys
85 90 95

Gly Thr Met Asp Gln Glu Leu Leu Thr Pro Glu Phe Asn Tyr Thr Tyr
100 105 110

Thr Glu Ser Thr Ser Asn Thr Ile Thr His Gly Leu Lys Leu Gly Val
115 120 125

Lys Thr Thr Ala Thr Met Lys Phe Pro Ile Ala Gln Gly Ser Met Glu
130 135 140

Ala Ser Thr Glu Tyr Asn Phe Gln Asn Ser Ser Thr Asp Thr Lys Thr
145 150 155 160

Lys Gln Val Ser Tyr Lys Ser Pro Ser Gln Lys Ile Lys Val Pro Ala
165 170 175

Gly Lys Thr Tyr Arg Val Leu Ala Tyr Leu Asn Thr Gly Ser Ile Ser
180 185 190

Gly Glu Ala Asn Leu Tyr Ala Asn Val Gly Gly Ile Ala Trp Arg Val
195 200 205

Ser Pro Gly Tyr Pro Asn Gly Gly Gly Val Asn Ile Gly Ala Val Leu
210 215 220

Thr Lys Cys Gln Gln Lys Gly Trp Gly Asp Phe Arg Asn Phe Gln Pro
225 230 235 240

Ser Gly Arg Asp Val Ile Val Lys Gly Gln Gly Thr Phe Lys Ser Asn
245 250 255

Tyr Gly Thr Asp Phe Ile Leu Lys Ile Glu Asp Ile Thr Asp Ser Lys
260 265 270

Leu Arg Asn Asn Asn Gly Ser Gly Thr Val Val Gln Glu Ile Lys Val
275 280 285

Pro Leu Ile Arg Thr Glu Ile
290 295

<210> SEQ ID NO 24
<211> LENGTH: 295
<212> TYPE: PRT
<213> ORGANISM: Artificial Sequence
<220> FEATURE:
<223> OTHER INFORMATION: An amino acid sequence of a mature TIC3669 protein mTIC3669.

<400> SEQUENCE: 24

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Val
65 70 75 80

Ser Gly Thr Pro Leu Tyr Ala Gly Lys Asn Val Leu Asp Asn Ser Lys
85 90 95

Gly Thr Ile Asp Gln Glu Leu Leu Thr Pro Glu Phe Ser Tyr Thr Tyr
100 105 110

Thr Glu Ser Thr Ser Asn Thr Thr Thr His Gly Leu Lys Val Gly Val
115 120 125

Lys Thr Thr Ala Thr Met Lys Phe Pro Ile Ala Gln Gly Ser Met Glu
130 135 140

Ala Ser Thr Glu Tyr Asn Phe Gln Asn Ser Ser Thr Asp Thr Lys Thr
145 150 155 160

Lys Gln Val Ser Tyr Lys Ser Pro Ser Gln Lys Ile Lys Val Pro Ala
165 170 175

Gly Lys Thr Tyr Arg Val Leu Ala Tyr Leu Asn Thr Gly Ser Ile Ser
180 185 190

Gly Glu Ala Asn Leu Tyr Ala Asn Val Gly Gly Ile Ala Trp Arg Val
195 200 205

Ser Pro Gly Tyr Pro Asn Gly Gly Gly Val Asn Ile Gly Ala Val Leu
210 215 220

Thr Lys Cys Gln Gln Lys Gly Trp Gly Asp Phe Arg Asn Phe Gln Pro
225 230 235 240

Ser Gly Arg Asp Val Ile Val Lys Gly Gln Gly Thr Phe Lys Ser Asn
245 250 255

Tyr Gly Thr Asp Phe Ile Leu Lys Ile Glu Asp Ile Thr Asp Ser Lys
260 265 270

Leu Arg Asn Asn Asn Gly Ser Gly Thr Val Val Gln Glu Ile Lys Val
275 280 285

Pro Leu Ile Arg Thr Glu Ile
290 295

<210> SEQ ID NO 25
<211> LENGTH: 295
<212> TYPE: PRT
<213> ORGANISM: Artificial Sequence
<220> FEATURE:
<223> OTHER INFORMATION: An amino acid sequence of a mature TIC3670 protein, mTIC3670.

<400> SEQUENCE: 25

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Ala
65 70 75 80

Ser Gly Thr Pro Leu Tyr Ala Gly Lys Asn Val Leu Asp Asn Ser Lys

```
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295


<210> SEQ ID NO 26
<211> LENGTH: 295
<212> TYPE: PRT
<213> ORGANISM: Artificial Sequence
<220> FEATURE:
<223> OTHER INFORMATION: An amino acid sequence of a mature TIC4076
      protein, mTIC4076.

<400> SEQUENCE: 26

Met Ser Ser Thr Asp Val Gln Glu Arg Leu Arg Asp Leu Ala Arg Glu
1               5                   10                  15

Asn Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Met
65                  70                  75                  80

Ser Gly Thr Pro Leu Tyr Ala Gly Lys Asn Val Leu Asp Asn Ser Lys
                85                  90                  95

Gly Thr Ser Asp Gln Glu Leu Leu Thr Pro Glu Phe Thr Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140
```

```
Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Gly Val
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Thr Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295


<210> SEQ ID NO 27
<211> LENGTH: 295
<212> TYPE: PRT
<213> ORGANISM: Artificial Sequence
<220> FEATURE:
<223> OTHER INFORMATION: An amino acid sequence of a mature TIC4078
      protein, mTIC4078.

<400> SEQUENCE: 27

Met Ser Ser Thr Asp Val Gln Glu Arg Leu Arg Asp Leu Ala Arg Glu
1               5                   10                  15

Asn Glu Ala Gly Thr Leu Asn Val Ala Trp Asn Thr Asn Phe Lys Pro
            20                  25                  30

Ser Asp Glu Gln Gln Phe Ser Tyr Ser Pro Thr Glu Gly Phe Ile Phe
        35                  40                  45

Leu Thr Pro Pro Lys Asn Val Ile Gly Glu Arg Arg Ile Ser His Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Arg Asn Val Leu Asp Asn Ser Lys
                85                  90                  95

Gly Thr Ile Asp Gln Glu Met Leu Thr Pro Glu Phe Asn Tyr Thr Tyr
            100                 105                 110

Thr Glu Gly Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Val Ala Trp Gly Val
        195                 200                 205
```

```
Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Thr Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 28
<211> LENGTH: 295
<212> TYPE: PRT
<213> ORGANISM: Artificial Sequence
<220> FEATURE:
<223> OTHER INFORMATION: An amino acid sequence of a mature TIC4260 protein, mTIC4260.

<400> SEQUENCE: 28

```
Met Ser Ser Ile Asp Val Gln Glu Arg Leu Arg Asp Leu Ala Arg Glu
1               5                   10                  15

Asp Glu Ala Gly Thr Phe Asn Val Ala Trp Asn Thr Asn Phe Lys Pro
            20                  25                  30

Ser Asp Glu Gln Gln Phe Ser Tyr Ser Pro Thr Glu Gly Phe Ile Phe
        35                  40                  45

Leu Thr Pro Pro Lys Asn Val Ile Gly Glu Arg Arg Ile Ser His Tyr
    50                  55                  60

Lys Val Asn Asn Ala Trp Ala Thr Leu Val Gly Ser Pro Thr Glu Ala
65                  70                  75                  80

Ser Gly Thr Pro Leu Tyr Ala Gly Arg Asn Val Leu Asp Asn Ser Lys
                85                  90                  95

Gly Thr Met Asp Gln Glu Met Leu Thr Pro Glu Phe Ser Tyr Thr Tyr
            100                 105                 110

Thr Glu Gly Thr Ser Asn Thr Ile Thr His Gly Leu Lys Val Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Val Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Thr Ser Asn
                245                 250                 255

Tyr Gly Thr Asp Phe Ile Leu Lys Ile Glu Asp Ile Thr Asp Ser Lys
```

```
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 29
<211> LENGTH: 295
<212> TYPE: PRT
<213> ORGANISM: Artificial Sequence
<220> FEATURE:
<223> OTHER INFORMATION: An amino acid sequence of a mature TIC4346 protein, mTIC4346.

<400> SEQUENCE: 29

```
Met Ser Ser Thr Asp Val Gln Glu Arg Leu Arg Asp Leu Ala Arg Glu
1               5                   10                  15

Asn Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Ile Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Gly Val
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Glu Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 30
<211> LENGTH: 295

<212> TYPE: PRT
<213> ORGANISM: Artificial Sequence
<220> FEATURE:
<223> OTHER INFORMATION: An amino acid sequence of a mature TIC4826 protein, mTIC4826.

<400> SEQUENCE: 30

Met Ser Ser Thr Asp Val Gln Glu Arg Leu Arg Asp Leu Ala Arg Glu
1 5 10 15

Asn Glu Ala Gly Thr Leu Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Val
65 70 75 80

Ser Gly Thr Pro Leu Tyr Ala Gly Lys Asn Val Leu Asp Asn Ser Lys
85 90 95

Gly Thr Met Asp Gln Glu Leu Leu Thr Pro Glu Phe Asn Tyr Thr Tyr
100 105 110

Thr Glu Ser Thr Ser Asn Thr Thr Thr His Gly Leu Lys Leu Gly Val
115 120 125

Lys Thr Thr Ala Thr Met Lys Phe Pro Ile Ala Gln Gly Ser Met Glu
130 135 140

Ala Ser Thr Glu Tyr Asn Phe Gln Asn Ser Ser Thr Asp Thr Lys Thr
145 150 155 160

Lys Gln Val Ser Tyr Lys Ser Pro Ser Gln Lys Ile Lys Val Pro Ala
165 170 175

Gly Lys Thr Tyr Arg Val Leu Ala Tyr Leu Asn Thr Gly Ser Ile Ser
180 185 190

Gly Glu Ala Asn Leu Tyr Ala Asn Val Gly Gly Ile Ala Trp Gly Val
195 200 205

Leu Pro Gly Tyr Pro Asn Gly Gly Gly Ile Asn Ile Gly Ala Val Leu
210 215 220

Thr Lys Cys Gln Gln Lys Gly Trp Gly Asp Phe Arg Asn Phe Gln Pro
225 230 235 240

Ser Gly Arg Asp Val Ile Val Lys Gly Gln Gly Thr Phe Lys Ser Asn
245 250 255

Tyr Gly Thr Asp Phe Ile Leu Lys Ile Glu Asp Ile Thr Asp Ser Lys
260 265 270

Leu Arg Asn Asn Asn Gly Ser Gly Thr Val Val Gln Glu Ile Lys Val
275 280 285

Pro Leu Ile Arg Thr Glu Ile
290 295

<210> SEQ ID NO 31
<211> LENGTH: 295
<212> TYPE: PRT
<213> ORGANISM: Artificial Sequence
<220> FEATURE:
<223> OTHER INFORMATION: An amino acid sequence of a mature TIC4861 protein, mTIC4861.

<400> SEQUENCE: 31

Met Ser Ser Thr Asp Val Gln Glu Arg Leu Arg Asp Leu Ala Arg Glu
1 5 10 15

-continued

```
Asn Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Ser Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Ile Gly Gly Ile Ala Trp Gly Gly
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 32
<211> LENGTH: 954
<212> TYPE: DNA
<213> ORGANISM: Artificial Sequence
<220> FEATURE:
<223> OTHER INFORMATION: A synthetic nucleotide sequence encoding a TIC3668 protein designed for expression in plants.

<400> SEQUENCE: 32

```
atgaagaagt tcgcgtcgct gatcctcacc agcgtgttcc tgtttagtag cacgcagttc      60

gtccacgcct catccacgga cgtgcaagag cgcctgcggg acttggcgcg cgaagacgag     120

gcgggaacgt tcaacgaggc ttggaacacc aacttcaagc cgtcggacga gcagcaattc     180

agctactcgc cgacggaggg aattgtcttc ctcacgccgc ctaagaacgt catcggtgag     240

cggcgcatct cccagtacaa ggtgaacaat gcctgggcaa ctctggtggg ctctcccacc     300

gaggcgagcg gtacgccgtt gtacgcgggc aagaatgtac tggacaactc gaaaggcaca     360

atggaccagg agttgcttac acccgagttc aactacacct acacggagag cacgagcaac     420
```

-continued acgatcacgc acggcctcaa actcggcgtg aagaccaccg cgaccatgaa gttccctatc 480
gctcaaggct cgatggaggc gagcaccgag tacaatttcc agaactcctc caccgatacc 540
aagaccaaac aagtgtctta caagtctccg agccagaaga ttaaggttcc tgcgggcaag 600
acgtaccgcg tgctggcgta cctgaacacc ggctctatct ctggcgaggc taacctgtac 660
gcgaacgtcg gcggcatcgc gtggcgggtc tcgccaggct atcctaacgg cggcggcgtg 720
aacatcggcg ctgtcctgac caagtgccag cagaagggtt ggggcgactt ccgcaacttc 780
cagccctccg ggcgcgacgt catcgtgaag ggtcagggca ccttcaagtc caactacggc 840
accgacttca tccttaagat tgaggacatc accgacagca agctccgcaa caacaacggc 900
tccgggacgg tcgtacagga gatcaaggtg ccactcatcc gcaccgagat ttga 954

<210> SEQ ID NO 33
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC3668 protein, mTIC3668 designed for expression in plants.

<400> SEQUENCE: 33
atgtcatcca cggacgtgca agagcgcctg cgggacttgg cgcgcgaaga cgaggcggga 60
acgttcaacg aggcttggaa caccaacttc aagccgtcgg acgagcagca attcagctac 120
tcgccgacgg agggaattgt cttcctcacg ccgcctaaga acgtcatcgg tgagcggcgc 180
atctcccagt acaaggtgaa caatgcctgg gcaactctgg tgggctctcc caccgaggcg 240
agcggtacgc cgttgtacgc gggcaagaat gtactggaca actcgaaagg cacaatggac 300
caggagttgc ttacacccga gttcaactac acctacacgg agagcacgag caacacgatc 360
acgcacggcc tcaaactcgg cgtgaagacc accgcgacca tgaagttccc tatcgctcaa 420
ggctcgatgg aggcgagcac cgagtacaat ttccagaact cctccaccga taccaagacc 480
aaacaagtgt cttacaagtc tccgagccag aagattaagg ttcctgcggg caagacgtac 540
cgcgtgctgg cgtacctgaa caccggctct atctctggcg aggctaacct gtacgcgaac 600
gtcggcggca tcgcgtggcg ggtctcgcca ggctatccta acggcggcgg cgtgaacatc 660
ggcgctgtcc tgaccaagtg ccagcagaag ggttggggcg acttccgcaa cttccagccc 720
tccgggcgcg acgtcatcgt gaagggtcag ggcaccttca agtccaacta cggcaccgac 780
ttcatcctta agattgagga catcaccgac agcaagctcc gcaacaacaa cggctccggg 840
acggtcgtac aggagatcaa ggtgccactc atccgcaccg agatttga 888

<210> SEQ ID NO 34
<211> LENGTH: 954
<212> TYPE: DNA
<213> ORGANISM: Artificial Sequence
<220> FEATURE:
<223> OTHER INFORMATION: A synthetic nucleotide sequence encoding a TIC3669 protein designed for expression in plants.

<400> SEQUENCE: 34
atgaagaagt tcgcgtcgct gatcctcatc agcgtgttcc tgtttagtag cacgcagttc 60
gtccacgcct catccacgga cgtgcaagag cgcctgcggg acttggcgcg cgaagacgag 120
gcgggaacgt tcaacgaggc ttggaacacc aacttcaagc cgtcggacga gcagcaattc 180
agctactcgc cgacggaggg aattgtcttc ctcacgccgc ctaagaacgt catcggtgag 240

```
cggcgcatct cccagtacaa ggtgaacaat gcctgggcaa ctctggaggg ctctcccacc    300
gaggtcagcg gtacgccgtt gtacgcgggc aagaatgtac tggacaactc gaaaggcaca    360
atagaccagg agttgcttac acccgagttc tcgtacacct acacggagag cacgagcaac    420
acgacgacgc acggcctcaa agtcggcgtg aagaccaccg cgaccatgaa gttccctatc    480
gctcaaggct cgatggaggc gagcaccgag tacaatttcc agaactcctc caccgatacc    540
aagaccaaac aagtgtctta caagtctccg agccagaaga ttaaggttcc tgcgggcaag    600
acgtaccgcg tgctggcgta cctgaacacc ggctctatct ctggcgaggc taacctgtac    660
gcgaacgtcg gcggcatcgc gtggcgggtc tcgccaggct atcctaacgg cggcggcgtg    720
aacatcggcg ctgtcctgac caagtgccag cagaagggtt ggggcgactt ccgcaacttc    780
cagccctccg ggcgcgacgt catcgtgaag ggtcagggca ccttcaagtc caactacggc    840
accgacttca tccttaagat tgaggacatc accgacagca agctccgcaa caacaacggc    900
tccgggacgg tcgtacagga gatcaaggtg ccactcatcc gcaccgagat ttga          954
```

<210> SEQ ID NO 35
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC3669 protein, mTIC3669 designed for expression in plants.

<400> SEQUENCE: 35

```
atgtcatcca cggacgtgca agagcgcctg cgggacttgg cgcgcgaaga cgaggcggga     60
acgttcaacg aggcttggaa caccaacttc aagccgtcgg acgagcagca attcagctac    120
tcgccgacgg agggaattgt cttcctcacg ccgcctaaga acgtcatcgg tgagcggcgc    180
atctcccagt acaaggtgaa caatgcctgg gcaactctgg agggctctcc caccgaggtc    240
agcggtacgc cgttgtacgc gggcaagaat gtactggaca actcgaaagg cacaatagac    300
caggagttgc ttacacccga gttctcgtac acctacacgg agagcacgag caacacgacg    360
acgcacggcc tcaaagtcgg cgtgaagacc accgcgacca tgaagttccc tatcgctcaa    420
ggctcgatgg aggcgagcac cgagtacaat ttccagaact cctccaccga taccaagacc    480
aaacaagtgt cttacaagtc tccgagccag aagattaagg ttcctgcggg caagacgtac    540
cgcgtgctgg cgtacctgaa caccggctct atctctggcg aggctaacct gtacgcgaac    600
gtcggcggca tcgcgtggcg ggtctcgcca ggctatccta acggcggcgg cgtgaacatc    660
ggcgctgtcc tgaccaagtg ccagcagaag ggttggggcg acttccgcaa cttccagccc    720
tccgggcgcg acgtcatcgt gaagggtcag ggcaccttca agtccaacta cggcaccgac    780
ttcatcctta agattgagga catcaccgac agcaagctcc gcaacaacaa cggctccggg    840
acggtcgtac aggagatcaa ggtgccactc atccgcaccg agatttga                 888
```

<210> SEQ ID NO 36
<211> LENGTH: 954
<212> TYPE: DNA
<213> ORGANISM: Artificial Sequence
<220> FEATURE:
<223> OTHER INFORMATION: A synthetic nucleotide sequence encoding a TIC3670 protein designed for expression in plants.

<400> SEQUENCE: 36

```
atgaagaagt tcgcgtcgct gatcctcacc agcgtgttcc tgtttagtag cacgcagttc     60
```

```
gtccacgcct catccacgga cgtgcaagag cgcctgcggg acttggcgcg cgaagacgag    120

gcgggaacgt tcaacgaggc ttggaacacc aacttcaagc cgtcggacga gcagcaattc    180

agctactcgc cgacggaggg aattgtcttc ctcacgccgc ctaagaacgt catcggtgag    240

cggcgcatct cccagtacaa ggtgaacaat gcctgggcaa ctctggaggg ctctcccacc    300

gaggcgagcg gtacgccgtt gtacgcgggc aagaatgtac tggacaactc gaaaggcaca    360

atggaccagg agttgcttac acccgagttc aactacacct acacggagag cacgagcaac    420

acgacgacgc acggcctcaa actcggcgtg aagaccaccg cgaccatgaa gttccctatc    480

gctcaaggct cgatggaggc gagcaccgag tacaatttcc agaactcctc caccgatacc    540

aagaccaaac aagtgtctta caagtctccg agccagaaga ttaaggttcc tgcgggcaag    600

acgtaccgcg tgctggcgta cctgaacacc ggctctatct ctggcgaggc taacctgtac    660

gcgaacgtcg gcggcatcgc gtggcgggtc tcgccaggct atcctaacgg cggcggcgtg    720

aacatcggcg ctgtcctgac caagtgccag cagaagggtt ggggcgactt ccgcaacttc    780

cagccctccg ggcgcgacgt catcgtgaag ggtcagggca ccttcaagtc caactacggc    840

accgacttca tccttaagat tgaggacatc accgacagca agctccgcaa caacaacggc    900

tccgggacgg tcgtacagga gatcaaggtg ccactcatcc gcaccgagat ttga          954
```

<210> SEQ ID NO 37
<211> LENGTH: 888
<212> TYPE: DNA
<213> ORGANISM: Artificial Sequence
<220> FEATURE:
<223> OTHER INFORMATION: A a synthetic nucleotide sequence encoding a mature TIC3670 protein, mTIC3670 designed for expression in plants.

<400> SEQUENCE: 37

```
atgtcatcca cggacgtgca agagcgcctg cgggacttgg cgcgcgaaga cgaggcggga     60

acgttcaacg aggcttggaa caccaacttc aagccgtcgg acgagcagca attcagctac    120

tcgccgacgg agggaattgt cttcctcacg ccgcctaaga acgtcatcgg tgagcggcgc    180

atctcccagt acaaggtgaa caatgcctgg gcaactctgg agggctctcc caccgaggcg    240

agcggtacgc cgttgtacgc gggcaagaat gtactggaca actcgaaagg cacaatggac    300

caggagttgc ttacacccga gttcaactac acctacacgg agagcacgag caacacgacg    360

acgcacggcc tcaaactcgg cgtgaagacc accgcgacca tgaagttccc tatcgctcaa    420

ggctcgatgg aggcgagcac cgagtacaat ttccagaact cctccaccga taccaagacc    480

aaacaagtgt cttacaagtc tccgagccag aagattaagg ttcctgcggg caagacgtac    540

cgcgtgctgg cgtacctgaa caccggctct atctctggcg aggctaacct gtacgcgaac    600

gtcggcggca tcgcgtggcg ggtctcgcca ggctatccta acggcggcgg cgtgaacatc    660

ggcgctgtcc tgaccaagtg ccagcagaag ggttggggcg acttccgcaa cttccagccc    720

tccgggcgcg acgtcatcgt gaagggtcag ggcaccttca agtccaacta cggcaccgac    780

ttcatcctta agattgagga catcaccgac agcaagctcc gcaacaacaa cggctccggg    840

acggtcgtac aggagatcaa ggtgccactc atccgcaccg agatttga                 888
```

<210> SEQ ID NO 38
<211> LENGTH: 954
<212> TYPE: DNA
<213> ORGANISM: Artificial Sequence
<220> FEATURE:
<223> OTHER INFORMATION: A synthetic nucleotide sequence encoding a TIC4076 protein designed for expression in plants.

<400> SEQUENCE: 38
atgaagaagt tcgcgagttt gatcctgatc agtgtgttcc tcttctcctc tacccagttc 60
gtgcacgcga gcagcaccga cgtgcaagag cgcctgcggg acctcgcacg ggagaacgaa 120
gccgggacct taaacgaggc ctggaacact aacttcaagc cctccgacga gcagcagttc 180
tcctacagcc ctactgaggg tatcgtcttc ttgacgcctc ctaagaacgt catcggtgag 240
cgccgcatca gccagtacaa ggtgaacaat gcctgggcca cgttggaagg aagccctacc 300
gagatgtccg gtacgccgtt gtacgccggc aagaacgtgc tagacaactc caaaggcacg 360
tccgaccagg agctgctcac tccagagttc acttacacct acaccgagag tacatcaaac 420
accaccaccc acggcctgaa gctgggcgtg aagaccactg caaccatgaa gtttccgata 480
gcccagggct ccatggaggc gagcacagag tacaacttcc agaactcctc gaccgacacg 540
aagaccaagc aagtatctta caagtcgccg tcacagaaga tcaaggtccc tgcgggcaag 600
acgttcaggg tcctggcgta cctgaacacc ggatcaatct ccggcgaggc gaatctgtac 660
gctaatgtag gtggcatcgc ctggggtgtg ctgccaggct accctaacgg tggaggcgta 720
aacatcggag ccgtgttgac gaaatgccag cagaagggct ggggcgattt cagaaacttt 780
caaccgagcg ggagggacgt cattgtgaag ggccagggca cattcacatc caactacggg 840
acagacttca tcctgaagat cgaggacata accgacagca aactgaggaa caataacgga 900
tcgggtacgg tagtacagga gatcaaagtc ccgctgatcc ggacggagat ctag 954

<210> SEQ ID NO 39
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4076 protein, mTIC4076 designed for expression in plants.

<400> SEQUENCE: 39
atgagcagca ccgacgtgca agagcgcctg cgggacctcg cacgggagaa cgaagccggg 60
accttaaacg aggcctggaa cactaacttc aagccctccg acgagcagca gttctcctac 120
agccctactg agggtatcgt cttcttgacg cctcctaaga acgtcatcgg tgagcgccgc 180
atcagccagt acaaggtgaa caatgcctgg gccacgttgg aaggaagccc taccgagatg 240
tccggtacgc cgttgtacgc cggcaagaac gtgctagaca actccaaagg cacgtccgac 300
caggagctgc tcactccaga gttcacttac acctacaccg agagtacatc aaacaccacc 360
acccacggcc tgaagctggg cgtgaagacc actgcaacca tgaagtttcc gatagcccag 420
ggctccatgg aggcgagcac agagtacaac ttccagaact cctcgaccga cacgaagacc 480
aagcaagtat cttacaagtc gccgtcacag aagatcaagg tccctgcggg caagacgttc 540
agggtcctgg cgtacctgaa caccggatca atctccggcg aggcgaatct gtacgctaat 600
gtaggtggca tcgcctgggg tgtgctgcca ggctacccta acggtggagg cgtaaacatc 660
ggagccgtgt tgacgaaatg ccagcagaag ggctggggcg atttcagaaa ctttcaaccg 720
agcgggaggg acgtcattgt gaagggccag ggcacattca catccaacta cgggacagac 780
ttcatcctga agatcgagga cataaccgac agcaaactga ggaacaataa cggatcgggt 840
acggtagtac aggagatcaa agtcccgctg atccggacgg agatctag 888

<210> SEQ ID NO 40
<211> LENGTH: 888
<212> TYPE: DNA
<213> ORGANISM: Artificial Sequence
<220> FEATURE:
<223> OTHER INFORMATION: A synthetic nucleotide sequence encoding a TIC4078 protein designed for expression in plants.

<400> SEQUENCE: 40

```
atgagcagca ccgacgtgca agagcgcctg cgggacctcg cacgggagaa cgaagccggg     60

accttaaacg aggcctggaa cactaacttc aagccctccg acgagcagca gttctcctac    120

agccctactg agggtatcgt cttcttgacg cctcctaaga acgtcatcgg tgagcgccgc    180

atcagccagt acaaggtgaa caatgcctgg gccacgttgg aaggaagccc taccgagatg    240

tccggtacgc cgttgtacgc cggcaagaac gtgctagaca actccaaagg cacgtccgac    300

caggagctgc tcactccaga gttcacttac acctacaccg agagtacatc aaacaccacc    360

acccacggcc tgaagctggg cgtgaagacc actgcaacca tgaagtttcc gatagcccag    420

ggctccatgg aggcgagcac agagtacaac ttccagaact cctcgaccga cacgaagacc    480

aagcaagtat cttacaagtc gccgtcacag aagatcaagg tccctgcggg caagacgttc    540

agggtcctgg cgtacctgaa caccggatca atctccggcg aggcgaatct gtacgctaat    600

gtaggtggca tcgcctgggg tgtgctgcca ggctacccta acggtggagg cgtaaacatc    660

ggagccgtgt tgacgaaatg ccagcagaag ggctggggcg atttcagaaa ctttcaaccg    720

agcgggaggg acgtcattgt gaagggccag ggcacattca catccaacta cgggacagac    780

ttcatcctga agatcgagga cataaccgac agcaaactga ggaacaataa cggatcgggt    840

acggtagtac aggagatcaa agtcccgctg atccggacgg agatctag                 888
```

<210> SEQ ID NO 41
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4078 protein, mTIC4078 designed for expression in plants.

<400> SEQUENCE: 41

```
atgagctcca ccgacgttca ggagcgcctc cgggacttgg caagagagaa tgaggcgggt     60

acgctcaatg tcgcctggaa caccaacttc aagccgtccg acgaacagca gttctcctac    120

tctcctacgg aagggttcat cttcctgaca ccgcccaaga acgtcatcgg cgagcggcgc    180

atcagccatt acaaggtcaa caatgcgtgg gctacgctgg agggcagtcc gaccgaggtg    240

agcggcactc cactctacgc cgggagaaac gtcctcgaca attccaaggg caccatcgac    300

caggagatgt tgacgcctga gttcaactac acgtacaccg agggcacctc taacaccacc    360

actcatggcc tcaagcttgg cgtgaagaca actgcgacaa tgaagtttcc catcgcccaa    420

ggcagtatgg aggcctcgac ggagtacaac ttccagaaca gcagcaccga cactaagacc    480

aagcaagtgt cctacaagag tccatcacag aagatcaaag tcccggccgg caagacattc    540

cgagtgctgg cgtacctaaa caccgggtcg atctcgggcg aggccaacct ttacgccaat    600

gtgggcggcg tcgcatgggg cgtgctgccc ggctatccga acggaggcgg cgtgaacatc    660

ggcgctgtgc tcaccaagtg ccaacagaag ggatggggcg acttccgcaa cttccaaccc    720

tccggtaggg acgtcatagt gaagggccag ggcacgttta catctaacta cgggacggac    780

ttcatactca agatcgagga catcacagat agtaagctca ggaacaacaa cgggtccggc    840
```

accgtcgttc aggagatcaa ggtcccgttg attaggacgg agatctga 888

<210> SEQ ID NO 42
<211> LENGTH: 954
<212> TYPE: DNA
<213> ORGANISM: Artificial Sequence
<220> FEATURE:
<223> OTHER INFORMATION: A synthetic nucleotide sequence encoding a TIC4260 protein designed for expression in plants.

<400> SEQUENCE: 42
atgaagaagt tcgcctcact gatccttacc tcggtcttcc tgttctcttc cactcagttc 60
gtgcacgcca gctccataga cgtccaggag cggctcaggg acttggcgcg ggaggacgag 120
gccggcacct ttaacgtggc ctggaacacg aactttaagc cttcagacga gcagcagttc 180
tcctacagcc ctactgaggg cttcatcttt ctgactccgc caaagaatgt gatcggcgaa 240
aggcggatca gtcactacaa agtgaacaac gcttgggcca cgctcgtggg ctcacccacg 300
gaagcgtcag ggacgcctct ctacgccggt aggaacgtgc tggataattc caagggtacg 360
atggaccagg agatgctgac gcccgagttc agctacactt acacagaggg cacgtccaac 420
acgatcacac atgggctcaa ggtgggtgtc aagaccaccg ctaccatgaa gttcccgatc 480
gctcagggct ccatggaagc gagcacagag tacaactttc agaactcttc gacggacacg 540
aagaccaagc aagtttccta caagagccct agccagaaga tcaaggtccc tgcgggcaag 600
acgtaccgcg ttctggccta tctgaacacc ggctccataa gcggcgaggc gaacctgtac 660
gctaatgtgg gtggcgtcgc ttggcgcgtc agtccgggtt acccgaacgg cggcggcgtg 720
aacatcggcg ccgtgttaac taagtgccag cagaagggct ggggcgactt cagaaatttc 780
cagccttccg gccgggacgt catcgtgaag ggccagggca ccttcacctc aaactacggg 840
acagacttta tccttaagat cgaggacatc accgacagca agctccgaaa caacaacggc 900
tccggcaccg tcgtgcaaga gattaaggtc ccgctcatta ggacggagat ctaa 954

<210> SEQ ID NO 43
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4260 protein, mTIC4260 designed for expression in plants.

<400> SEQUENCE: 43
atgagctcca tagacgtcca ggagcggctc agggacttgg cgcgggagga cgaggccggc 60
acctttaacg tggcctggaa cacgaacttt aagccttcag acgagcagca gttctcctac 120
agccctactg agggcttcat ctttctgact ccgccaaaga atgtgatcgg cgaaaggcgg 180
atcagtcact acaaagtgaa caacgcttgg gccacgctcg tgggctcacc cacggaagcg 240
tcagggacgc ctctctacgc cggtaggaac gtgctggata attccaaggg tacgatggac 300
caggagatgc tgacgcccga gttcagctac acttacacag agggcacgtc caacacgatc 360
acacatgggc tcaaggtggg tgtcaagacc accgctacca tgaagttccc gatcgctcag 420
ggctccatgg aagcgagcac agagtacaac tttcagaact cttcgacgga cacgaagacc 480
aagcaagttt cctacaagag ccctagccag aagatcaagg tccctgcggg caagacgtac 540
cgcgttctgg cctatctgaa caccggctcc ataagcggcg aggcgaacct gtacgctaat 600
gtgggtggcg tcgcttggcg cgtcagtccg ggttacccga acggcggcgg cgtgaacatc 660

```
ggcgccgtgt taactaagtg ccagcagaag ggctggggcg acttcagaaa tttccagcct    720

tccggccggg acgtcatcgt gaagggccag ggcaccttca cctcaaacta cgggacagac    780

tttatcctta agatcgagga catcaccgac agcaagctcc gaaacaacaa cggctccggc    840

accgtcgtgc aagagattaa ggtcccgctc attaggacgg agatctaa                 888
```

<210> SEQ ID NO 44
<211> LENGTH: 954
<212> TYPE: DNA
<213> ORGANISM: Artificial Sequence
<220> FEATURE:
<223> OTHER INFORMATION: A synthetic nucleotide sequence encoding a TIC4346 protein designed for expression in plants.

<400> SEQUENCE: 44

```
atgaagaagt tcgcgagttt gatcctgatc agtgtgttcc tcttctcctc tacccagttc     60

gtgcacgcgt cctccaccga cgtgcaagag aggctgaggg acttggctcg agagaacgag    120

gccgggaccc tgaacgaggc gtggaacacg aatttcaagc cttccgatga gcaacagttc    180

tcctacagcc ctaccgaagg gattgtgttc ctcacgcctc ccaagaacgt gatcggcgag    240

cgccgcatct cgcagtacaa ggtgaacaac gcctgggcga cgctcgaggg ctcacccacc    300

gaggtctcgg gcactccgct gtacgccggc aagaacgtcc ttgacaactc caagggaacc    360

atggatcaag agctattgac gccggagttc aactacacgt acaccgagag caccagcaac    420

acgatcacac acggcctcaa gctaggcgtg aagacgactg cgacaatgaa gttcccgatc    480

gcacagggct cgatggaggc cagcacggag tacaacttcc agaactcgtc caccgacacg    540

aagactaagc aagtgtcata caagtctccc tcacagaaga taaaggtgcc ggccggcaag    600

acgtttcgcg tcctggccta cttaaacacg ggttccatta gcggtgaggc caacctctat    660

gcgaatgtgg gcggaattgc gtggggcgtc ctgcccggat acccgaacgg cggcggcgtc    720

aacatcggcg ccgtgttgac gaaatgtcag cagaagggct ggggcgattt ccgtaacttc    780

cagccgtccg gccgcgacgt gatagtgaag ggacagggaa cgttcgagtc aaactacggc    840

acagacttca tcttaaagat cgaagacata acagactcga agctgcgcaa caataacggc    900

tcaggcacgg tcgttcagga gattaaggtg cctctcatcc ggacagagat ctag          954
```

<210> SEQ ID NO 45
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4346 protein, mTIC4346 designed for expression in plants.

<400> SEQUENCE: 45

```
atgtcctcca ccgacgtgca agagaggctg agggacttgg ctcgagagaa cgaggccggg     60

accctgaacg aggcgtggaa cacgaatttc aagccttccg atgagcaaca gttctcctac    120

agccctaccg aagggattgt gttcctcacg cctcccaaga acgtgatcgg cgagcgccgc    180

atctcgcagt acaaggtgaa caacgcctgg gcgacgctcg agggctcacc caccgaggtc    240

tcgggcactc cgctgtacgc cggcaagaac gtccttgaca actccaaggg aaccatggat    300

caagagctat tgacgccgga gttcaactac acgtacaccg agagcaccag caacacgatc    360

acacacggcc tcaagctagg cgtgaagacg actgcgacaa tgaagttccc gatcgcacag    420

ggctcgatgg aggccagcac ggagtacaac ttccagaact cgtccaccga cacgaagact    480
```

```
aagcaagtgt catacaagtc tccctcacag aagataaagg tgccggccgg caagacgttt    540

cgcgtcctgg cctacttaaa cacgggttcc attagcggtg aggccaacct ctatgcgaat    600

gtgggcggaa ttgcgtgggg cgtcctgccc ggatacccga acggcggcgg cgtcaacatc    660

ggcgccgtgt tgacgaaatg tcagcagaag ggctggggcg atttccgtaa cttccagccg    720

tccggccgcg acgtgatagt gaagggacag ggaacgttcg agtcaaacta cggcacagac    780

ttcatcttaa agatcgaaga cataacagac tcgaagctgc gcaacaataa cggctcaggc    840

acggtcgttc aggagattaa ggtgcctctc atccggacag agatctag                 888
```

<210> SEQ ID NO 46
<211> LENGTH: 954
<212> TYPE: DNA
<213> ORGANISM: Artificial Sequence
<220> FEATURE:
<223> OTHER INFORMATION: A synthetic nucleotide sequence encoding a TIC4826 protein designed for expression in plants.

<400> SEQUENCE: 46

```
atgaagaagt tcgcgagttt gatcctgatc agtgtgttcc tcttctcctc tacccagttc     60

gtgcacgcga gctcgacgga cgtccaggaa cggctccggg accttgcgcg cgagaacgag    120

gccgggacgt tgaacgaggc ctggaacacc aacttcaaac cgagcgacga gcagcagttc    180

agctactctc ccacggaggg catagtcttc ctcacgcctc ccaagaacgt gatcggcgag    240

aggcgcatct cccagtacaa ggtgaacaac gcctgggcga ccttggaggg ctctcccacg    300

gaggtgtccg gcactccgct ctacgccggc aagaacgtct tagacaacag caaagggacc    360

atggatcagg agctattgac gccggagttc aattacacgt acaccgaaag tacaagtaat    420

acgaccactc atggcctgaa gctcggcgtg aagactacag caacaatgaa gtttcccatt    480

gcccaagggt cgatggaggc ctcgaccgag tacaatttcc agaactcctc aacagacact    540

aagaccaaac aggtgtcgta caagagccct agccagaaga tcaaagtccc ggccggcaag    600

acctacaggg tgctggcgta cctcaacacc ggctctatct cgggcgaggc gaacctctac    660

gcgaacgtgg gcgggatcgc atggggtgtg ctacctggtt acccgaacgg aggcggcatc    720

aacatcggcg cggtgctgac aaagtgccag cagaagggtt ggggcgactt tcgcaacttc    780

cagccgagcg ggagagacgt catcgtgaag ggccagggca ccttcaagag caattacggc    840

acggacttca tcctcaagat tgaagacatc accgacagca agctgcgaaa taacaacggg    900

tcgggcaccg tcgtccagga gatcaaagtg ccgctcatcc ggaccgagat ctag          954
```

<210> SEQ ID NO 47
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4826 protein, mTIC4826 designed for expression in plants.

<400> SEQUENCE: 47

```
atgagctcga cggacgtcca ggaacggctc cgggaccttg cgcgcgagaa cgaggccggg     60

acgttgaacg aggcctggaa caccaacttc aaaccgagcg acgagcagca gttcagctac    120

tctcccacgg agggcatagt cttcctcacg cctcccaaga acgtgatcgg cgagaggcgc    180

atctcccagt acaaggtgaa caacgcctgg gcgaccttgg agggctctcc cacggaggtg    240

tccggcactc cgctctacgc cggcaagaac gtcttagaca acagcaaagg gaccatggat    300
```

```
caggagctat tgacgccgga gttcaattac acgtacaccg aaagtacaag taatacgacc    360

actcatggcc tgaagctcgg cgtgaagact acagcaacaa tgaagtttcc cattgcccaa    420

gggtcgatgg aggcctcgac cgagtacaat ttccagaact cctcaacaga cactaagacc    480

aaacaggtgt cgtacaagag ccctagccag aagatcaaag tcccggccgg caagacctac    540

agggtgctgg cgtacctcaa caccggctct atctcgggcg aggcgaacct ctacgcgaac    600

gtgggcggga tcgcatgggg tgtgctacct ggttacccga acggaggcgg catcaacatc    660

ggcgcggtgc tgacaaagtg ccagcagaag ggttggggcg actttcgcaa cttccagccg    720

agcgggagag acgtcatcgt gaagggccag ggcaccttca agagcaatta cggcacggac    780

ttcatcctca agattgaaga catcaccgac agcaagctgc gaaataacaa cgggtcgggc    840

accgtcgtcc aggagatcaa agtgccgctc atccggaccg agatctag                888
```

<210> SEQ ID NO 48
<211> LENGTH: 921
<212> TYPE: DNA
<213> ORGANISM: Artificial Sequence
<220> FEATURE:
<223> OTHER INFORMATION: A synthetic nucleotide sequence encoding a TIC4861 protein designed for expression in plants.

<400> SEQUENCE: 48

```
atgtttctgt tctcgagcac ccagtttgtg cacgcgtcct ccacggatgt gcaagagcgg     60

ctccgcgacc tagcccgcga gaacgaggct ggcacactga acgaggcgtg gaacacgaac    120

ttcaagccga gcgacgagca gcagttctcc tactcgccga ctgagggcat cgtcttcctg    180

acgcctccca agaacgtaat cggcgagcgg aggattagtc agtacaaggt gaacaatgcg    240

tgggcaacgc tcgagggtag cccaaccgag gtctccggca cgccgctcta cgcgggaaag    300

aacgtcctgg acaattccaa gggcaccagc gaccaggagc tgcttacgcc ggagtttaat    360

tacacctaca cagagtcgac ctcgaatacg acaacacacg gccttaagct gggcgttaag    420

acaacggcga cgatgaagtt tcccattgcc cagggttcga tggaagcttc tacggagtac    480

aactttcaga actcgagcac agacacaaag acgaagcaag tgtcctacaa gagccctagc    540

cagaagataa aggtccctgc cggcaagaca tacagggtct tagcgtacct caacaccggc    600

tcgatctcag gagaggccaa cctgtacgcc aacatcggcg ggatcgcctg ggtggcctc     660

ccgggctacc ctaacggcgg cggtgtgaac atcggcgctg tcctgacgaa atgccagcag    720

aaagggtggg gcgacttccg aaacttccag ccgagcgggc gcgacgttat cgtcaagggt    780

cagggcactt tcaagtctaa ttacggaacc gatttcattc tgaagatcga ggacattacc    840

gatagcaagc tccggaacaa caacggcagc ggtacggttg tccaggagat caaggtccct    900

ctgatacgaa cagagatttg a                                              921
```

<210> SEQ ID NO 49
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4861 protein, a mature TIC4862 protein, and a mature TIC4863 protein designed for expression in plants.

<400> SEQUENCE: 49

```
atgtcctcca cggatgtgca agagcggctc cgcgacctag cccgcgagaa cgaggctggc     60

acactgaacg aggcgtggaa cacgaacttc aagccgagcg acgagcagca gttctcctac    120
```

tcgccgactg agggcatcgt cttcctgacg cctcccaaga acgtaatcgg cgagcggagg 180
attagtcagt acaaggtgaa caatgcgtgg gcaacgctcg agggtagccc aaccgaggtc 240
tccggcacgc cgctctacgc gggaaagaac gtcctggaca attccaaggg caccagcgac 300
caggagctgc ttacgccgga gtttaattac acctacacag agtcgacctc gaatacgaca 360
acacacggcc ttaagctggg cgttaagaca acggcgacga tgaagtttcc cattgcccag 420
ggttcgatgg aagcttctac ggagtacaac tttcagaact cgagcacaga cacaaagacg 480
aagcaagtgt cctacaagag ccctagccag aagataaagg tccctgccgg caagacatac 540
agggtcttag cgtacctcaa caccggctcg atctcaggag aggccaacct gtacgccaac 600
atcggcggga tcgcctgggg tggcctcccg ggctacccta acggcggcgg tgtgaacatc 660
ggcgctgtcc tgacgaaatg ccagcagaaa gggtggggcg acttccgaaa cttccagccg 720
agcgggcgcg acgttatcgt caagggtcag ggcactttca agtctaatta cggaaccgat 780
ttcattctga agatcgagga cattaccgat agcaagctcc ggaacaacaa cggcagcggt 840
acggttgtcc aggagatcaa ggtccctctg atacgaacag agatttga 888

<210> SEQ ID NO 50
<211> LENGTH: 948
<212> TYPE: DNA
<213> ORGANISM: Artificial Sequence
<220> FEATURE:
<223> OTHER INFORMATION: A synthetic nucleotide sequence encoding a TIC4682 protein designed for expression in plants.

<400> SEQUENCE: 50
atgttcgcgt cgctcattct gatctccgtg tttctcttct cgtcgaccca gttcgtgcac 60
gcgtcctcca cggatgtgca agagcggctc cgcgacctag cccgcgagaa cgaggctggc 120
acactgaacg aggcgtggaa cacgaacttc aagccgagcg acgagcagca gttctcctac 180
tcgccgactg agggcatcgt cttcctgacg cctcccaaga acgtaatcgg cgagcggagg 240
attagtcagt acaaggtgaa caatgcgtgg gcaacgctcg agggtagccc aaccgaggtc 300
tccggcacgc cgctctacgc gggaaagaac gtcctggaca attccaaggg caccagcgac 360
caggagctgc ttacgccgga gtttaattac acctacacag agtcgacctc gaatacgaca 420
acacacggcc ttaagctggg cgttaagaca acggcgacga tgaagtttcc cattgcccag 480
ggttcgatgg aagcttctac ggagtacaac tttcagaact cgagcacaga cacaaagacg 540
aagcaagtgt cctacaagag ccctagccag aagataaagg tccctgccgg caagacatac 600
agggtcttag cgtacctcaa caccggctcg atctcaggag aggccaacct gtacgccaac 660
atcggcggga tcgcctgggg tggcctcccg ggctacccta acggcggcgg tgtgaacatc 720
ggcgctgtcc tgacgaaatg ccagcagaaa gggtggggcg acttccgaaa cttccagccg 780
agcgggcgcg acgttatcgt caagggtcag ggcactttca agtctaatta cggaaccgat 840
ttcattctga agatcgagga cattaccgat agcaagctcc ggaacaacaa cggcagcggt 900
acggttgtcc aggagatcaa ggtccctctg atacgaacag agatttga 948

<210> SEQ ID NO 51
<211> LENGTH: 954
<212> TYPE: DNA
<213> ORGANISM: Artificial Sequence
<220> FEATURE:
<223> OTHER INFORMATION: A synthetic nucleotide sequence encoding a TIC4863 protein designed for expression in plants.

<400> SEQUENCE: 51
atgaagaagt tcgcgagttt gatcctgatc agtgtgttcc tcttctcctc tacccagttc 60
gtgcacgcgt cctccacgga tgtgcaagag cggctccgcg acctagcccg cgagaacgag 120
gctggcacac tgaacgaggc gtggaacacg aacttcaagc cgagcgacga gcagcagttc 180
tcctactcgc cgactgaggg catcgtcttc ctgacgcctc ccaagaacgt aatcggcgag 240
cggaggatta gtcagtacaa ggtgaacaat gcgtgggcaa cgctcgaggg tagcccaacc 300
gaggtctccg gcacgccgct ctacgcggga aagaacgtcc tggacaattc caagggcacc 360
agcgaccagg agctgcttac gccggagttt aattacacct acacagagtc gacctcgaat 420
acgacaacac acggccttaa gctgggcgtt aagacaacgg cgacgatgaa gtttcccatt 480
gcccagggtt cgatggaagc ttctacggag tacaactttc agaactcgag cacagacaca 540
aagacgaagc aagtgtccta caagagccct agccagaaga taaaggtccc tgccggcaag 600
acatacaggg tcttagcgta cctcaacacc ggctcgatct caggagaggc caacctgtac 660
gccaacatcg gcgggatcgc ctggggtggc ctcccgggct accctaacgg cggcggtgtg 720
aacatcggcg ctgtcctgac gaaatgccag cagaaagggt ggggcgactt ccgaaacttc 780
cagccgagcg ggcgcgacgt tatcgtcaag ggtcagggca ctttcaagtc taattacgga 840
accgatttca ttctgaagat cgaggacatt accgatagca agctccggaa caacaacggc 900
agcggtacgg ttgtccagga gatcaaggtc cctctgatac gaacagagat ttga 954

<210> SEQ ID NO 52
<211> LENGTH: 36
<212> TYPE: DNA
<213> ORGANISM: Artificial Sequence
<220> FEATURE:
<223> OTHER INFORMATION: A nucleotide sequence representing a synthetic oligonucleotide for hybridizing to the (-) strand of a DNA encoding a protein disclosed in this application and corresponds to positions 1 to 36 of SEQ ID NO:1 (TIC3668 forward primer).

<400> SEQUENCE: 52
atgaaaaaat ttgcaagttt aattcttaca agtgtg 36

<210> SEQ ID NO 53
<211> LENGTH: 34
<212> TYPE: DNA
<213> ORGANISM: Artificial Sequence
<220> FEATURE:
<223> OTHER INFORMATION: A nucleotide sequence representing a synthetic oligonucleotide for hybridizing to the (+) strand of a DNA encoding a protein disclosed in this application and corresponds to positions 920 to 954 of SEQ ID NO:1 (TIC3668 reverse primer).

<400> SEQUENCE: 53
ctatatttca gttctaatta gtggaacttt aatc 34

<210> SEQ ID NO 54
<211> LENGTH: 41
<212> TYPE: DNA
<213> ORGANISM: Artificial Sequence
<220> FEATURE:
<223> OTHER INFORMATION: A nucleotide sequence representing a synthetic oligonucleotide for hybridizing to the (-) strand of a DNA encoding a protein disclosed in this application and corresponds to positions 1 to 41 of SEQ ID NO:3 (TIC3669 forward primer).

<400> SEQUENCE: 54
atgaaaaaat ttgcaagttt aattcttata agtgtgttcc t 41

<210> SEQ ID NO 55
<211> LENGTH: 34
<212> TYPE: DNA
<213> ORGANISM: Artificial Sequence
<220> FEATURE:
<223> OTHER INFORMATION: A nucleotide sequence representing a synthetic oligonucleotide for hybridizing to the (+) strand of a DNA encoding a protein disclosed in this application and corresponds to positions 920 to 954 of SEQ ID NO:3 (TIC3669 reverse primer).

<400> SEQUENCE: 55
ctatatttca gttctaatta gtggaacttt aatc 34

<210> SEQ ID NO 56
<211> LENGTH: 36
<212> TYPE: DNA
<213> ORGANISM: Artificial Sequence
<220> FEATURE:
<223> OTHER INFORMATION: A nucleotide sequence representing a synthetic oligonucleotide for hybridizing to the (-) strand of a DNA encoding a protein disclosed in this application and corresponds to positions 1 to 36 of SEQ ID NO:5 (TIC3670 forward primer).

<400> SEQUENCE: 56
atgaaaaaat ttgcaagttt aattcttaca agtgtg 36

<210> SEQ ID NO 57
<211> LENGTH: 34
<212> TYPE: DNA
<213> ORGANISM: Artificial Sequence
<220> FEATURE:
<223> OTHER INFORMATION: A nucleotide sequence representing a synthetic oligonucleotide for hybridizing to the (+) strand of a DNA encoding a protein disclosed in this application and corresponds to positions 920 to 954 of SEQ ID NO:5 (TIC3670 reverse primer).

<400> SEQUENCE: 57
ctatatttca gttctaatta gtggaacttt aatc 34

<210> SEQ ID NO 58
<211> LENGTH: 41
<212> TYPE: DNA
<213> ORGANISM: Artificial Sequence
<220> FEATURE:
<223> OTHER INFORMATION: A nucleotide sequence representing a synthetic oligonucleotide for hybridizing to the (-) strand of a DNA encoding a protein disclosed in this application and corresponds to positions 1 to 41 of SEQ ID NO:7 (TIC4076 forward primer).

<400> SEQUENCE: 58
atgaaaaaat ttgcaagttt aattcttata agtgtgttcc t 41

<210> SEQ ID NO 59
<211> LENGTH: 34
<212> TYPE: DNA
<213> ORGANISM: Artificial Sequence
<220> FEATURE:
<223> OTHER INFORMATION: A nucleotide sequence representing a synthetic oligonucleotide for hybridizing to the (+) strand of a DNA encoding a protein disclosed in this application and corresponds to positions 920 to 954 of SEQ ID NO:7 (TIC4076 reverse primer).

<400> SEQUENCE: 59
ctatatttca gttctaatta gtggaacttt aatc 34

<210> SEQ ID NO 60
<211> LENGTH: 36
<212> TYPE: DNA

<213> ORGANISM: Artificial Sequence
<220> FEATURE:
<223> OTHER INFORMATION: A nucleotide sequence representing a synthetic oligonucleotide for hybridizing to the (-) strand of a DNA encoding a protein disclosed in this application and corresponds to positions 1 to 36 of SEQ ID NO:9 (TIC4078 forward primer).

<400> SEQUENCE: 60
atgaaaaaat ttgcaagttt aattcttaca agtgtg 36

<210> SEQ ID NO 61
<211> LENGTH: 34
<212> TYPE: DNA
<213> ORGANISM: Artificial Sequence
<220> FEATURE:
<223> OTHER INFORMATION: A nucleotide sequence representing a synthetic oligonucleotide for hybridizing to the (+) strand of a DNA encoding a protein disclosed in this application and corresponds to positions 920 to 954 of SEQ ID NO:9 (TIC4078 reverse primer).

<400> SEQUENCE: 61
ctatatttca gttctaatta gtggaacttt aatc 34

<210> SEQ ID NO 62
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC2462 protein from an open reading frame at nucleotide position 1-951 and a translation termination codon.

<400> SEQUENCE: 62
atgaaaaaat ttgcaagttt aattcttata agtgtgttcc ttttttcgag tacgcaattt 60
gttcatgcgt catccataga tgttcaagaa agattacggg acttggcaag agaaaatgaa 120
gctggaaccc ttaatgaagc atggaatact aacttcaaac ccagtgatga acaacaattc 180
tcttatagtc caactgaagg tattgttttc ttaacaccac ctaaaaatgt tattggcgaa 240
agaagaattt cacagtataa agtaaataat gcatgggcta cattagaagg aagtccaacc 300
gaagtatcgg ggacaccttt atatgcggga aaaaacgtat tagataactc aaaaggaaca 360
agcgatcaag agctgttaac acccgagttt aactatacct atacggaaag cacttcaaat 420
acaacaactc atggattaaa attaggagtc aaaaccactg ctaccatgaa attccccgatt 480 gctcagggta gcatggaagc ttctactgaa tataactttc aagattcttc cactgatact 540
acaactaaaa cagtatcata taaaagccca tcacaaaaga ttaaagtacc agcaggtaaa 600
acctttagag ttttagcata cctaaatact ggatctattt caggtgaagc taacctttac 660
gcaaatgttg ggggtatagc ttggggagtt ttaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcaaatc taattatgga 840
acggacttca ttttaaaaat tgaagacatc acagattcaa agttacgaaa caataacggg 900
agtggaactg tcgttcaaga gattaaagtt ccactaatta gaactgaaat atag 954

<210> SEQ ID NO 63
<211> LENGTH: 317
<212> TYPE: PRT
<213> ORGANISM: Brevibacillus laterosporus
<220> FEATURE:

<221> NAME/KEY: MISC_FEATURE
<222> LOCATION: (1)..(317)
<223> OTHER INFORMATION: The amino acid sequence translation of the
      TIC3462 protein open reading frame as set forth in SEQ ID NO:62.

<400> SEQUENCE: 63

```
Met Lys Lys Phe Ala Ser Leu Ile Leu Ile Ser Val Phe Leu Phe Ser
1               5                   10                  15

Ser Thr Gln Phe Val His Ala Ser Ser Ile Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Ser Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asp Ser
                165                 170                 175

Ser Thr Asp Thr Thr Thr Lys Thr Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 64
<211> LENGTH: 888
<212> TYPE: DNA
<213> ORGANISM: Artificial Sequence
<220> FEATURE:
<223> OTHER INFORMATION: A synthetic nucleotide sequence encoding a
      mature TIC3668 protein, mTIC3668 for expression in bacteria.

<400> SEQUENCE: 64

```
atgtcatcca cagatgttca agaaagatta cgggacttgg caagagaaga tgaagctgga     60
```

```
acctttaatg aagcatggaa tactaacttc aaacccagtg atgaacaaca attctcgtat    120

agtccaactg aaggaattgt tttcttaaca ccacctaaaa atgttattgg cgaaagaaga    180

atttcacagt ataaagtaaa taatgcatgg gctacattag taggaagtcc aaccgaagca    240

tcggggacac ctttatatgc gggaaaaaac gtattagata actcaaaagg aacaatggat    300

caagagctgt taacacccga gtttaactat acctatacgg aaagcacttc aaatacaata    360

actcatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttca aatctaatta tggaacggac    780

ttcattttaa aaattgaaga catcacagat tcaaagttac gaaacaataa cgggagtgga    840

actgtcgttc aagagattaa agttccacta attagaactg aaatatag                 888
```

<210> SEQ ID NO 65
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC3669 protein, mTIC3669 for expression in bacteria.

<400> SEQUENCE: 65

```
atgtcatcca cagatgttca agaaagatta cgggacttgg caagagaaga tgaagctgga     60

acctttaatg aagcatggaa tactaacttc aaacccagtg atgaacaaca attctcgtat    120

agtccaactg aaggaattgt tttcttaaca ccacctaaaa atgttattgg cgaaagaaga    180

atttcacagt ataaagtaaa taatgcatgg gctacattag aaggaagtcc aaccgaagta    240

tcggggacac ctttatatgc gggaaaaaac gtattagata actcaaaagg aacaatcgat    300

caagagctgt taacacccga gtttagttat acctatacgg aaagcacttc aaatacaaca    360

actcatggat taaaagtagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttca aatctaatta tggaacggac    780

ttcattttaa aaattgaaga catcacagat tcaaagttac gaaacaataa cgggagtgga    840

actgtcgttc aagagattaa agttccacta attagaactg aaatatag                 888
```

<210> SEQ ID NO 66
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC3670 protein, mTIC3670 for expression in bacteria.

<400> SEQUENCE: 66
atgtcatcca cagatgttca agaaagatta cgggacttgg caagagaaga tgaagctgga 60
acctttaatg aagcatggaa tactaacttc aaacccagtg atgaacaaca attctcttat 120
agtccaactg aaggaattgt tttcttaaca ccacctaaaa atgttattgg cgaaagaaga 180
atttcacagt ataaagtaaa taatgcatgg gctacattag aaggaagtcc aaccgaagca 240
tcggggacac ctttatatgc gggaaaaaac gtattagata actcaaaagg aacaatggat 300
caagagctgt taacacccga gtttaactat acctatacgg aaagcacttc aaatacaaca 360
acccatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aaaattaaag taccagcagg taaaacctat 540
agagttttag catacctaaa tactggatct atttcaggtg aagctaacct ttacgcaaat 600
gttgggggta tagcttggag ggtttcacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttca aatctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 67
<211> LENGTH: 888
<212> TYPE: DNA
<213> ORGANISM: Artificial Sequence
<220> FEATURE:
<223> OTHER INFORMATION: A a synthetic nucleotide sequence encoding a
mature TIC4076 protein, mTIC4076 for expression in bacteria.

<400> SEQUENCE: 67
atgtcatcca cagatgttca agaaagatta cgggacttgg caagagaaaa tgaagctgga 60
acccttaatg aagcatggaa tactaacttc aaacccagtg atgaacaaca attctcttat 120
agtccaactg aaggtattgt tttcttaaca ccacctaaaa atgttattgg cgaaagaaga 180
atttcacagt ataaagtaaa taatgcatgg gctacattag aaggaagtcc aaccgaaatg 240
tcggggacac ctttatatgc gggaaaaaac gtattagata actcaaaagg aacaagcgat 300
caagagctgt taacacccga gtttacctat acctatacgg aaagcacttc aaatacaaca 360
actcatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aagattaaag taccagcagg taaaaccttt 540
agagttttag catacctaaa tactggatct atttcaggtg aagctaacct ttacgcaaat 600
gttgggggta tagcttgggg ggttttacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttca catctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 68
<211> LENGTH: 888
<212> TYPE: DNA
<213> ORGANISM: Artificial Sequence
<220> FEATURE:

-continued

<223> OTHER INFORMATION: A synthetic nucleotide sequence encoding a
mature TIC4078 protein, mTIC4078 for expression in bacteria.

<400> SEQUENCE: 68

```
atgtcatcca cagatgttca agaaagatta cgggacttgg caagagaaaa tgaagctgga     60
acccttaatg tagcatggaa tactaacttc aaacccagtg atgaacaaca attctcttat    120
agtccaactg aaggttttat tttcttaaca ccacctaaaa atgttattgg cgaaagaaga    180
atttcacatt ataaagtaaa taatgcatgg gctacattag aaggaagtcc aaccgaagta    240
tcggggacac ctttatatgc gggaagaaac gtattagata actcaaaagg aacaatagat    300
caagagatgt taacacccga gtttaactat acctatacgg aaggcacttc aaatacaaca    360
actcatggat taaaattagg agtcaaaacc actgctacca tgaaattccc gattgctcag    420
ggtagcatgg aagcttctac tgaatataac tttcaaaatt cttccactga tactaaaact    480
aaacaagtat catataaaag cccatcacaa aaaattaaag taccagcagg taaaaccttt    540
agagttttag catacctaaa tactggatct atttcaggtg aagctaacct ttacgcaaat    600
gttgggggtg tagcttgggg ggttttacca ggttatccca atggcggagg agtaaatata    660
ggtgctgtac ttaccaaatg ccaacaaaaa ggatggggag atttcagaaa ctttcaacct    720
agtggaagag atgtaatcgt taaaggccaa ggtactttca catctaatta tggaacggac    780
ttcattttaa aaattgaaga catcacagat tcaaagttac gaaacaataa cgggagtgga    840
actgtcgttc aagagattaa agttccacta attagaactg aaatatag                 888
```

<210> SEQ ID NO 69
<211> LENGTH: 888
<212> TYPE: DNA
<213> ORGANISM: Artificial Sequence
<220> FEATURE:
<223> OTHER INFORMATION: A synthetic nucleotide sequence encoding a
mature TIC4260 protein, mTIC4260 for expression in bacteria.

<400> SEQUENCE: 69

```
atgtcatcca tagatgttca agaaagatta cgggacttgg caagagaaga tgaagctgga     60
acctttaatg tagcatggaa tactaacttc aaacccagtg atgaacaaca attctcgtat    120
agtccaactg aaggttttat tttcttaaca ccacctaaaa atgttattgg cgaaagaaga    180
atttcacatt ataaagtaaa taatgcatgg gctacattag taggaagtcc aaccgaagca    240
tcggggacac ctttatatgc gggaagaaac gtattagata actcaaaagg aacaatggat    300
caagagatgt taacacccga gtttagttat acctatacgg aaggcacttc aaatacaata    360
actcatggat taaaagtagg agtcaaaacc actgctacca tgaaattccc gattgctcag    420
ggtagcatgg aagcttctac tgaatataac tttcaaaatt cttccactga tactaaaact    480
aaacaagtat catataaaag cccatcacaa aaaattaaag taccagcagg taaaacctat    540
agagttttag catacctaaa tactggatct atttcaggtg aagctaacct ttacgcaaat    600
gttgggggtg tagcttggag ggtttcacca ggttatccca atggcggagg agtaaatata    660
ggtgctgtac ttaccaaatg ccaacaaaaa ggatggggag atttcagaaa ctttcaacct    720
agtggaagag atgtaatcgt taaaggccaa ggtactttca catctaatta tggaacggac    780
ttcattttaa aaattgaaga catcacagat tcaaagttac gaaacaataa cgggagtgga    840
actgtcgttc aagagattaa agttccacta attagaactg aaatatag                 888
```

<210> SEQ ID NO 70
<211> LENGTH: 888

<212> TYPE: DNA
<213> ORGANISM: Artificial Sequence
<220> FEATURE:
<223> OTHER INFORMATION: A synthetic nucleotide sequence encoding a mature TIC4346 protein, mTIC4346 for expression in bacteria.

<400> SEQUENCE: 70

```
atgtcatcca cagatgttca agaaagatta cgggacttag caagagaaaa tgaagctgga     60
acccttaatg aagcatggaa tactaacttc aaacccagtg atgaacaaca attctcttat    120
agtccaactg aaggaattgt tttcttaaca ccacctaaaa atgttattgg cgaaagaaga    180
atttcacagt ataaagtaaa taatgcatgg gctacattag aaggaagtcc aaccgaagta    240
tcggggacac ctttatatgc gggaaaaaac gtattagata actcaaaagg aacaatggat    300
caagagctgt taacacccga gtttaactat acctatacgg aaagcacttc aaatacaata    360
actcatggat taaaattagg agtcaaaacc actgctacca tgaaattccc gattgctcag    420
ggtagcatgg aagcttctac tgaatataac tttcaaaatt cttccactga tactaaaact    480
aaacaagtat catataaaag cccatcacaa aaaattaaag taccagcagg taaaaccttt    540
agagttttag catacctaaa tactggatct atttcaggtg aagctaacct ttacgcaaat    600
gttgggggta tagcttgggg ggttttacca ggttatccca atggcggagg agtaaatata    660
ggtgctgtac ttaccaaatg ccaacaaaaa ggatggggag atttcagaaa ctttcaacct    720
agtggaagag atgtaatcgt taaaggccaa ggtactttcg aatctaatta tggaacggac    780
ttcattttaa aaattgaaga catcacagat tcaaagttac gaaacaataa cgggagtgga    840
actgtcgttc aagagattaa agttccacta attagaactg aaatatag                888
```

<210> SEQ ID NO 71
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4826 protein, mTIC4826 for expression in bacteria.

<400> SEQUENCE: 71

```
atgtcatcca cagatgttca agaaagatta cgggacttgg caagagaaaa tgaagctgga     60
acccttaatg aagcatggaa tactaacttc aaacccagtg atgaacaaca attctcttat    120
agtcccactg aaggtattgt tttcttaaca ccacctaaaa atgttattgg cgaaagaaga    180
atttcacagt ataaagtaaa taatgcatgg gctacattag aaggaagtcc aaccgaagta    240
tcggggacac ctttatatgc gggaaaaaac gtattagata actcaaaagg aacaatggat    300
caagagctgt taacacccga gtttaactat acctatacgg aaagcacttc aaatacaaca    360
actcatggat taaaattagg agtcaaaacc actgctacca tgaaattccc gattgctcag    420
ggtagcatgg aagcttctac tgaatataac tttcaaaatt cttccactga tactaaaact    480
aaacaagtat catataaaag cccatcacaa aaaattaaag taccagcagg taaaacctat    540
agagttttag catacctaaa tactggatct atatcaggtg aagctaacct ttacgcaaat    600
gttgggggta tagcttgggg ggttttacca ggttatccca atggcggagg aataaatata    660
ggtgctgtac ttaccaaatg ccaacaaaaa ggatggggag atttcagaaa ctttcaacct    720
agtggaagag atgtaatcgt taaaggccaa ggtactttca aatctaatta tggaacggac    780
ttcattttaa aaattgaaga catcacagat tcaaagttac gaaacaataa cgggagtgga    840
actgtcgttc aagagattaa agttccacta attagaactg aaatatag                888
```

<210> SEQ ID NO 72
<211> LENGTH: 888
<212> TYPE: DNA
<213> ORGANISM: Artificial Sequence
<220> FEATURE:
<223> OTHER INFORMATION: A synthetic nucleotide sequence encoding a mature TIC4861 protein, a mature TIC4862 protein, and a mature TIC4863 protein for expression in bacteria.

<400> SEQUENCE: 72

```
atgtcatcca cagatgttca agaacgatta cgggacttgg caagagaaaa tgaagctgga     60

acccttaatg aagcatggaa tactaacttc aaacccagtg atgaacaaca attctcttat    120

agtccaactg aaggtattgt tttcttaaca ccacctaaaa atgttattgg cgaaagaaga    180

atttcacagt ataaagtaaa taatgcatgg gctacattag aaggaagtcc aaccgaagta    240

tcggggacac ctttatatgc gggaaaaaac gtattagata actcaaaagg gacaagcgat    300

caagagctgt taacacccga gtttaactat acctatacgg aaagcacttc aaatacaaca    360

actcatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

attgggggta tagcttgggg gggtttacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttca aatctaatta tggaacggac    780

ttcattttaa aaattgaaga catcacagat tcaaagttac gaaacaataa cgggagtgga    840

actgtcgttc aagagattaa agttccacta attagaactg aaatatag                888
```

<210> SEQ ID NO 73
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC11239 precursor protein from an open reading frame at nucleotide position 1-951 and a translation termination codon.

<400> SEQUENCE: 73

```
atgaaaaaat ttgcaagttt aattcttata agtgtgttcc ttttttcgag tacccaattt     60

gttcatgcgt catccacaga tgttcaagaa agattacggg acttggcaag agaagatgaa    120

gctggaacct ttaatgaagc atggaatact aacttcaaac ccagtgatga acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaataactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660
```

gcaaatgttg ggggtatagc ttggagggtt tcaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcgaatc taattatgga 840
acggacttca ttttaaaaat tgaagacatc acagattcaa agttacgaaa caataacggg 900
agtggaactg tcgttcaaga gattaaagtt ccactaatta gaactgaaat atag 954

<210> SEQ ID NO 74
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC11239 precursor protein from the open reading frame as set forth in SEQ ID NO:73.

<400> SEQUENCE: 74

Met Lys Lys Phe Ala Ser Leu Ile Leu Ile Ser Val Phe Leu Phe Ser
1 5 10 15

Ser Thr Gln Phe Val His Ala Ser Ser Thr Asp Val Gln Glu Arg Leu
20 25 30

Arg Asp Leu Ala Arg Glu Asp Glu Ala Gly Thr Phe Asn Glu Ala Trp
35 40 45

Asn Thr Asn Phe Lys Pro Ser Asp Glu Gln Gln Phe Ser Tyr Ser Pro
50 55 60

Thr Glu Gly Ile Val Phe Leu Thr Pro Pro Lys Asn Val Ile Gly Glu
65 70 75 80

Arg Arg Ile Ser Gln Tyr Lys Val Asn Asn Ala Trp Ala Thr Leu Glu
85 90 95

Gly Ser Pro Thr Glu Val Ser Gly Thr Pro Leu Tyr Ala Gly Lys Asn
100 105 110

Val Leu Asp Asn Ser Lys Gly Thr Met Asp Gln Glu Leu Leu Thr Pro
115 120 125

Glu Phe Asn Tyr Thr Tyr Thr Glu Ser Thr Ser Asn Thr Ile Thr His
130 135 140

Gly Leu Lys Leu Gly Val Lys Thr Thr Ala Thr Met Lys Phe Pro Ile
145 150 155 160

Ala Gln Gly Ser Met Glu Ala Ser Thr Glu Tyr Asn Phe Gln Asn Ser
165 170 175

Ser Thr Asp Thr Lys Thr Lys Gln Val Ser Tyr Lys Ser Pro Ser Gln
180 185 190

Lys Ile Lys Val Pro Ala Gly Lys Thr Tyr Arg Val Leu Ala Tyr Leu
195 200 205

Asn Thr Gly Ser Ile Ser Gly Glu Ala Asn Leu Tyr Ala Asn Val Gly
210 215 220

Gly Ile Ala Trp Arg Val Ser Pro Gly Tyr Pro Asn Gly Gly Gly Val
225 230 235 240

Asn Ile Gly Ala Val Leu Thr Lys Cys Gln Gln Lys Gly Trp Gly Asp
245 250 255

Phe Arg Asn Phe Gln Pro Ser Gly Arg Asp Val Ile Val Lys Gly Gln
260 265 270

Gly Thr Phe Glu Ser Asn Tyr Gly Thr Asp Phe Ile Leu Lys Ile Glu
275 280 285

Asp Ile Thr Asp Ser Lys Leu Arg Asn Asn Asn Gly Ser Gly Thr Val 290 295 300

Val Gln Glu Ile Lys Val Pro Leu Ile Arg Thr Glu Ile
305 310 315

<210> SEQ ID NO 75
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC11243 precursor protein from an open reading frame at nucleotide position 1-951 and a translation termination codon.

<400> SEQUENCE: 75
atgaaaaaat ttgcaagttt aattcttaca agtgtgttcc ttttttcgag tacccaattt 60
gttcatgcgt catccacaga tgttcaagaa agattacggg acttggcaag agaagatgaa 120
gctggaacct ttaatgaagc atggaatact aacttcaaac ccagtgatga acaacaattc 180
tcgtatagtc caactgaagg aattgttttc ttaacaccac ctaaaaatgt tattggcgaa 240
agaagaattt cacagtataa agtaaataat gcatgggcta cattagaagg aagtccaacc 300
gaagcatcgg ggacaccttt atatgcggga aaaaacgtat tagataactc aaaaggaaca 360
atggatcaag agctgttaac acccgagttt agttatacct atacggaaag cacttcaaat 420
acaacaaccc atggattaaa attaggagtc aaaaccactg ctaccatgaa attcccgatt 480
gctcagggta gcatggaagc ttctactgaa tataactttc aaaattcttc cactgatact 540
aaaactaaac aagtatcata taaaagccca tcacaaaaaa ttaaagtacc agcaggtaaa 600
acctatagag ttttagcata cctaaatact ggatctattt caggtgaagc taacctttac 660
gcaaatgttg gggtatagc ttggagggtt tcaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcaaatc taattatgga 840
acggacttca ttttaaaaat tgaagacatc acagattcaa aattacgaaa caataacggg 900
agtggaactg tcgttcaaga gattaaagtt ccactaatta gaactgaaat atag 954

<210> SEQ ID NO 76
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC11243 precursor protein from the open reading frame as set forth in SEQ ID NO:75.

<400> SEQUENCE: 76

Met Lys Lys Phe Ala Ser Leu Ile Leu Thr Ser Val Phe Leu Phe Ser
1 5 10 15

Ser Thr Gln Phe Val His Ala Ser Ser Thr Asp Val Gln Glu Arg Leu
20 25 30

Arg Asp Leu Ala Arg Glu Asp Glu Ala Gly Thr Phe Asn Glu Ala Trp
35 40 45

Asn Thr Asn Phe Lys Pro Ser Asp Glu Gln Gln Phe Ser Tyr Ser Pro
50 55 60

Thr Glu Gly Ile Val Phe Leu Thr Pro Pro Lys Asn Val Ile Gly Glu

```
65                  70                  75                  80

Arg Arg Ile Ser Gln Tyr Lys Val Asn Asn Ala Trp Ala Thr Leu Glu
                85                  90                  95

Gly Ser Pro Thr Glu Ala Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Ser Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315


<210> SEQ ID NO 77
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained
      from a Brevibacillus laterosporus species encoding a TIC11256
      precursor protein from an open reading frame at nucleotide
      position 1-951 and a translation termination codon.

<400> SEQUENCE: 77

atgaaaaaat ttgcaagttt aattcttaca agtgtgttcc tttttcgag tacgcaattt      60

gttcatgcgt catccacaga tgttcaagaa agattacggg acttggcaag agaagatgaa    120

gctggaacct ttaatgaagc atggaatact aacttcaaac ccagtgatga acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaaatgtcgg ggacaccttt atatgcggga aaaaacgtat tagataactc aaaaggaaca    360

agcgatcaag agctgttaac acccgagttt aactatacct atacggaaag cacttcaaat    420

acaacaaccc atggattaaa attaggagtc aaaaccactg ctaccatgaa attccccgatt    480

gctcagggta gcatggaagc ttctactgaa tataactttc aaaattcttc cactgatact    540
```

-continued

```
aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg ggggtatagc ttggggggtt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

```
<210> SEQ ID NO 78
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC11256 precursor protein from the open reading frame as set
      forth in SEQ ID NO:77.

<400> SEQUENCE: 78

Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Met Ser Gly Thr Pro Leu Tyr Ala Gly Lys Asn
            100                 105                 110

Val Leu Asp Asn Ser Lys Gly Thr Ser Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270
```

```
Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 79
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4544 precursor protein from an open reading frame at nucleotide position 1-951 and a translation termination codon.

<400> SEQUENCE: 79

```
atgaaaaaat ttgcaagttt aattcttaca agtgtgttcc ttttttcgag tacgcaattt      60

gttcatgcgt catccacaga tgttcaagaa agattacggg acttggcaag agaagatgaa     120

gctggaacct ttaatgaagc atggaatact aacttcaaac ccagtgatga acaacaattc     180

tcgtatagtc caactgaagg aattgttttc ttaacaccac ctaaaaatgt tattggcgaa     240

agaagaattt cacagtataa agtaaataat gcatgggcta cattagaagg aagtccaacc     300

gaagtatcgg ggacaccttt atatgcggga aaaaacgtat tagataactc aaaaggaaca     360

atcgatcaag agctgttaac acccgagttt agttatacct atacggaaag cacttcaaat     420

acaacaactc atggattaaa agtaggagtc aaaaccactg ctaccatgaa attcccgatt     480

gctcagggta gcatggaagc ttctactgaa tataactttc aaaattcttc cactgatact     540

aaaactaaac aagtatcata taaaagccca tcacaaaaaa ttaaagtacc agcaggtaaa     600

acctatagag ttttagcata cctaaatact ggatctattt caggtgaagc taacctttac     660

gcaaatgttg ggggtatagc ttggagggtt tcaccaggtt atcccaatgg cggaggagta     720

aatataggtg ctgtacttat caaatgccaa caaaaaggat ggggagattt cagaaacttt     780

caacctagtg gaagagatgt aatcgttaaa ggccaaggta ctttcaaatc taattatgga     840

acggacttca ttttaaaaat tgaagacatc acagattcaa agttacgaaa caataacggg     900

agtggaactg tcgttcaaga gattaaagtt ccactaatta gaactgaaat atag           954
```

<210> SEQ ID NO 80
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC4544 precursor protein from the open reading frame as set forth in SEQ ID NO:79.

<400> SEQUENCE: 80

```
Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45
```

```
Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Ile Asp Gln Glu Leu Leu Thr Pro
        115                 120                 125

Glu Phe Ser Tyr Thr Tyr Thr Glu Ser Thr Ser Asn Thr Thr Thr His
    130                 135                 140

Gly Leu Lys Val Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Ile Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 81
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC4545 precursor protein from an open reading frame at nucleotide position 1-951 and a translation termination codon.

<400> SEQUENCE: 81

```
atgaaaaaat ttgcaagttt aattcttata agtgtgttcc ttttttcgag tacgcaattt      60

gttcatgcgt catccacaga tgttcaagaa agattacggg acttggcaag agaagatgaa     120

gctggaaccc ttaatgaagc atggaatact aacttcaaac ccagtgatga acaacaattc     180

tcttatagtc caactgaagg aattgttttc ttaacaccac ctaaaaatgt tattggcgaa     240

agaagaattt cacagtataa agtaaataat gcatgggcta cattagaagg aagtccaacc     300

gaagtatcgg ggacaccttt atatgcggga aaaaacgtat tagataactc aaaaggaaca     360
```

atggatcaag agctgttaac acccgagttt aactatacct atacggaaag cacttcaaat 420
acaataactc atggattaaa attaggagtc aaaaccactg ctaccatgaa attcccgatt 480
gctcagggta gcatggaagc ttctactgaa tataactttc aaaattcttc cactgatact 540
aaaactaaac aagtatcata taaaagccca tcacaaaaaa ttaaagtacc agcaggtaaa 600
acctttagag ttttagcata cctaaatact ggatctattt caggtgaagc taacctttac 660
gcaaatgttg ggggtatagc ttggggggtt ttaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcgaatc taattatgga 840
acggacttca ttttaaaaat tgaagacatc acagattcaa agttacgaaa caataacggg 900
agtggaactg tcgttcaaga gattaaagtt ccactaatta gaactgaaat atag 954

<210> SEQ ID NO 82
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC4545 precursor protein from the open reading frame as set forth in SEQ ID NO:81.

<400> SEQUENCE: 82

Met Lys Lys Phe Ala Ser Leu Ile Leu Ile Ser Val Phe Leu Phe Ser
1 5 10 15

Ser Thr Gln Phe Val His Ala Ser Ser Thr Asp Val Gln Glu Arg Leu
20 25 30

Arg Asp Leu Ala Arg Glu Asp Glu Ala Gly Thr Leu Asn Glu Ala Trp
35 40 45

Asn Thr Asn Phe Lys Pro Ser Asp Glu Gln Gln Phe Ser Tyr Ser Pro
50 55 60

Thr Glu Gly Ile Val Phe Leu Thr Pro Pro Lys Asn Val Ile Gly Glu
65 70 75 80

Arg Arg Ile Ser Gln Tyr Lys Val Asn Asn Ala Trp Ala Thr Leu Glu
85 90 95

Gly Ser Pro Thr Glu Val Ser Gly Thr Pro Leu Tyr Ala Gly Lys Asn
100 105 110

Val Leu Asp Asn Ser Lys Gly Thr Met Asp Gln Glu Leu Leu Thr Pro
115 120 125

Glu Phe Asn Tyr Thr Tyr Thr Glu Ser Thr Ser Asn Thr Ile Thr His
130 135 140

Gly Leu Lys Leu Gly Val Lys Thr Thr Ala Thr Met Lys Phe Pro Ile
145 150 155 160

Ala Gln Gly Ser Met Glu Ala Ser Thr Glu Tyr Asn Phe Gln Asn Ser
165 170 175

Ser Thr Asp Thr Lys Thr Lys Gln Val Ser Tyr Lys Ser Pro Ser Gln
180 185 190

Lys Ile Lys Val Pro Ala Gly Lys Thr Phe Arg Val Leu Ala Tyr Leu
195 200 205

Asn Thr Gly Ser Ile Ser Gly Glu Ala Asn Leu Tyr Ala Asn Val Gly
210 215 220

Gly Ile Ala Trp Gly Val Leu Pro Gly Tyr Pro Asn Gly Gly Gly Val
225 230 235 240

```
Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Glu Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315


<210> SEQ ID NO 83
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained
      from a Brevibacillus laterosporus species encoding a TIC6871
      precursor protein from an open reading frame at nucleotide
      position 1-951 and a translation termination codon.

<400> SEQUENCE: 83

atgaaaaaat ttgcaagttt aattcttaca agtgtgttcc ttttttcgag tacgcaattt      60

gttcatgcgt catccacaga tgttcaagaa agattacggg acttggcaag agaagatgaa     120

gctggaacct ttaatgaagc atggaatact aacttcaaac ccagtgatga acaacaattc     180

tcgtatagtc caactgaagg aattgttttc ttaacaccac ctaaaaatgt tattggcgaa     240

agaagaattt cacagtataa agtaaataat gcatgggcta cattagaagg aagtccaacc     300

gaagtatcgg ggacaccttt atatgcggga aaaaacgtat tagataactc aaaaggaaca     360

atcgatcaag agctgttaac acccgagttt agttatacct atacggaaag cacttcaaat     420

acaacaactc atggattaaa attaggagtc aaaaccactg ctaccatgaa attcccgatt     480

gctcagggta gcatggaagc ttctactgaa tataactttc aaaattcttc cactgatact     540

aaaactaaac aagtatcata taaaagccca tcacaaaaaa ttaaagtacc agcaggtaaa     600

acctatagag ttttagcata cctaaatact ggatctattt caggtgaagc taacctttac     660

gcaaatgttg ggggtatagc ttggagggtt tcaccaggtt atcccaatgg cggaggagta     720

aatataggtg ctgtacttac caaatgccaa caaaaaggat ggggagattt cagaaacttt     780

caacctagtg gaagagatgt aatcgttaaa ggccaaggta ctttcaaatc taattatgga     840

acggacttca ttttaaaaat tgaagacatc acagattcaa agttacgaaa caataacggg     900

agtggaactg tcgttcaaga gattaaagtt ccactaatta gaactgaaat atag           954


<210> SEQ ID NO 84
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC6871 precursor protein from the open reading frame as set forth
      in SEQ ID NO:83.

<400> SEQUENCE: 84

Met Lys Lys Phe Ala Ser Leu Ile Leu Thr Ser Val Phe Leu Phe Ser
1               5                   10                  15
```

-continued

```
Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Ile Asp Gln Glu Leu Leu Thr Pro
        115                 120                 125

Glu Phe Ser Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 85
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7429 precursor protein from an open reading frame at nucleotide position 1-951 and a translation termination codon.

<400> SEQUENCE: 85

```
atgaaaaaat ttgcaagttt aattcttata agtgtgttcc ttttttcgag tacgcaattt      60

gttcatgcgt catccacaga tgttcaagaa cgattacggg acttggcaag agaagatgaa     120

gctggaaccc ttaatgaagc atggaatact aacttcaaac ccagtgatga acaacaattc     180

tcttatagtc caactgaagg aattgttttc ttaacaccac ctaaaaatgt tattggcgaa     240
```

```
agaagaattt cacagtataa agtaaataat gcatgggcta cattagaagg aagtccaacc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaacaactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcacatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

```
<210> SEQ ID NO 86
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC7429 precursor protein from the open reading frame as set forth
      in SEQ ID NO:85.

<400> SEQUENCE: 86

Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
```

-continued

```
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Thr Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 87
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7497 precursor protein from an open reading frame at nucleotide position 1-951 and a translation termination codon.

<400> SEQUENCE: 87

```
atgaaaaaat ttgcaagttt aattcttaca agtgtgttcc ttttttcgag tacgcaattt     60

gttcatgcgt catccacaga tgttcaagaa agattacggg acttggcaag agaagatgaa    120

gctggaacct ttaatgaagc atggaatact aacttcaaac ccagtgatca acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaacaactc atggattaaa agtaggagtc aaaaccactg ctaccatgaa attccccgatt   480

gctcagggta gcatggaagc ttctactgaa tataactttc aaaattcttc cactgatact    540

aaaactaaac aagtatcata taaaagccca tcacaaaaga ttaaagtacc agcaggtaaa    600

acctttagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 88
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7497 precursor protein from the open reading frame as set forth in SEQ ID NO:89.

<400> SEQUENCE: 88

```
Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Gln Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Val Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 89
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7511 precursor protein from an open reading frame at nucleotide position 1-951 and a translation termination codon.

<400> SEQUENCE: 89

```
atgaaaaaat ttgcaagttt aattcttata agtgtgttcc ttttttcgag tacgcaattt     60
```

-continued

```
gttcatgcgt catccacaga tgttcaagaa agattacggg acttggcaag agaagatgaa    120

gctggaacct ttaatgaagc atggaatact aacttcaaac ccagtgatca acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgtggga aaaaacgtat tagataactc aaaaggaaca    360

agcgatcaag agctgttaac acccgagttt aactatacct atacggaaag cacttcaaat    420

acaacaactc atggattaaa agtaggagtc aaaaccactg ctaccatgaa attccccgatt    480

gctcagggta gcatggaagc ttctactgaa tataactttc aagattcttc cactgatact    540

acaactaaaa cagtatcata taaaagccca tcacaaaaga ttaaagtacc agcaggtaaa    600

acctttagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta cattcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 90
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7511 precursor protein from the open reading frame as set forth in SEQ ID NO:91.

<400> SEQUENCE: 90

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Gln Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Val Gly Lys Asn
            100                 105                 110

Val Leu Asp Asn Ser Lys Gly Thr Ser Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Val Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asp Ser
                165                 170                 175

Ser Thr Asp Thr Thr Thr Lys Thr Val Ser Tyr Lys Ser Pro Ser Gln
            180                 185                 190
```

```
Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 91
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7513 precursor protein from an open reading frame at nucleotide position 1-951 and a translation termination codon.

<400> SEQUENCE: 91

```
atgaaaaaat ttgcaagttt aattcttata agtgtgttcc ttttttcgag tacgcaattt     60

gttcatgcgt catccacaga tgttcaagaa agattacggg acttggcaag agaagatgaa    120

gctggaacct ttaatgaagc atggaatact aacttcaaac ccagtgatga acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagcatcgg ggacaccttt atatgcggga aaaaacgtat tagataactc aaaaggaaca    360

atggatcaag agctgttaac acccgagttt aactatacct atacggaaag cacttcaaat    420

acaacaaccc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctatagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 92
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC7513 precursor protein from the open reading frame as set forth
      in SEQ ID NO:93.

<400> SEQUENCE: 92

Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Ala Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315

<210> SEQ ID NO 93
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained
      from a Brevibacillus laterosporus species encoding a TIC7518
      precursor protein from an open reading frame at nucleotide
      position 1-951 and a translation termination codon.

<400> SEQUENCE: 93
atgaaaaaat ttgcaagttt aattcttata agtgtgttcc ttttttcgag tacgcaattt 60
gttcatgcgt catccacaga tgttcaagaa agattacggg acttggcaag agaaaatgaa 120
gctggaaccc ttaatgaagc atggaatact aacttcaaac ccagtgatga acaacaattc 180
tcttatagtc caactgaagg aattgttttc ttaacaccac ctaaaaatgt tattggcgaa 240
agaagaattt cacagtataa agtaaataat gcatgggcta cattagaagg aagtccaacc 300
gaagtatcgg ggacaccttt atatgcggga aaaaacgtat tagataactc aaaaggaaca 360
atggatcaag agctgttaac acccgagttt aactatacct atacggaaag cacttcaaat 420
acaataactc atggattaaa attaggagtc aaaaccactg ctaccatgaa attcccgatt 480
gctcagggta gcatggaagc ttctactgaa tataactttc aaaattcttc cactgatact 540
aaaactaaac aagtatcata taaaagccca tcacaaaaaa ttaaagtacc agcaggtaaa 600
acctttagag ttttagcata cctaaatact ggatctattt caggtgaagc taacctttac 660
gcaaatgttg gggtatagc ttgggggggtt ttaccaggtt atcccaatgg cggaggagta 720
aatataggtg ctgtacttac caaatgccaa caaaaaggat ggggagattt cagaaacttt 780
caacctagtg gaagagatgt aatcgttaaa ggccaaggta ctttcgaatc taattatgga 840
acggacttca ttttaaaaat tgaagacatc acagattcaa agttacgaaa caataacggg 900
agtggaactg tcgttcaaga gattaaagtt ccactaatta gaactgaaat atag 954

<210> SEQ ID NO 94
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7518 precursor protein from the open reading frame as set forth in SEQ ID NO:95.

<400> SEQUENCE: 94

Met Lys Lys Phe Ala Ser Leu Ile Leu Ile Ser Val Phe Leu Phe Ser
1 5 10 15

Ser Thr Gln Phe Val His Ala Ser Ser Thr Asp Val Gln Glu Arg Leu
20 25 30

Arg Asp Leu Ala Arg Glu Asn Glu Ala Gly Thr Leu Asn Glu Ala Trp
35 40 45

Asn Thr Asn Phe Lys Pro Ser Asp Glu Gln Gln Phe Ser Tyr Ser Pro
50 55 60

Thr Glu Gly Ile Val Phe Leu Thr Pro Pro Lys Asn Val Ile Gly Glu
65 70 75 80

Arg Arg Ile Ser Gln Tyr Lys Val Asn Asn Ala Trp Ala Thr Leu Glu
85 90 95

Gly Ser Pro Thr Glu Val Ser Gly Thr Pro Leu Tyr Ala Gly Lys Asn
100 105 110

Val Leu Asp Asn Ser Lys Gly Thr Met Asp Gln Glu Leu Leu Thr Pro
115 120 125

Glu Phe Asn Tyr Thr Tyr Thr Glu Ser Thr Ser Asn Thr Ile Thr His
130 135 140

Gly Leu Lys Leu Gly Val Lys Thr Thr Ala Thr Met Lys Phe Pro Ile
145 150 155 160

```
Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Glu Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 95
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7524 precursor protein from an open reading frame at nucleotide position 1-951 and a translation termination codon.

<400> SEQUENCE: 95

```
atgaaaaaat ttgcaagttt aattcttaca agtgtgttcc ttttttcgag tacccaaatt     60
gttcatgcgt catccacaga tgttcaagaa agattacggg acttggcaag agaagatgaa    120
gctggaacct ttaatgaagc atggaatact aacttcaaac ccagtgatga acaacaattc    180
tcttatagtc caactgaagg aattgttttc ttaacaccac ctaaaaatgt tattggcgaa    240
agaagaattt cacagtataa agtaaataat gcatgggcta cattagaagg aagtccaacc    300
gaagcatcgg ggacaccttt atatgcggga aaaaacgtat tagataactc aaaaggaaca    360
atggatcaag agctgttaac acccgagttt aactatacct atacggaaag cacttcaaat    420
acaacaaccc atggattaaa attaggagtc aaaaccactg ctaccatgaa attcccgatt    480
gctcagggta gcatggaagc ttctactgaa tataactttc aaaattcttc cactgatact    540
aaaactaaac aagtatcata taaaagccca tcacaaaaaa ttaaagtacc agcaggtaaa    600
acctatagag ttttagcata cctaaatact ggatctattt caggtgaagc taacctttac    660
gcaaatgttg ggggtatagc ttggagggtt tcaccaggtt atcccaatgg cggaggagta    720
aatataggtg ctgtacttac caaatgccaa caaaaaggat ggggagattt cagaaacttt    780
caacctagtg gaagagatgt aatcgttaaa ggccaaggta ctttcgaatc taattatgga    840
acggacttca ttttaaaaat tgaagacatc acagattcaa agttacgaaa caataacggg    900
agtggaactg tcgttcaaga gattaaagtt ccactaatta gaactgaaat atag          954
```

<210> SEQ ID NO 96

```
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the
      TIC7524 precursor protein from the open reading frame as set forth
      in SEQ ID NO:97.

<400> SEQUENCE: 96

Met Lys Lys Phe Ala Ser Leu Ile Leu Thr Ser Val Phe Leu Phe Ser
1               5                   10                  15

Ser Thr Gln Ile Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Ala Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Tyr Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Glu Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315


<210> SEQ ID NO 97
<211> LENGTH: 954
<212> TYPE: DNA
<213> ORGANISM: Brevibacillus laterosporus
<220> FEATURE:
<221> NAME/KEY: misc_feature
```

<222> LOCATION: (1)..(954)
<223> OTHER INFORMATION: A recombinant polynucleotide sequence obtained from a Brevibacillus laterosporus species encoding a TIC7526 precursor protein from an open reading frame at nucleotide position 1-951 and a translation termination codon.

<400> SEQUENCE: 97

```
atgaaaaaat ttgcaagttt aattcttata agtgtgttcc ttttttcgag tacgcaattt     60

gttcatgcgt catccacaga tgttcaagaa agattacggg acttagcaag agaaaatgaa    120

gctggaaccc ttaatgaagc atggaatact aacttcaaac ccagtgatga acaacaattc    180

tcttatagtc caactgaagg tattgttttc ttaacaccac ctaaaaatgt tattggcgaa    240

agaagaattt cacagtataa agtaaataat gcatgggcta cattagaagg aagtccaatc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaataactc atggattaaa attaggagtc aaaaccactg ctaccatgaa attccccgatt    480

gctcagggta gcatggaagc ttctactgaa tataactttc aaaattcttc cactgatact    540

aaaactaaac aagtatcata taaaagccca tcacaaaaaa ttaaagtacc agcaggtaaa    600

acctttagag ttttagcata cctaaatact ggatctattt caggtgaagc taacctttac    660

gcaaatgttg gggtatagc ttggggggtt ttaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcgaatc taattatgga    840

acggacttca ttttaaaaat tgaagacatc acagattcaa agttacgaaa caataacggg    900

agtggaactg tcgttcaaga gattaaagtt ccactaatta gaactgaaat atag          954
```

<210> SEQ ID NO 98
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7526 precursor protein from the open reading frame as set forth in SEQ ID NO:99.

<400> SEQUENCE: 98

```
Met Lys Lys Phe Ala Ser Leu Ile Leu Ile Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asn Glu Ala Gly Thr Leu Asn Glu Ala Trp
        35                  40                  45

Asn Thr Asn Phe Lys Pro Ser Asp Glu Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Ile Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Ile Thr His
```

-continued

```
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Gly Val Leu Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Glu Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 99
<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7528 precursor protein from an open reading frame at nucleotide position 1-951 and a translation termination codon.

<400> SEQUENCE: 99

```
atgaaaaaat ttgcaagttt aattcttaca agtgtgttcc tttttcgag tacgcaattt     60

gttcatgcgt catccacaga tgttcaagaa agattacggg acttggcaag agaagatgaa    120

gctggaacct ttaatgaagc atggaatact aacttcaaac ccagtgatca acaacaattc    180

tcttatagtc caactgaagg aattgttttc ttaacaccac ctaaaaatgt tattggcgaa    240

agaagaattt cacagtataa agtaaataat gcatgggcta cattagaagg aagtccaacc    300

gaagtatcgg ggacaccttt atatgcggga aaaaacgtat tagataactc aaaaggaaca    360

atggatcaag agctgttaac acccgagttt aactatacct atacggaaag cacttcaaat    420

acaacaactc atggattaaa attaggagtc aaaaccactg ctaccatgaa attcccgatt    480

gctcagggta gcatggaagc ttctactgaa tataactttc aaaattcttc cactgatact    540

aaaactaaac aagtatcata taaaagccca tcacaaaaga ttaaagtacc agcaggtaaa    600

acctttagag ttttagcata cctaaatact ggatctattt caggtgaagc taacctttac    660

gcaaatgttg ggggtatagc ttggagggtt tcaccaggtt atcccaatgg cggaggagta    720

aatataggtg ctgtacttac caaatgccaa caaaaaggat ggggagattt cagaaacttt    780

caacctagtg gaagagatgt aatcgttaaa ggccaaggta ctttcaaatc taattatgga    840

acggacttca ttttaaaaat tgaagacatc acagattcaa agttacgaaa caataacggg    900
```

agtggaactg tcgttcaaga gattaaagtt ccactaatta gaactgaaat atag 954

<210> SEQ ID NO 100
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7528 precursor protein from the open reading frame as set forth in SEQ ID NO:101.

<400> SEQUENCE: 100

```
Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Gln Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Val Ser Gly Thr Pro Leu Tyr Ala Gly Lys Asn
            100                 105                 110

Val Leu Asp Asn Ser Lys Gly Thr Met Asp Gln Glu Leu Leu Thr Pro
        115                 120                 125

Glu Phe Asn Tyr Thr Tyr Thr Glu Ser Thr Ser Asn Thr Thr Thr His
    130                 135                 140

Gly Leu Lys Leu Gly Val Lys Thr Thr Ala Thr Met Lys Phe Pro Ile
145                 150                 155                 160

Ala Gln Gly Ser Met Glu Ala Ser Thr Glu Tyr Asn Phe Gln Asn Ser
                165                 170                 175

Ser Thr Asp Thr Lys Thr Lys Gln Val Ser Tyr Lys Ser Pro Ser Gln
            180                 185                 190

Lys Ile Lys Val Pro Ala Gly Lys Thr Phe Arg Val Leu Ala Tyr Leu
        195                 200                 205

Asn Thr Gly Ser Ile Ser Gly Glu Ala Asn Leu Tyr Ala Asn Val Gly
    210                 215                 220

Gly Ile Ala Trp Arg Val Ser Pro Gly Tyr Pro Asn Gly Gly Gly Val
225                 230                 235                 240

Asn Ile Gly Ala Val Leu Thr Lys Cys Gln Gln Lys Gly Trp Gly Asp
                245                 250                 255

Phe Arg Asn Phe Gln Pro Ser Gly Arg Asp Val Ile Val Lys Gly Gln
            260                 265                 270

Gly Thr Phe Lys Ser Asn Tyr Gly Thr Asp Phe Ile Leu Lys Ile Glu
        275                 280                 285

Asp Ile Thr Asp Ser Lys Leu Arg Asn Asn Asn Gly Ser Gly Thr Val
    290                 295                 300

Val Gln Glu Ile Lys Val Pro Leu Ile Arg Thr Glu Ile
305                 310                 315
```

<210> SEQ ID NO 101

<211> LENGTH: 954
<212> TYPE: DNA
<213> ORGANISM: Brevibacillus laterosporus
<220> FEATURE:
<221> NAME/KEY: misc_feature
<222> LOCATION: (1)..(954)
<223> OTHER INFORMATION: A recombinant polynucleotide sequence obtained from a Brevibacillus laterosporus species encoding a TIC7535 precursor protein from an open reading frame at nucleotide position 1-951 and a translation termination codon.

<400> SEQUENCE: 101

```
atgaaaaaat ttgcaagttt aattcttaca agtgtgttcc ttttttcgag tacgcaattt      60

gttcatgcgt catccacaga tgttcaagaa agattacggg acttggcaag agaagatgaa     120

gctggaacct ttaatgaagc atggaatact aacttcaaac ccagtgatca acaacaattc     180

tcttatagtc caactgaagg aattgttttc ttaacaccac ctaaaaatgt tattggcgaa     240

agaagaattt cacagtataa agtaaataat gcatgggcta cattagaagg aagtccaacc     300

gaagcatcgg ggacaccttt atatgcggga aaaaacgtat tagataactc aaaaggaaca     360

atggatcaag agctgttaac acccgagttt agttatacct atacggaaag cacttcaaat     420

acaacaaccc atggattaaa attaggagtc aaaaccactg ctaccatgaa attccccgatt    480

gctcagggta gcatggaagc ttctactgaa tataactttc aaaattcttc cactgatact     540

aaaactaaac aagtatcata taaaagccca tcacaaaaaa ttaaagtacc agcaggtaaa     600

acctatagag ttttagcata cctaaatact ggatctattt caggtgaagc taacctttac     660

gcaaatgttg gggtatagc ttggagggtt tcaccaggtt atcccaatgg cggaggagta     720

aatataggtg ctgtacttac caaatgccaa caaaaaggat ggggagattt cagaaacttt     780

caacctagtg gaagagatgt aatcgttaaa ggccaaggta ctttcaaatc taattatgga     840

acggacttca ttttaaaaat tgaagacatc acagattcaa agttacgaaa caataacggg     900

agtggaactg tcgttcaaga gattaaagtt ccactaatta gaactgaaat atag           954
```

<210> SEQ ID NO 102
<211> LENGTH: 317
<212> TYPE: PRT
<213> ORGANISM: Brevibacillus laterosporus
<220> FEATURE:
<221> NAME/KEY: MISC_FEATURE
<222> LOCATION: (1)..(317)
<223> OTHER INFORMATION: The amino acid sequence translation of the TIC7535 precursor protein from the open reading frame as set forth in SEQ ID NO:103.

<400> SEQUENCE: 102

```
Met Lys Lys Phe Ala Ser Leu Ile Leu Thr Ser Val Phe Leu Phe Ser
1               5                   10                  15

Ser Thr Gln Phe Val His Ala Ser Ser Thr Asp Val Gln Glu Arg Leu
            20                  25                  30

Arg Asp Leu Ala Arg Glu Asp Glu Ala Gly Thr Phe Asn Glu Ala Trp
        35                  40                  45

Asn Thr Asn Phe Lys Pro Ser Asp Gln Gln Gln Phe Ser Tyr Ser Pro
    50                  55                  60

Thr Glu Gly Ile Val Phe Leu Thr Pro Pro Lys Asn Val Ile Gly Glu
65                  70                  75                  80

Arg Arg Ile Ser Gln Tyr Lys Val Asn Asn Ala Trp Ala Thr Leu Glu
                85                  90                  95

Gly Ser Pro Thr Glu Ala Ser Gly Thr Pro Leu Tyr Ala Gly Lys Asn
            100                 105                 110
```

-continued

Val Leu Asp Asn Ser Lys Gly Thr Met Asp Gln Glu Leu Leu Thr Pro
115 120 125

Glu Phe Ser Tyr Thr Tyr Thr Glu Ser Thr Ser Asn Thr Thr Thr His
130 135 140

Gly Leu Lys Leu Gly Val Lys Thr Thr Ala Thr Met Lys Phe Pro Ile
145 150 155 160

Ala Gln Gly Ser Met Glu Ala Ser Thr Glu Tyr Asn Phe Gln Asn Ser
165 170 175

Ser Thr Asp Thr Lys Thr Lys Gln Val Ser Tyr Lys Ser Pro Ser Gln
180 185 190

Lys Ile Lys Val Pro Ala Gly Lys Thr Tyr Arg Val Leu Ala Tyr Leu
195 200 205

Asn Thr Gly Ser Ile Ser Gly Glu Ala Asn Leu Tyr Ala Asn Val Gly
210 215 220

Gly Ile Ala Trp Arg Val Ser Pro Gly Tyr Pro Asn Gly Gly Gly Val
225 230 235 240

Asn Ile Gly Ala Val Leu Thr Lys Cys Gln Gln Lys Gly Trp Gly Asp
245 250 255

Phe Arg Asn Phe Gln Pro Ser Gly Arg Asp Val Ile Val Lys Gly Gln
260 265 270

Gly Thr Phe Lys Ser Asn Tyr Gly Thr Asp Phe Ile Leu Lys Ile Glu
275 280 285

Asp Ile Thr Asp Ser Lys Leu Arg Asn Asn Asn Gly Ser Gly Thr Val
290 295 300

Val Gln Glu Ile Lys Val Pro Leu Ile Arg Thr Glu Ile
305 310 315

<210> SEQ ID NO 103
<211> LENGTH: 888
<212> TYPE: DNA
<213> ORGANISM: Artificial
<220> FEATURE:
<223> OTHER INFORMATION: A synthetic nucleotide sequence encoding a mature TIC11239 protein, mTIC11239 for expression in bacteria.

<400> SEQUENCE: 103
atgtcatcca cagatgttca agaaagatta cgggacttgg caagagaaga tgaagctgga 60
acctttaatg aagcatggaa tactaacttc aaacccagtg atgaacaaca attctcttat 120
agtccaactg aaggaattgt tttcttaaca ccacctaaaa atgttattgg cgaaagaaga 180
atttcacagt ataaagtaaa taatgcatgg gctacattag aaggaagtcc aaccgaagta 240
tcggggacac ctttatatgc gggaaaaaac gtattagata actcaaaagg aacaatggat 300
caagagctgt taacacccga gtttaactat acctatacgg aaagcacttc aaatacaata 360
actcatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aaaattaaag taccagcagg taaaacctat 540
agagttttag catacctaaa tactggatct atttcaggtg aagctaacct ttacgcaaat 600
gttgggggta tagcttggag ggtttcacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttcg aatctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 104
<211> LENGTH: 295
<212> TYPE: PRT
<213> ORGANISM: Artificial
<220> FEATURE:
<223> OTHER INFORMATION: An amino acid sequence of a mature TIC11239 protein, mTIC11239.

<400> SEQUENCE: 104

```
Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Ile Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Glu Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 105
<211> LENGTH: 888
<212> TYPE: DNA
<213> ORGANISM: Artificial
<220> FEATURE:
<223> OTHER INFORMATION: A synthetic nucleotide sequence encoding a mature TIC11243 protein, mTIC11243 for expression in bacteria.

<400> SEQUENCE: 105

```
atgtcatcca cagatgttca agaaagatta cgggacttgg caagagaaga tgaagctgga     60
acctttaatg aagcatggaa tactaacttc aaacccagtg atgaacaaca attctcgtat    120
agtccaactg aaggaattgt tttcttaaca ccacctaaaa atgttattgg cgaaagaaga    180
atttcacagt ataaagtaaa taatgcatgg gctacattag aaggaagtcc aaccgaagca    240
tcggggacac ctttatatgc gggaaaaaac gtattagata actcaaaagg aacaatggat    300
caagagctgt taacacccga gtttagttat acctatacgg aaagcacttc aaatacaaca    360
acccatggat taaaattagg agtcaaaacc actgctacca tgaaattccc gattgctcag    420
ggtagcatgg aagcttctac tgaatataac tttcaaaatt cttccactga tactaaaact    480
aaacaagtat catataaaag cccatcacaa aaaattaaag taccagcagg taaaacctat    540
agagttttag catacctaaa tactggatct atttcaggtg aagctaacct ttacgcaaat    600
gttgggggta tagcttggag ggtttcacca ggttatccca atggcggagg agtaaatata    660
ggtgctgtac ttaccaaatg ccaacaaaaa ggatggggag atttcagaaa ctttcaacct    720
agtggaagag atgtaatcgt taaaggccaa ggtactttca aatctaatta tggaacggac    780
ttcattttaa aaattgaaga catcacagat tcaaaattac gaaacaataa cgggagtgga    840
actgtcgttc aagagattaa agttccacta attagaactg aaatatag                 888
```

<210> SEQ ID NO 106
<211> LENGTH: 295
<212> TYPE: PRT
<213> ORGANISM: Artificial
<220> FEATURE:
<223> OTHER INFORMATION: An amino acid sequence of a mature TIC11243 protein, mTIC11243.

<400> SEQUENCE: 106

```
Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Ala
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Ser Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190
```

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295

<210> SEQ ID NO 107
<211> LENGTH: 888
<212> TYPE: DNA
<213> ORGANISM: Artificial
<220> FEATURE:
<223> OTHER INFORMATION: A synthetic nucleotide sequence encoding a mature TIC11256 protein, mTIC11256 for expression in bacteria.

<400> SEQUENCE: 107
atgtcatcca cagatgttca agaaagatta cgggacttgg caagagaaga tgaagctgga 60
acctttaatg aagcatggaa tactaacttc aaacccagtg atgaacaaca attctcttat 120
agtccaactg aaggaattgt tttcttaaca ccacctaaaa atgttattgg cgaaagaaga 180
atttcacagt ataaagtaaa taatgcatgg gctacattag aaggaagtcc aaccgaaatg 240
tcggggacac ctttatatgc gggaaaaaac gtattagata actcaaaagg aacaagcgat 300
caagagctgt taacacccga gtttaactat acctatacgg aaagcacttc aaatacaaca 360
acccatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aaaattaaag taccagcagg taaaacctat 540
agagttttag catacctaaa tactggatct atttcaggtg aagctaacct ttacgcaaat 600
gttgggggta tagcttgggg ggttttacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttca aatctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 108
<211> LENGTH: 295
<212> TYPE: PRT
<213> ORGANISM: Artificial
<220> FEATURE:
<223> OTHER INFORMATION: An amino acid sequence of a mature TIC11256 protein, mTIC11256.

<400> SEQUENCE: 108

Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

```
Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Met
65                  70                  75                  80

Ser Gly Thr Pro Leu Tyr Ala Gly Lys Asn Val Leu Asp Asn Ser Lys
                85                  90                  95

Gly Thr Ser Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Gly Val
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 109
<211> LENGTH: 888
<212> TYPE: DNA
<213> ORGANISM: Artificial
<220> FEATURE:
<223> OTHER INFORMATION: A synthetic nucleotide sequence encoding a mature TIC4544 protein, mTIC4544 for expression in bacteria.

<400> SEQUENCE: 109

```
atgtcatcca cagatgttca agaaagatta cgggacttgg caagagaaga tgaagctgga     60

acctttaatg aagcatggaa tactaacttc aaacccagtg atgaacaaca attctcgtat    120

agtccaactg aaggaattgt tttcttaaca ccacctaaaa atgttattgg cgaaagaaga    180

atttcacagt ataaagtaaa taatgcatgg gctacattag aaggaagtcc aaccgaagta    240

tcggggacac ctttatatgc gggaaaaaac gtattagata actcaaaagg aacaatcgat    300

caagagctgt taacacccga gtttagttat acctatacgg aaagcacttc aaatacaaca    360

actcatggat taaaagtagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540
```

```
agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttatcaaatg ccaacaaaaa ggatggggag atttcagaaa ctttcaacct    720

agtggaagag atgtaatcgt taaaggccaa ggtactttca aatctaatta tggaacggac    780

ttcattttaa aaattgaaga catcacagat tcaaagttac gaaacaataa cgggagtgga    840

actgtcgttc aagagattaa agttccacta attagaactg aaatatag                 888


<210> SEQ ID NO 110
<211> LENGTH: 295
<212> TYPE: PRT
<213> ORGANISM: Artificial
<220> FEATURE:
<223> OTHER INFORMATION: An amino acid sequence of a mature TIC4544
      protein, mTIC4544.

<400> SEQUENCE: 110

Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Ile Asp Gln Glu Leu Leu Thr Pro Glu Phe Ser Tyr Thr Tyr
            100                 105                 110

Thr Glu Ser Thr Ser Asn Thr Thr Thr His Gly Leu Lys Val Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Ile Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
```

290 295

<210> SEQ ID NO 111
<211> LENGTH: 888
<212> TYPE: DNA
<213> ORGANISM: Artificial
<220> FEATURE:
<223> OTHER INFORMATION: A synthetic nucleotide sequence encoding a mature TIC4545 protein, mTIC4545 for expression in bacteria.

<400> SEQUENCE: 111
atgtcatcca cagatgttca agaaagatta cgggacttgg caagagaaga tgaagctgga 60
acccttaatg aagcatggaa tactaacttc aaacccagtg atgaacaaca attctcttat 120
agtccaactg aaggaattgt tttcttaaca ccacctaaaa atgttattgg cgaaagaaga 180
atttcacagt ataaagtaaa taatgcatgg gctacattag aaggaagtcc aaccgaagta 240
tcggggacac ctttatatgc gggaaaaaac gtattagata actcaaaagg aacaatggat 300
caagagctgt taacacccga gtttaactat acctatacgg aaagcacttc aaatacaata 360
actcatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aaaattaaag taccagcagg taaaaccttt 540
agagttttag catacctaaa tactggatct atttcaggtg aagctaacct ttacgcaaat 600
gttgggggta tagcttgggg ggttttacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttcg aatctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 112
<211> LENGTH: 295
<212> TYPE: PRT
<213> ORGANISM: Artificial
<220> FEATURE:
<223> OTHER INFORMATION: An amino acid sequence of a mature TIC4545 protein, mTIC4545.

<400> SEQUENCE: 112

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Val
65 70 75 80

Ser Gly Thr Pro Leu Tyr Ala Gly Lys Asn Val Leu Asp Asn Ser Lys
85 90 95

Gly Thr Ile Asp Gln Glu Leu Leu Thr Pro Glu Phe Ser Tyr Thr Tyr
100 105 110

Thr Glu Ser Thr Ser Asn Thr Thr Thr His Gly Leu Lys Val Gly Val
115 120 125

Lys Thr Thr Ala Thr Met Lys Phe Pro Ile Ala Gln Gly Ser Met Glu

```
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Ile Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295


<210> SEQ ID NO 113
<211> LENGTH: 888
<212> TYPE: DNA
<213> ORGANISM: Artificial
<220> FEATURE:
<223> OTHER INFORMATION: A synthetic nucleotide sequence encoding a
      mature TIC6871 protein, mTIC6871 for expression in bacteria.

<400> SEQUENCE: 113

atgtcatcca cagatgttca agaaagatta cgggacttgg caagagaaga tgaagctgga      60

acctttaatg aagcatggaa tactaacttc aaacccagtg atgaacaaca attctcgtat     120

agtccaactg aaggaattgt tttcttaaca ccacctaaaa atgttattgg cgaaagaaga     180

atttcacagt ataaagtaaa taatgcatgg gctacattag aaggaagtcc aaccgaagta     240

tcggggacac ctttatatgc gggaaaaaac gtattagata actcaaaagg aacaatcgat     300

caagagctgt taacacccga gtttagttat acctatacgg aaagcacttc aaatacaaca     360

actcatggat taaaattagg agtcaaaacc actgctacca tgaaattccc gattgctcag     420

ggtagcatgg aagcttctac tgaatataac tttcaaaatt cttccactga tactaaaact     480

aaacaagtat catataaaag cccatcacaa aaaattaaag taccagcagg taaaacctat     540

agagttttag catacctaaa tactggatct atttcaggtg aagctaacct ttacgcaaat     600

gttgggggta tagcttggag ggtttcacca ggttatccca atggcggagg agtaaatata     660

ggtgctgtac ttaccaaatg ccaacaaaaa ggatggggag atttcagaaa ctttcaacct     720

agtggaagag atgtaatcgt taaaggccaa ggtactttca aatctaatta tggaacggac     780

ttcattttaa aaattgaaga catcacagat tcaaagttac gaaacaataa cgggagtgga     840

actgtcgttc aagagattaa agttccacta attagaactg aaatatag                  888


<210> SEQ ID NO 114
<211> LENGTH: 295
<212> TYPE: PRT
<213> ORGANISM: Artificial
<220> FEATURE:
```

<223> OTHER INFORMATION: An amino acid sequence of a mature TIC6871 protein, mTIC6871.

<400> SEQUENCE: 114

```
Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Ile Asp Gln Glu Leu Leu Thr Pro Glu Phe Ser Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 115
<211> LENGTH: 888
<212> TYPE: DNA
<213> ORGANISM: Artificial
<220> FEATURE:
<223> OTHER INFORMATION: A synthetic nucleotide sequence encoding a mature TIC7429 protein, mTIC7429 for expression in bacteria.

<400> SEQUENCE: 115

```
atgtcatcca cagatgttca agaacgatta cgggacttgg caagagaaga tgaagctgga      60

acccttaatg aagcatggaa tactaacttc aaacccagtg atgaacaaca attctcttat     120

agtccaactg aaggaattgt tttcttaaca ccacctaaaa atgttattgg cgaaagaaga     180
```

```
atttcacagt ataaagtaaa taatgcatgg gctacattag aaggaagtcc aaccgaagta    240

tcggggacac ctttatatgc gggaaaaaac gtattagata actcaaaagg aacaatggat    300

caagagctgt taacacccga gtttaactat acctatacgg aaagcacttc aaatacaaca    360

actcatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttca catctaatta tggaacggac    780

ttcattttaa aaattgaaga catcacagat tcaaagttac gaaacaataa cgggagtgga    840

actgtcgttc aagagattaa agttccacta attagaactg aaatatag                 888
```

<210> SEQ ID NO 116
<211> LENGTH: 295
<212> TYPE: PRT
<213> ORGANISM: Artificial
<220> FEATURE:
<223> OTHER INFORMATION: An amino acid sequence of a mature TIC7429 protein, mTIC7429.

<400> SEQUENCE: 116

```
Met Ser Ser Thr Asp Val Gln Glu Arg Leu Arg Asp Leu Ala Arg Glu
1               5                   10                  15

Asp Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240
```

```
Ser Gly Arg Asp Val Ile Val Lys Gly Gln Gly Thr Phe Thr Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295


<210> SEQ ID NO 117
<211> LENGTH: 888
<212> TYPE: DNA
<213> ORGANISM: Artificial
<220> FEATURE:
<223> OTHER INFORMATION: A synthetic nucleotide sequence encoding a
      mature TIC7497 protein, mTIC7497 for expression in bacteria.

<400> SEQUENCE: 117

atgtcatcca cagatgttca agaaagatta cgggacttgg caagagaaga tgaagctgga      60

acctttaatg aagcatggaa tactaacttc aaacccagtg atcaacaaca attctcttat     120

agtccaactg aaggaattgt tttcttaaca ccacctaaaa atgttattgg cgaaagaaga     180

atttcacagt ataaagtaaa taatgcatgg gctacattag aaggaagtcc aaccgaagta     240

tcggggacac ctttatatgc gggaaaaaac gtattagata actcaaaagg aacaatggat     300

caagagctgt taacacccga gtttaactat acctatacgg aaagcacttc aaatacaaca     360

actcatggat taaaagtagg agtcaaaacc actgctacca tgaaattccc gattgctcag     420

ggtagcatgg aagcttctac tgaatataac tttcaaaatt cttccactga tactaaaact     480

aaacaagtat catataaaag cccatcacaa aagattaaag taccagcagg taaaaccttt     540

agagttttag catacctaaa tactggatct atttcaggtg aagctaacct ttacgcaaat     600

gttgggggta tagcttggag ggtttcacca ggttatccca atggcggagg agtaaatata     660

ggtgctgtac ttaccaaatg ccaacaaaaa ggatggggag atttcagaaa ctttcaacct     720

agtggaagag atgtaatcgt taaaggccaa ggtactttca aatctaatta tggaacggac     780

ttcattttaa aaattgaaga catcacagat tcaaagttac gaaacaataa cgggagtgga     840

actgtcgttc aagagattaa agttccacta attagaactg aaatatag                  888


<210> SEQ ID NO 118
<211> LENGTH: 295
<212> TYPE: PRT
<213> ORGANISM: Artificial
<220> FEATURE:
<223> OTHER INFORMATION: An amino acid sequence of a mature TIC7497
      protein, mTIC7497.

<400> SEQUENCE: 118

Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Gln Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80
```

```
Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Thr Thr His Gly Leu Lys Val Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 119
<211> LENGTH: 888
<212> TYPE: DNA
<213> ORGANISM: Artificial
<220> FEATURE:
<223> OTHER INFORMATION: A synthetic nucleotide sequence encoding a mature TIC7511 protein, mTIC7511 for expression in bacteria.

<400> SEQUENCE: 119

```
atgtcatcca cagatgttca agaaagatta cgggacttgg caagagaaga tgaagctgga      60

acctttaatg aagcatggaa tactaacttc aaacccagtg atcaacaaca attctcttat     120

agtccaactg aaggaattgt tttcttaaca ccacctaaaa atgttattgg cgaaagaaga     180

atttcacagt ataaagtaaa taatgcatgg gctacattag aaggaagtcc aaccgaagta     240

tcggggacac ctttatatgt gggaaaaaac gtattagata actcaaaagg aacaagcgat     300

caagagctgt taacacccga gtttaactat acctatacgg aaagcacttc aaatacaaca     360

actcatggat taaaagtagg agtcaaaacc actgctacca tgaaattccc gattgctcag     420

ggtagcatgg aagcttctac tgaatataac tttcaagatt cttccactga tactacaact     480

aaaacagtat catataaaag cccatcacaa aagattaaag taccagcagg taaaaccttt     540

agagttttag catacctaaa tactggatct atttcaggtg aagctaacct ttacgcaaat     600

gttgggggta tagcttggag ggtttcacca ggttatccca atggcggagg agtaaatata     660

ggtgctgtac ttaccaaatg ccaacaaaaa ggatggggag atttcagaaa ctttcaacct     720

agtggaagag atgtaatcgt taaaggccaa ggtacattca aatctaatta tggaacggac     780
```

ttcattttaa aaattgaaga catcacagat tcaaagttac gaaacaataa cgggagtgga 840
actgtcgttc aagagattaa agttccacta attagaactg aaatatag 888

<210> SEQ ID NO 120
<211> LENGTH: 295
<212> TYPE: PRT
<213> ORGANISM: Artificial
<220> FEATURE:
<223> OTHER INFORMATION: An amino acid sequence of a mature TIC7511 protein, mTIC7511.

<400> SEQUENCE: 120

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Gln Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Val
65 70 75 80

Ser Gly Thr Pro Leu Tyr Val Gly Lys Asn Val Leu Asp Asn Ser Lys
85 90 95

Gly Thr Ser Asp Gln Glu Leu Leu Thr Pro Glu Phe Asn Tyr Thr Tyr
100 105 110

Thr Glu Ser Thr Ser Asn Thr Thr Thr His Gly Leu Lys Val Gly Val
115 120 125

Lys Thr Thr Ala Thr Met Lys Phe Pro Ile Ala Gln Gly Ser Met Glu
130 135 140

Ala Ser Thr Glu Tyr Asn Phe Gln Asp Ser Ser Thr Asp Thr Thr Thr
145 150 155 160

Lys Thr Val Ser Tyr Lys Ser Pro Ser Gln Lys Ile Lys Val Pro Ala
165 170 175

Gly Lys Thr Phe Arg Val Leu Ala Tyr Leu Asn Thr Gly Ser Ile Ser
180 185 190

Gly Glu Ala Asn Leu Tyr Ala Asn Val Gly Gly Ile Ala Trp Arg Val
195 200 205

Ser Pro Gly Tyr Pro Asn Gly Gly Gly Val Asn Ile Gly Ala Val Leu
210 215 220

Thr Lys Cys Gln Gln Lys Gly Trp Gly Asp Phe Arg Asn Phe Gln Pro
225 230 235 240

Ser Gly Arg Asp Val Ile Val Lys Gly Gln Gly Thr Phe Lys Ser Asn
245 250 255

Tyr Gly Thr Asp Phe Ile Leu Lys Ile Glu Asp Ile Thr Asp Ser Lys
260 265 270

Leu Arg Asn Asn Asn Gly Ser Gly Thr Val Val Gln Glu Ile Lys Val
275 280 285

Pro Leu Ile Arg Thr Glu Ile
290 295

<210> SEQ ID NO 121
<211> LENGTH: 888
<212> TYPE: DNA
<213> ORGANISM: Artificial
<220> FEATURE:

<223> OTHER INFORMATION: A synthetic nucleotide sequence encoding a mature TIC7513 protein, mTIC7513 for expression in bacteria.

<400> SEQUENCE: 121
atgtcatcca cagatgttca agaaagatta cgggacttgg caagagaaga tgaagctgga 60
acctttaatg aagcatggaa tactaacttc aaacccagtg atgaacaaca attctcttat 120
agtccaactg aaggaattgt tttcttaaca ccacctaaaa atgttattgg cgaaagaaga 180
atttcacagt ataaagtaaa taatgcatgg gctacattag aaggaagtcc aaccgaagca 240
tcggggacac ctttatatgc gggaaaaaac gtattagata actcaaaagg aacaatggat 300
caagagctgt taacacccga gtttaactat acctatacgg aaagcacttc aaatacaaca 360
acccatggat taaaattagg agtcaaaacc actgctacca tgaaattccc gattgctcag 420
ggtagcatgg aagcttctac tgaatataac tttcaaaatt cttccactga tactaaaact 480
aaacaagtat catataaaag cccatcacaa aaaattaaag taccagcagg taaaacctat 540
agagttttag catacctaaa tactggatct atttcaggtg aagctaacct ttacgcaaat 600
gttgggggta tagcttggag ggtttcacca ggttatccca atggcggagg agtaaatata 660
ggtgctgtac ttaccaaatg ccaacaaaaa ggatggggag atttcagaaa ctttcaacct 720
agtggaagag atgtaatcgt taaaggccaa ggtactttca aatctaatta tggaacggac 780
ttcattttaa aaattgaaga catcacagat tcaaagttac gaaacaataa cgggagtgga 840
actgtcgttc aagagattaa agttccacta attagaactg aaatatag 888

<210> SEQ ID NO 122
<211> LENGTH: 295
<212> TYPE: PRT
<213> ORGANISM: Artificial
<220> FEATURE:
<223> OTHER INFORMATION: An amino acid sequence of a mature TIC7513 protein, mTIC7513.

<400> SEQUENCE: 122

Met Ser Ser Thr Asp Val Gln Glu Arg Leu Arg Asp Leu Ala Arg Glu
1 5 10 15

Asp Glu Ala Gly Thr Phe Asn Glu Ala Trp Asn Thr Asn Phe Lys Pro
20 25 30

Ser Asp Glu Gln Gln Phe Ser Tyr Ser Pro Thr Glu Gly Ile Val Phe
35 40 45

Leu Thr Pro Pro Lys Asn Val Ile Gly Glu Arg Arg Ile Ser Gln Tyr
50 55 60

Lys Val Asn Asn Ala Trp Ala Thr Leu Glu Gly Ser Pro Thr Glu Ala
65 70 75 80

Ser Gly Thr Pro Leu Tyr Ala Gly Lys Asn Val Leu Asp Asn Ser Lys
85 90 95

Gly Thr Met Asp Gln Glu Leu Leu Thr Pro Glu Phe Asn Tyr Thr Tyr
100 105 110

Thr Glu Ser Thr Ser Asn Thr Thr Thr His Gly Leu Lys Leu Gly Val
115 120 125

Lys Thr Thr Ala Thr Met Lys Phe Pro Ile Ala Gln Gly Ser Met Glu
130 135 140

Ala Ser Thr Glu Tyr Asn Phe Gln Asn Ser Ser Thr Asp Thr Lys Thr
145 150 155 160

Lys Gln Val Ser Tyr Lys Ser Pro Ser Gln Lys Ile Lys Val Pro Ala
165 170 175

```
Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 123
<211> LENGTH: 888
<212> TYPE: DNA
<213> ORGANISM: Artificial
<220> FEATURE:
<223> OTHER INFORMATION: A synthetic nucleotide sequence encoding a mature TIC7518 protein, mTIC7518 for expression in bacteria.

<400> SEQUENCE: 123

```
atgtcatcca cagatgttca agaaagatta cgggacttgg caagagaaaa tgaagctgga     60

acccttaatg aagcatggaa tactaacttc aaacccagtg atgaacaaca attctcttat    120

agtccaactg aaggaattgt tttcttaaca ccacctaaaa atgttattgg cgaaagaaga    180

atttcacagt ataaagtaaa taatgcatgg gctacattag aaggaagtcc aaccgaagta    240

tcggggacac ctttatatgc gggaaaaaac gtattagata actcaaaagg aacaatggat    300

caagagctgt taacacccga gtttaactat acctatacgg aaagcacttc aaatacaata    360

actcatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaaccttt    540

agagttttag catacctaaa tactggatct atttcaggtg aagctaacct ttacgcaaat    600

gttgggggta tagcttgggg ggttttacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttcg aatctaatta tggaacggac    780

ttcattttaa aaattgaaga catcacagat tcaaagttac gaaacaataa cgggagtgga    840

actgtcgttc aagagattaa agttccacta attagaactg aaatatag                 888
```

<210> SEQ ID NO 124
<211> LENGTH: 295
<212> TYPE: PRT
<213> ORGANISM: Artificial
<220> FEATURE:
<223> OTHER INFORMATION: An amino acid sequence of a mature TIC7518 protein, mTIC7518.

<400> SEQUENCE: 124

```
Met Ser Ser Thr Asp Val Gln Glu Arg Leu Arg Asp Leu Ala Arg Glu
1               5                   10                  15
```

-continued

```
Asn Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Ile Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Gly Val
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Glu Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 125
<211> LENGTH: 888
<212> TYPE: DNA
<213> ORGANISM: Artificial
<220> FEATURE:
<223> OTHER INFORMATION: A synthetic nucleotide sequence encoding a mature TIC7524 protein, mTIC7524 for expression in bacteria.

<400> SEQUENCE: 125

```
atgtcatcca cagatgttca agaaagatta cgggacttgg caagagaaga tgaagctgga      60

acctttaatg aagcatggaa tactaacttc aaacccagtg atgaacaaca attctcttat     120

agtccaactg aaggaattgt tttcttaaca ccacctaaaa atgttattgg cgaaagaaga     180

atttcacagt ataaagtaaa taatgcatgg gctacattag aaggaagtcc aaccgaagca     240

tcggggacac ctttatatgc gggaaaaaac gtattagata actcaaaagg aacaatggat     300

caagagctgt taacacccga gtttaactat acctatacgg aaagcacttc aaatacaaca     360

acccatggat taaaattagg agtcaaaacc actgctacca tgaaattccc gattgctcag     420
```

-continued

```
ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttcg aatctaatta tggaacggac    780

ttcattttaa aaattgaaga catcacagat tcaaagttac gaaacaataa cgggagtgga    840

actgtcgttc aagagattaa agttccacta attagaactg aaatatag                  888
```

```
<210> SEQ ID NO 126
<211> LENGTH: 295
<212> TYPE: PRT
<213> ORGANISM: Artificial
<220> FEATURE:
<223> OTHER INFORMATION: An amino acid sequence of a mature TIC7524
      protein, mTIC7524

<400> SEQUENCE: 126

Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Ala
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Glu Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
```

```
        275                 280                 285

Pro Leu Ile Arg Thr Glu Ile
    290                 295


<210> SEQ ID NO 127
<211> LENGTH: 888
<212> TYPE: DNA
<213> ORGANISM: Artificial
<220> FEATURE:
<223> OTHER INFORMATION: A synthetic nucleotide sequence encoding a
      mature TIC7526 protein, mTIC7526 for expression in bacteria.

<400> SEQUENCE: 127

atgtcatcca cagatgttca agaaagatta cgggacttag caagagaaaa tgaagctgga     60

acccttaatg aagcatggaa tactaacttc aaacccagtg atgaacaaca attctcttat    120

agtccaactg aaggtattgt ttcttaaca ccacctaaaa atgttattgg cgaaagaaga    180

atttcacagt ataaagtaaa taatgcatgg gctacattag aaggaagtcc aatcgaagta    240

tcggggacac ctttatatgc gggaaaaaac gtattagata actcaaaagg aacaatggat    300

caagagctgt taacacccga gtttaactat acctatacgg aaagcacttc aaatacaata    360

actcatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaaccttt    540

agagttttag catacctaaa tactggatct atttcaggtg aagctaacct ttacgcaaat    600

gttgggggta tagcttgggg ggttttacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttcg aatctaatta tggaacggac    780

ttcattttaa aaattgaaga catcacagat tcaaagttac gaaacaataa cgggagtgga    840

actgtcgttc aagagattaa agttccacta attagaactg aaatatag                 888


<210> SEQ ID NO 128
<211> LENGTH: 295
<212> TYPE: PRT
<213> ORGANISM: Artificial
<220> FEATURE:
<223> OTHER INFORMATION: An amino acid sequence of a mature TIC7526
      protein, mTIC7526.

<400> SEQUENCE: 128

Met Ser Ser Thr Asp Val Gln Glu Arg Leu Arg Asp Leu Ala Arg Glu
1               5                   10                  15

Asn Glu Ala Gly Thr Leu Asn Glu Ala Trp Asn Thr Asn Phe Lys Pro
            20                  25                  30

Ser Asp Glu Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Ile Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Ile Thr His Gly Leu Lys Leu Gly Val
```

```
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Gly Val
        195                 200                 205

Leu Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Glu Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 129
<211> LENGTH: 888
<212> TYPE: DNA
<213> ORGANISM: Artificial
<220> FEATURE:
<223> OTHER INFORMATION: A synthetic nucleotide sequence encoding a mature TIC7528 protein, mTIC7528 for expression in bacteria.

<400> SEQUENCE: 129

```
atgtcatcca cagatgttca agaaagatta cgggacttgg caagagaaga tgaagctgga      60

acctttaatg aagcatggaa tactaacttc aaacccagtg atcaacaaca attctcttat     120

agtccaactg aaggaattgt tttcttaaca ccacctaaaa atgttattgg cgaaagaaga     180

atttcacagt ataaagtaaa taatgcatgg gctacattag aaggaagtcc aaccgaagta     240

tcggggacac ctttatatgc gggaaaaaac gtattagata actcaaaagg aacaatggat     300

caagagctgt taacacccga gtttaactat acctatacgg aaagcacttc aaatacaaca     360

actcatggat taaaattagg agtcaaaacc actgctacca tgaaattccc gattgctcag     420

ggtagcatgg aagcttctac tgaatataac tttcaaaatt cttccactga tactaaaact     480

aaacaagtat catataaaag cccatcacaa aagattaaag taccagcagg taaaaccttt     540

agagttttag catacctaaa tactggatct atttcaggtg aagctaacct ttacgcaaat     600

gttgggggta tagcttggag ggtttcacca ggttatccca atggcggagg agtaaatata     660

ggtgctgtac ttaccaaatg ccaacaaaaa ggatggggag atttcagaaa ctttcaacct     720

agtggaagag atgtaatcgt taaaggccaa ggtactttca aatctaatta tggaacggac     780

ttcattttaa aaattgaaga catcacagat tcaaagttac gaaacaataa cgggagtgga     840

actgtcgttc aagagattaa agttccacta attagaactg aaatatag                 888
```

<210> SEQ ID NO 130
<211> LENGTH: 295

<212> TYPE: PRT
<213> ORGANISM: Artificial
<220> FEATURE:
<223> OTHER INFORMATION: An amino acid sequence of a mature TIC7528 protein, mTIC7528.

<400> SEQUENCE: 130

```
Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Gln Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Val
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Asn Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Phe Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220

Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

<210> SEQ ID NO 131
<211> LENGTH: 888
<212> TYPE: DNA
<213> ORGANISM: Artificial
<220> FEATURE:
<223> OTHER INFORMATION: A synthetic nucleotide sequence encoding a mature TIC7535 protein, mTIC7535 for expression in bacteria.

<400> SEQUENCE: 131

```
atgtcatcca cagatgttca agaaagatta cgggacttgg caagagaaga tgaagctgga      60

acctttaatg aagcatggaa tactaacttc aaacccagtg atcaacaaca attctcttat     120
```

```
agtccaactg aaggaattgt tttcttaaca ccacctaaaa atgttattgg cgaaagaaga    180

atttcacagt ataaagtaaa taatgcatgg gctacattag aaggaagtcc aaccgaagca    240

tcggggacac ctttatatgc gggaaaaaac gtattagata actcaaaagg aacaatggat    300

caagagctgt taacacccga gtttagttat acctatacgg aaagcacttc aaatacaaca    360

acccatggat taaaattagg agtcaaaacc actgctacca tgaaattccc gattgctcag    420

ggtagcatgg aagcttctac tgaatataac tttcaaaatt cttccactga tactaaaact    480

aaacaagtat catataaaag cccatcacaa aaaattaaag taccagcagg taaaacctat    540

agagttttag catacctaaa tactggatct atttcaggtg aagctaacct ttacgcaaat    600

gttgggggta tagcttggag ggtttcacca ggttatccca atggcggagg agtaaatata    660

ggtgctgtac ttaccaaatg ccaacaaaaa ggatggggag atttcagaaa ctttcaacct    720

agtggaagag atgtaatcgt taaaggccaa ggtactttca aatctaatta tggaacggac    780

ttcattttaa aaattgaaga catcacagat tcaaagttac gaaacaataa cgggagtgga    840

actgtcgttc aagagattaa agttccacta attagaactg aaatatag                 888


<210> SEQ ID NO 132
<211> LENGTH: 295
<212> TYPE: PRT
<213> ORGANISM: Artificial
<220> FEATURE:
<223> OTHER INFORMATION: An amino acid sequence of a mature TIC7535
      protein, mTIC7535.

<400> SEQUENCE: 132

Met Ser Ser Thr Asp Val Gln Glu Arg Leu Arg Asp Leu Ala Arg Glu
1               5                   10                  15

Asp Glu Ala Gly Thr Phe Asn Glu Ala Trp Asn Thr Asn Phe Lys Pro
            20                  25                  30

Ser Asp Gln Gln Gln Phe Ser Tyr Ser Pro Thr Glu Gly Ile Val Phe
        35                  40                  45

Leu Thr Pro Pro Lys Asn Val Ile Gly Glu Arg Arg Ile Ser Gln Tyr
    50                  55                  60

Lys Val Asn Asn Ala Trp Ala Thr Leu Glu Gly Ser Pro Thr Glu Ala
65                  70                  75                  80

Ser Gly Thr Pro Leu Tyr Ala Gly Lys Asn Val Leu Asp Asn Ser Lys
                85                  90                  95

Gly Thr Met Asp Gln Glu Leu Leu Thr Pro Glu Phe Ser Tyr Thr Tyr
            100                 105                 110

Thr Glu Ser Thr Ser Asn Thr Thr Thr His Gly Leu Lys Leu Gly Val
        115                 120                 125

Lys Thr Thr Ala Thr Met Lys Phe Pro Ile Ala Gln Gly Ser Met Glu
    130                 135                 140

Ala Ser Thr Glu Tyr Asn Phe Gln Asn Ser Ser Thr Asp Thr Lys Thr
145                 150                 155                 160

Lys Gln Val Ser Tyr Lys Ser Pro Ser Gln Lys Ile Lys Val Pro Ala
                165                 170                 175

Gly Lys Thr Tyr Arg Val Leu Ala Tyr Leu Asn Thr Gly Ser Ile Ser
            180                 185                 190

Gly Glu Ala Asn Leu Tyr Ala Asn Val Gly Gly Ile Ala Trp Arg Val
        195                 200                 205

Ser Pro Gly Tyr Pro Asn Gly Gly Gly Val Asn Ile Gly Ala Val Leu
    210                 215                 220
```

-continued

```
Thr Lys Cys Gln Gln Lys Gly Trp Gly Asp Phe Arg Asn Phe Gln Pro
225                 230                 235                 240

Ser Gly Arg Asp Val Ile Val Lys Gly Gln Gly Thr Phe Lys Ser Asn
                245                 250                 255

Tyr Gly Thr Asp Phe Ile Leu Lys Ile Glu Asp Ile Thr Asp Ser Lys
            260                 265                 270

Leu Arg Asn Asn Asn Gly Ser Gly Thr Val Val Gln Glu Ile Lys Val
        275                 280                 285

Pro Leu Ile Arg Thr Glu Ile
    290                 295
```

INSECT INHIBITORY PROTEINS

REFERENCE TO RELATED APPLICATIONS

This application is a continuation-in-part and claims the benefit of U.S. patent application Ser. No. 14/945,140, filed Nov. 18, 2015, which claims the benefit of priority to U.S. Provisional Application 62/082,504, filed Nov. 20, 2014, which is incorporated herein by reference in its entirety.

INCORPORATION OF SEQUENCE LISTING

A computer readable form of the Sequence Listing is filed herewith by electronic submission. The Sequence Listing is incorporated by reference in its entirety, is contained in the file created on Nov. 29, 2018, having the file name "38-21-60356-0003_SEQLIST" and which is 254,277 bytes in size (as measured in MS-Windows operating system).

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed class of proteins is insecticidally active against agriculturally-relevant pests of crop plants and seeds, particularly Lepidopteran and Coleopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera and Coleoptera, are considered a major cause of damage to field crops, thereby decreasing crop yields over infested areas. Lepidopteran pest species which negatively impact agriculture include, but are not limited to, *Helicoverpa zea. Ostrinia nubilalis, Diatraea saccharalis, Diatraea grandiosella, Anticarsia gemmatalis, Spodoptera frugiperda, Spodoptera exigua, Agrotis ipsilon, Trichoplusia ni, Chrysodeixis includens, Heliothis virescens, Plutella xylostella, Pectinophora gossypiella, Helicoverpa armigera, Elasmopalpus lignosellus, Striacosta albicosta* and *Phyllocnistis citrella.*

Coleopteran pest species which negatively impact agriculture include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp., particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica* balteata (Brazilian Corn Rootworm (BZR), *Diabrotica* undecimpunctata howardii (Southern Corn Rootworm, SCR) and a Brazilian Corn Rootworm complex (BCR) consisting of *Diabrotica viridula* and *Diabrotica speciosa*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for proteins which exhibit pesticidal activity since it was discovered that Bt strains show a high toxicity against specific insects. The main feature of Bt's is the production of parasporal bodies which contain one or more crystals that contain specific insecticidal endotoxins (Cry proteins) which act upon ingestion by a susceptible insect through a pore-forming mechanism of action detrimental for the insect gut epithelium. Besides Bt, other *Bacillus* species, such as *Bacillus sphaericus*, and other bacteria species that contain genes that contribute to an entomopathogenic phenotype, such as *Brevibacillus laterosporus*, have shown potential for pest management.

Insecticidal toxin proteins have been employed in various agricultural applications to preserve agriculturally important plants and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The expanded use of transgenic insect-protected crops and the limited number of commercially available insecticidal toxin proteins is creating a selection pressure for alleles that impart resistance to the currently-utilized insecticidal proteins. The development of resistance in target pests to insecticidal toxin proteins undermines the effectiveness and advantages of this technology. Such advantages include increased crop yields, reduction in chemical pesticide use, and reduction in the costs and labor associated with chemical pesticide use.

The discovery and development of new forms of insecticidal toxin proteins is central to managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, two or more transgenic toxins toxic to the same insect pest and displaying different modes of action in one plant further reduces the probability of resistance in a target insect species.

Consequently, there is a critical need to discover and develop effective insecticidal proteins with improved insecticidal properties such as increased efficacy against a broader spectrum of target insect pest species and different modes of action compared to proteins known in the art. A novel protein toxin family from *Brevibacillus laterosporus* (*B. laterosporus*) is disclosed in this application along with similar toxin proteins, variant proteins, and exemplary recombinant proteins that exhibit insecticidal activity against significant target Lepidopteran and Coleopteran pest species, particularly against Western Corn Rootworm.

SUMMARY OF THE INVENTION

Disclosed herein is a novel group of insect inhibitory recombinant polynucleotide molecules and polypeptides (toxin proteins) encoded thereby, referred to herein as TIC3668-type proteins, which are shown to exhibit inhibitory activity against one or more pests of crop plants. Each of the proteins can be used alone or in combination with each other and with other insecticidal proteins and toxic agents in formulations and in planta, thus providing alternatives to insecticidal proteins and insecticide chemistries currently in use in agricultural systems.

In one aspect, the invention provides a recombinant polynucleotide molecule encoding an insect inhibitory polypeptide comprising an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, and SEQ ID NO:132. In one embodiment, the recombinant polynucleotide molecule encodes an insect inhibitory polypeptide comprising at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, and SEQ ID NO:132. In another embodiment, the recombinant polynucleotide molecule comprises a nucleotide sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO: 127, SEQ ID NO:129, and SEQ ID NO:131. In still another embodiment the recombinant polynucleotide molecule comprises at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to a nucleotide sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, and SEQ ID NO:131. In a further embodiment, the recombinant polynucleotide molecule comprise a sequence that hybridizes to: (i) the reverse complement of the nucleotide sequence from position 4-885 of a sequence selected from the group consisting of SEQ ID NO:37, SEQ ID NO:33, SEQ ID NO:35, SEQ ID NO:39, SEQ ID NO:41, SEQ ID NO:43, SEQ ID NO:45, SEQ ID NO:47, SEQ ID NO:49, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, and SEQ ID NO:131; or (ii) the reverse complement a sequence selected from the group consisting of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. In another embodiment, the hybridization conditions are stringent conditions, for instance, such stringent conditions may comprise hybridization from 4 to 12 hours in 50% formamide, 1 M NaCl, and 1% SDS at 37 C, and a wash in 0.1×SSC at 60 C-65 C. In further embodiment, the recombinant polynucleotide molecule is operably linked to a heterologous promoter.

In another aspect, the invention provides an insect inhibitory recombinant polypeptide encoded by the recombinant polynucleotide molecule provided herein. In one embodiment, the insect inhibitory recombinant polypeptide comprises an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, and SEQ ID NO:132. In another embodiment, the insect inhibitory recombinant polypeptide comprises at least 35% identity, for instance, at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity to an amino acid sequence selected from the group consisting of SEQ ID NO:25, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, and SEQ ID NO:132.

In a further embodiment, the insect inhibitory recombinant polypeptide exhibits inhibitory activity against an insect species of the order Coleoptera, for instance including Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa*. In yet a further embodiment, the insect inhibitory recombinant polypeptide exhibits inhibitory activity against an insect species of the order Lepidoptera, for instance including European Corn Borer, Southwestern Corn Borer, Black Cutworm, Fall Army Worm, Corn Earworm, and Soybean Looper.

In yet another aspect, the invention provides a host cell comprising a recombinant polynucleotide molecule of the invention, wherein the host cell is selected from the group consisting of a bacterial host cell and a plant host cell. In certain embodiments, bacterial host cells include *Agrobacterium, Rhizobium, Bacillus thuringiensis, Brevibacillus lacterosporus, Bacillus cereus, E. coli, Pseudomonas, Klebsiella*, and *Erwinia*. In other embodiments, plant cells include an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, persimmon, pigeon pea, pine, pomegranate, poplar, potato, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In a further aspect, the invention provides an insect inhibitory composition which may comprise a recombinant polynucleotide molecule of the present invention. In one embodiment, the insect inhibitory composition may further comprise a nucleotide sequence encoding at least one other pesticidal agent. In certain embodiments, the at least one other pesticidal agent is different from the TIC3668-type insect inhibitory polypeptide of the invention and may be selected from the group consisting of an insect inhibitory protein, an insect inhibitory dsRNA molecule, and an ancillary protein. In other embodiments, the other pesticidal agent exhibits activity against one or more pest species of the orders Lepidoptera, Coleoptera, or Hemiptera. In certain embodiments, the other pesticidal agent is selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, VIP3A, and VIP3B protein. In yet a further aspect, the present invention provides an insect inhibitory composition comprising an insect inhibitory recombinant polypeptide of the present invention, such as a TIC3668-type insect inhibitory polypeptide, in an insect inhibitory effective amount.

In still another aspect, the invention provides a method of controlling a Coleopteran or Lepidopteran species pest, and controlling a Coleopteran or Lepidopteran species pest infestation of a plant, for instance a crop plant, wherein the method comprises contacting the pest with an insect inhibitory amount of the insect inhibitory recombinant polypeptide of the invention, such as a TIC3668-type insect inhibitory polypeptide.

In a still further aspect, the invention provides a seed comprising a recombinant polynucleotide molecule or insect inhibitory recombinant polypeptide, such as a TIC3668-type insect inhibitory polypeptide, of the invention.

In another aspect, the invention provides a commodity product comprising a detectable amount of the recombinant polynucleotide molecule, or the insect inhibitory polypeptide, such as a TIC3668-type insect inhibitory polypeptide, of the invention. In a further aspect, a commodity product of the invention may comprise a host cell comprising a recombinant polynucleotide molecule of the invention, wherein the commodity product comprises a detectable amount of the recombinant polynucleotide molecule or an insect inhibitory recombinant polypeptide encoded by the recombinant polynucleotide. In certain embodiments, the commodity products may include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

In a yet another aspect, the invention provides a method of producing seed comprising the recombinant polynucleotide of the invention, wherein the method comprises: (a) planting at least one seed comprising the recombinant polynucleotide molecule; (b) growing plants from the seed; and (c) harvesting seed from the plants, wherein the harvested seed comprises the recombinant polynucleotide molecule.

In a further aspect, the invention provides a recombinant vector comprising the recombinant polynucleotide molecule of the invention. In one embodiment, the recombinant vector is selected from the group consisting of a plasmid, a bacmid, a phagemid, and a cosmid.

In another aspect, the invention provides a plant resistant to insect infestation, wherein the cells of said plant comprise the recombinant polynucleotide molecule or the insect inhibitory recombinant polypeptide of the invention.

BRIEF DESCRIPTION OF THE DRAWINGS

FIG. 1 illustrates the alignment of the collage protein TIC4260 to five exemplary TIC3668-type proteins. Positions of sequence diversity are highlighted in gray shading in this sequence alignment.

BRIEF DESCRIPTION OF THE SEQUENCES

Figure 2:
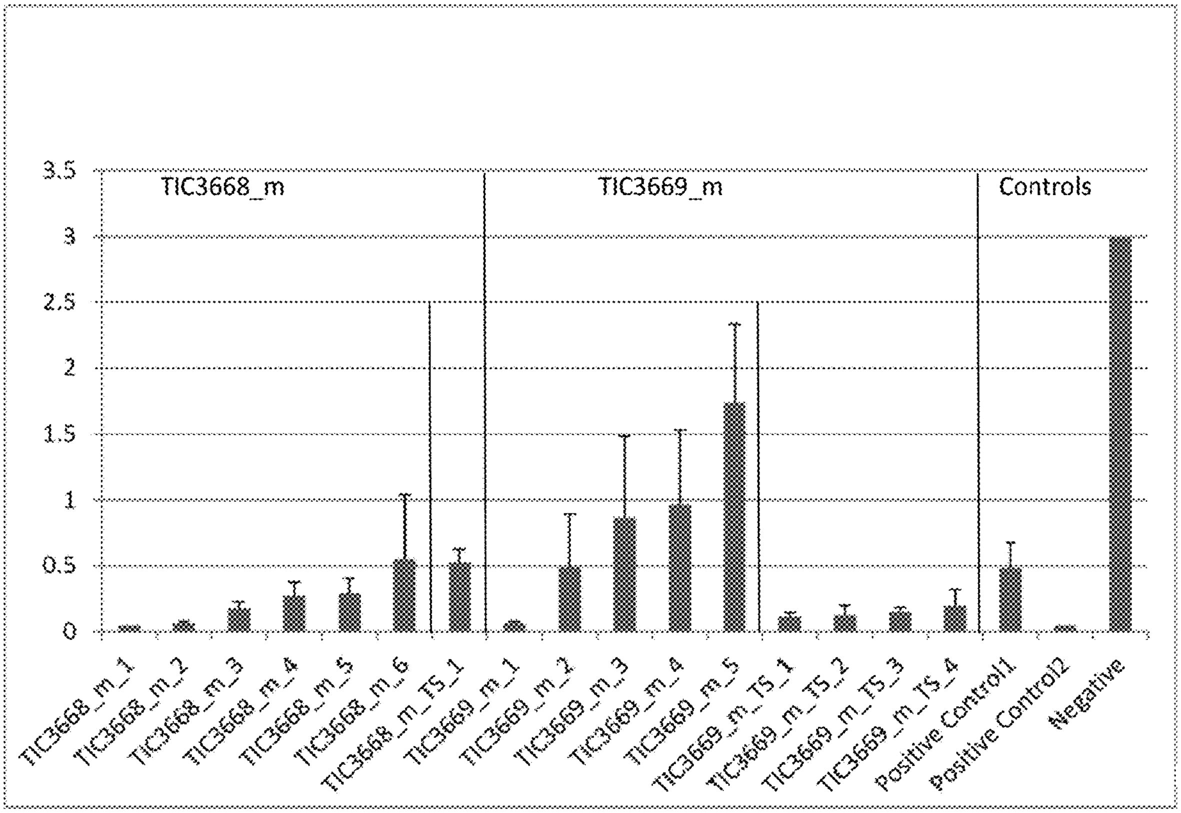
FIG. 2 illustrates in planta Western Corn Rootworm (WCR) inhibitory activity of exemplary chloroplast targeted and non-targeted mature length TIC3668-type proteins.

SEQ ID NO:1 is a recombinant polynucleotide sequence obtained from a *Brevibacillus laterosporus* species encoding a TIC3668 protein from an open reading frame at nucleotide position 1-951 and a translation termination codon.

SEQ ID NO:2 is the amino acid sequence translation of the TIC3668 precursor protein from the open reading frame as set forth in SEQ ID NO:1.

SEQ ID NO:3 is a recombinant polynucleotide sequence obtained from a *Brevibacillus laterosporus* species encoding a TIC3669 protein from an open reading frame at nucleotide position 1-951 and a translation termination codon.

SEQ ID NO:4 is the amino acid sequence translation of the TIC3669 precursor protein from the open reading frame as set forth in SEQ ID NO:3.

SEQ ID NO:5 is a recombinant polynucleotide sequence obtained from a *Brevibacillus laterosporus* species encoding a TIC3670 protein from an open reading frame at nucleotide position 1-951 and a translation termination codon.

SEQ ID NO:6 is the amino acid sequence translation of the TIC3670 precursor protein from the open reading frame as set forth in SEQ ID NO:5.

SEQ ID NO:7 is a recombinant polynucleotide sequence obtained from a *Brevibacillus laterosporus* species encoding a TIC4076 protein from an open reading frame at nucleotide position 1-951 and a translation termination codon.

SEQ ID NO:8 is the amino acid sequence translation of the TIC4076 precursor protein from the open reading frame as set forth in SEQ ID NO:7.

SEQ ID NO:9 is a recombinant polynucleotide sequence obtained from a *Brevibacillus laterosporus* species encoding a TIC4078 protein from an open reading frame at nucleotide position 1-951 and a translation termination codon.

SEQ ID NO:10 is the amino acid sequence translation of the TIC4078 precursor protein from the open reading frame as set forth in SEQ ID NO:9.

SEQ ID NO:11 is a recombinant polynucleotide sequence obtained from a *Brevibacillus laterosporus* species encoding a collage TIC4260 protein from an open reading frame at nucleotide position 1-951 and a translation termination codon, created by combining DNA segments from each of coding sequences set forth in SEQ ID NO:1, SEQ ID NO:3, SEQ ID NO:5, SEQ ID NO:7 and SEQ ID NO:9 in-frame to include the sequence variations from these five different open reading frames.

SEQ ID NO:12 is the amino acid sequence translation of the collage protein TIC4260 precursor protein from the open reading frame as set forth in SEQ ID NO: 11.

SEQ ID NO:13 is a recombinant polynucleotide sequence obtained from a *Brevibacillus laterosporus* species encoding a TIC4346 protein from an open reading frame at nucleotide position 1-951 and a translation termination codon.

SEQ ID NO:14 is the amino acid sequence translation of the TIC4346 precursor protein from the open reading frame as set forth in SEQ ID NO:13.

SEQ ID NO:15 is a recombinant polynucleotide sequence obtained from a *Brevibacillus laterosporus* species encoding a TIC4826 protein from an open reading frame at nucleotide position 1-951 and a translation termination codon.

SEQ ID NO: 16 is the amino acid sequence translation of the TIC4826 precursor protein from the open reading frame as set forth in SEQ ID NO:15.

SEQ ID NO: 17 is a recombinant polynucleotide sequence obtained from a *Brevibacillus laterosporus* species encoding a TIC4861 protein from an open reading frame at nucleotide position 1-918 and a translation termination codon.

SEQ ID NO: 18 is the amino acid sequence translation of the TIC4861 precursor protein from the open reading frame as set forth in SEQ ID NO:17.

SEQ ID NO:19 is a recombinant polynucleotide sequence obtained from a *Brevibacillus laterosporus* species encoding a TIC4862 protein from an open reading frame at nucleotide position 1-945 and a translation termination codon.

SEQ ID NO:20 is the amino acid sequence translation of the TIC4862 precursor protein from the open reading frame as set forth in SEQ ID NO:19.

SEQ ID NO:21 is a recombinant polynucleotide sequence obtained from a *Brevibacillus laterosporus* species encoding a TIC4863 protein from an open reading frame at nucleotide position 1-951 and a translation termination codon.

SEQ ID NO:22 is the amino acid sequence translation of the TIC4863 precursor protein from the open reading frame as set forth in SEQ ID NO:21.

SEQ ID NO:23 is an amino acid sequence of a mature TIC3668 protein, mTIC3668.

SEQ ID NO:24 is an amino acid sequence of a mature TIC3669 protein, mTIC3669.

SEQ ID NO:25 is an amino acid sequence of a mature TIC3670 protein, mTIC3670.

SEQ ID NO:26 is an amino acid sequence of a mature TIC4076 protein, mTIC4076.

SEQ ID NO:27 is an amino acid sequence of a mature TIC4078 protein, mTIC4078.

SEQ ID NO:28 is an amino acid sequence of a mature TIC4260 protein, mTIC4260.

SEQ ID NO:29 is an amino acid sequence of a mature TIC4346 protein, mTIC4346.

SEQ ID NO:30 is an amino acid sequence of a mature TIC4826 protein, mTIC4826.

SEQ ID NO:31 is an amino acid sequence of a mature TIC4861 protein, mTIC4861.

SEQ ID NO:32 is a synthetic nucleotide sequence encoding a TIC3668 protein designed for expression in plants.

SEQ ID NO:33 is a synthetic nucleotide sequence encoding a mature TIC3668 protein, mTIC3668 designed for expression in plants.

SEQ ID NO:34 is a synthetic nucleotide sequence encoding a TIC3669 protein designed for expression in plants.

SEQ ID NO:35 is a synthetic nucleotide sequence encoding a mature TIC3669 protein, mTIC3669 designed for expression in plants.

SEQ ID NO:36 is a synthetic nucleotide sequence encoding a TIC3670 protein designed for expression in plants.

SEQ ID NO:37 is a synthetic nucleotide sequence encoding a mature TIC3670 protein, mTIC3670 designed for expression in plants.

SEQ ID NO:38 is a synthetic nucleotide sequence encoding a TIC4076 protein designed for expression in plants.

SEQ ID NO:39 is a synthetic nucleotide sequence encoding a mature TIC4076 protein, mTIC4076 designed for expression in plants.

SEQ ID NO:40 is a synthetic nucleotide sequence encoding a TIC4078 protein designed for expression in plants.

SEQ ID NO:41 is a synthetic nucleotide sequence encoding a mature TIC4078 protein, mTIC4078 designed for expression in plants.

SEQ ID NO:42 is a synthetic nucleotide sequence encoding a TIC4260 protein designed for expression in plants.

SEQ ID NO:43 is a synthetic nucleotide sequence encoding a mature TIC4260 protein, mTIC4260 designed for expression in plants.

SEQ ID NO:44 is a synthetic nucleotide sequence encoding a TIC4346 protein designed for expression in plants.

SEQ ID NO:45 is a synthetic nucleotide sequence encoding a mature TIC4346 protein, mTIC4346 designed for expression in plants.

SEQ ID NO:46 is a synthetic nucleotide sequence encoding a TIC4826 protein designed for expression in plants.

SEQ ID NO:47 is a synthetic nucleotide sequence encoding a mature TIC4826 protein, mTIC4826 designed for expression in plants.

SEQ ID NO:48 is a synthetic nucleotide sequence encoding a TIC4861 protein designed for expression in plants.

SEQ ID NO:49 is a synthetic nucleotide sequence encoding a mature TIC4861 protein (mTIC4861), a mature TIC4862 protein (mTIC4862), and a mature TIC4863 protein (mTIC4863) designed for expression in plants.

SEQ ID NO:50 is a synthetic nucleotide sequence encoding a TIC4682 protein designed for expression in plants.

SEQ ID NO:51 is a synthetic nucleotide sequence encoding a TIC4863 protein designed for expression in plants.

SEQ ID NO:52 is a nucleotide sequence representing a synthetic oligonucleotide for hybridizing to the (−) strand of a DNA encoding a protein disclosed in this application and corresponds to positions 1 to 36 of SEQ ID NO:1 (TIC3668 forward primer).

SEQ ID NO:53 is a nucleotide sequence representing a synthetic oligonucleotide for hybridizing to the (+) strand of a DNA encoding a protein disclosed in this application and corresponds to positions 920 to 954 of SEQ ID NO:1 (TIC3668 reverse primer).

SEQ ID NO:54 is a nucleotide sequence representing a synthetic oligonucleotide for hybridizing to the (−) strand of a DNA encoding a protein disclosed in this application and corresponds to positions 1 to 41 of SEQ ID NO:3 (TIC3669 forward primer).

SEQ ID NO:55 is a nucleotide sequence representing a synthetic oligonucleotide for hybridizing to the (+) strand of a DNA encoding a protein disclosed in this application and corresponds to positions 920 to 954 of SEQ ID NO:3 (TIC3669 reverse primer).

SEQ ID NO:56 is a nucleotide sequence representing a synthetic oligonucleotide for hybridizing to the (−) strand of a DNA encoding a protein disclosed in this application and corresponds to positions 1 to 36 of SEQ ID NO:5 (TIC3670 forward primer).

SEQ ID NO:57 is a nucleotide sequence representing a synthetic oligonucleotide for hybridizing to the (+) strand of a DNA encoding a protein disclosed in this application and corresponds to positions 920 to 954 of SEQ ID NO:5 (TIC3670 reverse primer).

SEQ ID NO:58 is a nucleotide sequence representing a synthetic oligonucleotide for hybridizing to the (−) strand of a DNA encoding a protein disclosed in this application and corresponds to positions 1 to 41 of SEQ ID NO:7 (TIC4076 forward primer).

SEQ ID NO:59 is a nucleotide sequence representing a synthetic oligonucleotide for hybridizing to the (+) strand of a DNA encoding a protein disclosed in this application and corresponds to positions 920 to 954 of SEQ ID NO:7 (TIC4076 reverse primer).

SEQ ID NO:60 is a nucleotide sequence representing a synthetic oligonucleotide for hybridizing to the (−) strand of a DNA encoding a protein disclosed in this application and corresponds to positions 1 to 36 of SEQ ID NO:9 (TIC4078 forward primer).

SEQ ID NO:61 is a nucleotide sequence representing a synthetic oligonucleotide for hybridizing to the (+) strand of a DNA encoding a protein disclosed in this application and corresponds to positions 920 to 954 of SEQ ID NO:9 (TIC4078 reverse primer).

SEQ ID NO:62 is a recombinant polynucleotide sequence obtained from a *Brevibacillus laterosporus* species encoding a TIC2462 protein from an open reading frame at nucleotide position 1-951 and a translation termination codon.

SEQ ID NO:63 is the amino acid sequence translation of the open reading frame as set forth in SEQ ID NO:62.

SEQ ID NO:64 is a synthetic nucleotide sequence encoding a mature TIC3668 protein, mTIC3668 for expression in bacteria.

SEQ ID NO:65 is a synthetic nucleotide sequence encoding a mature TIC3669 protein, mTIC3669 for expression in bacteria.

SEQ ID NO:66 is a synthetic nucleotide sequence encoding a mature TIC3670 protein, mTIC3670 for expression in bacteria.

SEQ ID NO:67 is a synthetic nucleotide sequence encoding a mature TIC4076 protein, mTIC4076 for expression in bacteria.

SEQ ID NO:68 is a synthetic nucleotide sequence encoding a mature TIC4078 protein, mTIC4078 for expression in bacteria.

SEQ ID NO:69 is a synthetic nucleotide sequence encoding a mature TIC4260 protein, mTIC4260 for expression in bacteria.

SEQ ID NO:70 is a synthetic nucleotide sequence encoding a mature TIC4346 protein, mTIC4346 for expression in bacteria.

SEQ ID NO:71 is a synthetic nucleotide sequence encoding a mature TIC4826 protein, mTIC4826 for expression in bacteria.

SEQ ID NO:72 is a synthetic nucleotide sequence encoding a mature TIC4861 (mTIC4861), TIC4862 (mTIC4862), and TIC4863 (mTIC4863) protein for expression in bacteria.

SEQ ID NO:73 is a recombinant polynucleotide sequence obtained from a *Brevibacillus laterosporus* species encoding a TIC11239 precursor protein from an open reading frame at nucleotide position 1-951 and a translation termination codon.

SEQ ID NO:74 is the amino acid sequence translation of the TIC11239 precursor protein from the open reading frame as set forth in SEQ ID NO:73.

SEQ ID NO:75 is a recombinant polynucleotide sequence obtained from a *Brevibacillus laterosporus* species encoding a TIC11243 precursor protein from an open reading frame at nucleotide position 1-951 and a translation termination codon.

SEQ ID NO:76 is the amino acid sequence translation of the TIC11243 precursor protein from the open reading frame as set forth in SEQ ID NO:75.

SEQ ID NO:77 is a recombinant polynucleotide sequence obtained from a *Brevibacillus laterosporus* species encoding a TIC11256 precursor protein from an open reading frame at nucleotide position 1-951 and a translation termination codon.

SEQ ID NO:78 is the amino acid sequence translation of the TIC11256 precursor protein from the open reading frame as set forth in SEQ ID NO:77.

SEQ ID NO:79 is a recombinant polynucleotide sequence obtained from a *Brevibacillus laterosporus* species encoding a TIC4544 precursor protein from an open reading frame at nucleotide position 1-951 and a translation termination codon.

SEQ ID NO:80 is the amino acid sequence translation of the TIC4544 precursor protein from the open reading frame as set forth in SEQ ID NO:79.

SEQ ID NO:81 is a recombinant polynucleotide sequence obtained from a *Brevibacillus laterosporus* species encoding a TIC4545 precursor protein from an open reading frame at nucleotide position 1-951 and a translation termination codon.

SEQ ID NO:82 is the amino acid sequence translation of the TIC4545 precursor protein from the open reading frame as set forth in SEQ ID NO:81.

SEQ ID NO:83 is a recombinant polynucleotide sequence obtained from a *Brevibacillus laterosporus* species encoding a TIC6871 precursor protein from an open reading frame at nucleotide position 1-951 and a translation termination codon.

SEQ ID NO:84 is the amino acid sequence translation of the TIC6871 precursor protein from the open reading frame as set forth in SEQ ID NO:83.

SEQ ID NO:85 is a recombinant polynucleotide sequence obtained from a *Brevibacillus laterosporus* species encoding a TIC7429 precursor protein from an open reading frame at nucleotide position 1-951 and a translation termination codon.

SEQ ID NO:86 is the amino acid sequence translation of the TIC7429 precursor protein from the open reading frame as set forth in SEQ ID NO:85.

SEQ ID NO:87 is a recombinant polynucleotide sequence obtained from a *Brevibacillus laterosporus* species encoding a TIC7497 precursor protein from an open reading frame at nucleotide position 1-951 and a translation termination codon.

SEQ ID NO:88 is the amino acid sequence translation of the TIC7497 precursor protein from the open reading frame as set forth in SEQ ID NO:87.

SEQ ID NO:89 is a recombinant polynucleotide sequence obtained from a *Brevibacillus laterosporus* species encoding a TIC7511 precursor protein from an open reading frame at nucleotide position 1-951 and a translation termination codon.

SEQ ID NO:90 is the amino acid sequence translation of the TIC7511 precursor protein from the open reading frame as set forth in SEQ ID NO:89.

SEQ ID NO:91 is a recombinant polynucleotide sequence obtained from a *Brevibacillus laterosporus* species encoding a TIC7513 precursor protein from an open reading frame at nucleotide position 1-951 and a translation termination codon.

SEQ ID NO:92 is the amino acid sequence translation of the TIC7513 precursor protein from the open reading frame as set forth in SEQ ID NO:91.

SEQ ID NO:93 is a recombinant polynucleotide sequence obtained from a *Brevibacillus laterosporus* species encoding a TIC7518 precursor protein from an open reading frame at nucleotide position 1-951 and a translation termination codon.

SEQ ID NO:94 is the amino acid sequence translation of the TIC7518 precursor protein from the open reading frame as set forth in SEQ ID NO:93.

SEQ ID NO:95 is a recombinant polynucleotide sequence obtained from a *Brevibacillus laterosporus* species encoding a TIC7524 precursor protein from an open reading frame at nucleotide position 1-951 and a translation termination codon.

SEQ ID NO:96 is the amino acid sequence translation of the TIC7524 precursor protein from the open reading frame as set forth in SEQ ID NO:95.

SEQ ID NO:97 is a recombinant polynucleotide sequence obtained from a *Brevibacillus laterosporus* species encoding a TIC7526 precursor protein from an open reading frame at nucleotide position 1-951 and a translation termination codon.

SEQ ID NO:98 is the amino acid sequence translation of the TIC7526 precursor protein from the open reading frame as set forth in SEQ ID NO:97.

SEQ ID NO:99 is a recombinant polynucleotide sequence obtained from a *Brevibacillus laterosporus* species encoding a TIC7528 precursor protein from an open reading frame at nucleotide position 1-951 and a translation termination codon.

SEQ ID NO:100 is the amino acid sequence translation of the TIC7528 precursor protein from the open reading frame as set forth in SEQ ID NO:99.

SEQ ID NO:101 is a recombinant polynucleotide sequence obtained from a *Brevibacillus laterosporus* species encoding a TIC7535 precursor protein from an open reading frame at nucleotide position 1-951 and a translation termination codon.

SEQ ID NO:102 is the amino acid sequence translation of the TIC7535 precursor protein from the open reading frame as set forth in SEQ ID NO:101.

SEQ ID NO:103 is a synthetic nucleotide sequence encoding a mature TIC11239 protein, mTIC11239 for expression in bacteria.

SEQ ID NO:104 is an amino acid sequence of a mature TIC11239 protein, mTIC11239.

SEQ ID NO:105 is a synthetic nucleotide sequence encoding a mature TIC11243 protein, mTIC11243 for expression in bacteria.

SEQ ID NO:106 is an amino acid sequence of a mature TIC11243 protein, mTIC11243.

SEQ ID NO:107 is a synthetic nucleotide sequence encoding a mature TIC11256 protein, mTIC11256 for expression in bacteria.

SEQ ID NO:108 is an amino acid sequence of a mature TIC1256 protein, mTIC11256.

SEQ ID NO:109 is a synthetic nucleotide sequence encoding a mature TIC4544 protein, mTIC4544 for expression in bacteria.

SEQ ID NO:110 is an amino acid sequence of a mature TIC4544 protein, mTIC4544.

SEQ ID NO: 111 is a synthetic nucleotide sequence encoding a mature TIC4545 protein, mTIC4545 for expression in bacteria.

SEQ ID NO:112 is an amino acid sequence of a mature TIC4545 protein, mTIC4545.

SEQ ID NO:113 is a synthetic nucleotide sequence encoding a mature TIC6871 protein, mTIC6871 for expression in bacteria.

SEQ ID NO:114 is an amino acid sequence of a mature TIC6871 protein, mTIC6871.

SEQ ID NO:115 is a synthetic nucleotide sequence encoding a mature TIC7429 protein, mTIC7429 for expression in bacteria.

SEQ ID NO:116 is an amino acid sequence of a mature TIC7429 protein, mTIC7429.

SEQ ID NO:117 is a synthetic nucleotide sequence encoding a mature TIC7497 protein, mTIC7497 for expression in bacteria.

SEQ ID NO:118 is an amino acid sequence of a mature TIC7497 protein, mTIC7497.

SEQ ID NO:119 is a synthetic nucleotide sequence encoding a mature TIC7511 protein, mTIC7511 for expression in bacteria.

SEQ ID NO:120 is an amino acid sequence of a mature TIC7511 protein, mTIC7511.

SEQ ID NO:121 is a synthetic nucleotide sequence encoding a mature TIC7513 protein, mTIC7513 for expression in bacteria.

SEQ ID NO:122 is an amino acid sequence of a mature TIC7513 protein, mTIC7513.

SEQ ID NO:123 is a synthetic nucleotide sequence encoding a mature TIC7518 protein, mTIC7518 for expression in bacteria.

SEQ ID NO:124 is an amino acid sequence of a mature TIC7518 protein, mTIC7518.

SEQ ID NO: 125 is a synthetic nucleotide sequence encoding a mature TIC7524 protein, mTIC7524 for expression in bacteria.

SEQ ID NO: 126 is an amino acid sequence of a mature TIC7524 protein, mTIC7524.

SEQ ID NO:127 is a synthetic nucleotide sequence encoding a mature TIC7526 protein, mTIC7526 for expression in bacteria.

SEQ ID NO: 128 is an amino acid sequence of a mature TIC7526 protein, mTIC7526.

SEQ ID NO:129 is a synthetic nucleotide sequence encoding a mature TIC7528 protein, mTIC7528 for expression in bacteria.

SEQ ID NO:130 is an amino acid sequence of a mature TIC7528 protein, mTIC7528.

SEQ ID NO:131 is a synthetic nucleotide sequence encoding a mature TIC7535 protein, mTIC7535 for expression in bacteria.

SEQ ID NO:132 is an amino acid sequence of a mature TIC7535 protein, mTIC7535.

DETAILED DESCRIPTION OF THE INVENTION

The problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel insecticidal proteins exemplified by TIC3668 are disclosed herein, and address each of these needs, particularly against a broad spectrum of Coleopteran and Lepidopteran insect pests, and more particularly against corn rootworm pest species.

Reference in this application to "TIC3668", "TIC3668 protein", "TIC3668 protein toxins", "TIC3668 toxin proteins", "TIC3668-related toxins", "TIC3668-related protein toxin class or family", "TIC3668-related toxin proteins", "TIC3668-type proteins", "TIC3668-like proteins, "TIC3668-related toxin polypeptides", "TIC3668-related pesticidal proteins", or "TIC3668-type insect inhibitory polypeptide" and the like, refer to any novel insect inhibitory protein that comprises, that consists of, that is substantially homologous to, that is similar to, or that is derived from any insect inhibitory polypeptide sequence of TIC3668 (SEQ ID NO:2) and insect inhibitory segments thereof, or combinations thereof, that confer activity against Coleopteran pests and Lepidopteran pests, including any protein exhibiting insect inhibitory activity if alignment of such protein with TIC3668 (SEQ ID NO:2), TIC3669 (SEQ ID NO:4), TIC3670 (SEQ ID NO:6), TIC4076 (SEQ ID NO:8), TIC4078 (SEQ ID NO:10), TIC4346 (SEQ ID NO:14), TIC4826 (SEQ ID NO:16), TIC4861 (SEQ ID NO:18), TIC4862 (SEQ ID NO:20), TIC4863 (SEQ ID NO:22), TIC11239 (SEQ ID NO:74), TIC11243 (SEQ ID NO:76), TIC11256 (SEQ ID NO:78), TIC4544 (SEQ ID NO:80), TIC4545 (SEQ ID NO:82), TIC6871 (SEQ ID NO:84), TIC7429 (SEQ ID NO:86), TIC7497 (SEQ ID NO:88), TIC7511 (SEQ ID NO:90), TIC7513 (SEQ ID NO:92), TIC7518 (SEQ ID NO:94), TIC7524 (SEQ ID NO:96), TIC7526 (SEQ ID NO:98), TIC7528 (SEQ ID NO: 100), and TIC7535 (SEQ ID NO: 102) results in amino acid sequence identity of any fraction percentage from about 35% to about 100% percent. The TIC3668-type protein toxins disclosed in this application include TIC3668, TIC3669, TIC3670, TIC4076, TIC4078, TIC4346, TIC4826, TIC4861, TIC4862, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, TIC7535, and the collage TIC4260 protein (SEQ ID NO:12). The TIC3668-type protein class is intended to include the precursor forms as well as the mature length forms of the proteins.

The term "segment" or "fragment" is used in this application to describe consecutive amino acid or nucleic acid sequences that are shorter than the complete amino acid or nucleic acid sequence describing a TIC3668-type protein. A segment or fragment exhibiting insect inhibitory activity is also disclosed in this application if alignment of such segment or fragment, with the corresponding section of the TIC3668-type protein set forth in SEQ ID NO:2, results in amino acid sequence identity of any fraction percentage from about 35 to about 100 percent between the segment or fragment and the corresponding section of the TIC3668-type protein.

Reference in this application to the terms "active" or "activity", "pesticidal activity" or "insecticidal activity", "insect inhibitory" or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC3668-type protein) or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera or Coleoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the protein toxins set forth in this application, as well as other proteinaceous toxic agents including those that target Lepidopteran and Coleopteran, as well as protein toxins that are used to control other plant pests such as Cry proteins available in the art for use in controlling Hemipteran and Homopteran species.

It is intended that reference to a pest, particularly a pest of a crop plant, means insect pests of crop plants, particularly those that are controlled by the TIC3668-related protein toxin class. However, reference to a pest can also include Hemipteran and Homopteran insect pests of plants, as well as nematodes and fungi when toxic agents targeting these pests are co-localized or present together with one or more proteins of the TIC3668-related protein toxin class.

The individual proteins which comprise the TIC3668-related protein class are related by common function and exhibit insecticidal activity towards insect pests from the Coleoptera and Lepidoptera insect species, including adults, pupae, larvae, and neonates. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips* rosana (European leafroller) and other *Archips* species, *Chilo suppressalis* (Asiatic rice borer, or rice stem borer), Cnaphalocrocis *medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafininer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer). The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica* balteata (Brazilian Corn Rootworm (BZR), *Diabrotica undecimpunctata howardii* (Southern Corn Rootworm, SCR) and a Brazilian Corn Rootworm complex (BCR) consisting of *Diabrotica viridula* and *Diabrotica speciosa*).

Reference in this application to an “isolated DNA molecule”, “isolated polynucleotide molecule”, or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be “isolated” so long as the element is within the genome of the organism and at the location within the genome in which it is naturally found. However, each of these elements, and subparts of these elements, would be “isolated” within the scope of this disclosure so long as the element is not within the genome of the organism and at the location within the genome in which it is naturally found. Similarly, a nucleotide sequence encoding a insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in this application, an open reading frame (ORF) (SEQ ID NO:1) encoding TIC3668 (SEQ ID NO:2) was discovered in DNA obtained from *Brevibacillus laterosporus* strain EG5552. Other bacterial genomes were then screened for sequences encoding TIC3668-related protein. Several other open reading frames were identified in these other bacterial genomes encoding amino acid sequences resembling the EG5552 TIC3668 protein, including the TIC3668-like proteins TIC3669 which was discovered in DNA obtained from *Brevibacillus laterosporus* strain EG5551 (SEQ ID NO:3 encoding SEQ ID NO:4), TIC3670 which was discovered in DNA obtained from *Brevibacillus laterosporus* strain EG5553 (SEQ ID NO:5 encoding SEQ ID NO:6), TIC4076 which was discovered in DNA obtained from *Brevibacillus laterosporus* strain ATCC6456 (SEQ ID NO:7 encoding SEQ ID NO:8), TIC4078 which was discovered in DNA obtained from *Brevibacillus laterosporus* strain EG4227 (SEQ ID NO:9 encoding SEQ ID NO:10), TIC4346 which was discovered in DNA obtained from

*Brevibacillus laterosporus* strain EG5551 (SEQ ID NO: 13 encoding SEQ ID NO: 14), TIC4826 which was discovered in DNA obtained from *Brevibacillus laterosporus* strain AG0021D10 (SEQ ID NO:15 encoding SEQ ID NO:16), TIC4861 (SEQ ID NO:17 encoding SEQ ID NO:18), TIC4862 (SEQ ID NO:19 encoding SEQ ID NO:20) and TIC4863 (SEQ ID NO:21 encoding SEQ ID NO:22) which were discovered in DNA obtained from *Brevibacillus laterosporus* strain EG4227, TIC11239 which was discovered in DNA obtained from *Brevibacillus laterosporus* strain DSC004653 (SEQ ID NO:73 encoding SEQ ID NO:74), TIC11243 which was discovered in DNA obtained from *Brevibacillus laterosporus* strain DSC006878 (SEQ ID NO:75 encoding SEQ ID NO:76), TIC11256 which was discovered in DNA obtained from *Brevibacillus laterosporus* strain DSC010447 (SEQ ID NO:77 encoding SEQ ID NO:78), TIC4544 (SEQ ID NO:79 encoding SEQ ID NO:80) and TIC4545 (SEQ ID NO:81 encoding SEQ ID NO:82) which were discovered in DNA obtained from *Brevibacillus laterosporus* strain EG5551, TIC6871 which was discovered in DNA obtained from *Brevibacillus laterosporus* strain DSC004348 (SEQ ID NO:83 encoding SEQ ID NO:84), TIC7429 which was discovered in DNA obtained from *Brevibacillus laterosporus* strain DSC007446 (SEQ ID NO:85 encoding SEQ ID NO:86), TIC7497 which was discovered in DNA obtained from *Brevibacillus laterosporus* strain DSC007646 (SEQ ID NO:87 encoding SEQ ID NO:88), TIC7511 which was discovered in DNA obtained from *Brevibacillus laterosporus* strain AG0107C08 (SEQ ID NO:89 encoding SEQ ID NO:90), TIC7513 which was discovered in DNA obtained from *Brevibacillus laterosporus* strain DSC004494 (SEQ ID NO:91 encoding SEQ ID NO:92), TIC7518 which was discovered in DNA obtained from *Brevibacillus laterosporus* strain DSC004344 (SEQ ID NO:93 encoding SEQ ID NO:94), TIC7524 which was discovered in DNA obtained from *Brevibacillus laterosporus* strain DSC004820 (SEQ ID NO:95 encoding SEQ ID NO:96), TIC7526 which was discovered in DNA obtained from *Brevibacillus laterosporus* strain DSC005166 (SEQ ID NO:97 encoding SEQ ID NO:98), TIC7528 which was discovered in DNA obtained from *Brevibacillus laterosporus* strain DSC005474 (SEQ ID NO:99 encoding SEQ ID NO: 100), and TIC7535 which was discovered in DNA obtained from *Brevibacillus laterosporus* strain DSC007651 (SEQ ID NO:101 encoding SEQ ID NO:102). One additional TIC3668-like protein, TIC4260 (SEQ ID NO:11 encoding SEQ ID NO:12), was created by combining the naturally occurring amino acid sequence variation from five different native TIC3668-like proteins to create a collage protein.

The respective coding sequences were cloned and expressed in microbial host cells to produce recombinant proteins for use in insect bioassays. As described further in this application, it is shown that these proteins exhibit bioactivity against *Diabrotica* species, including Western Corn Rootworm (WCR, *Diabrotica virgifera virgifera*) and Northern Corn Rootworm (NCR, *Diabrotica barberi*); as well as Lepidopteran species, including Western European Corn Borer (ECB, *Ostrinia nubialis*), Southwestern Corn Borer (SWC, *Diatraea grandiosella*), and Soybean Looper (SBL, *Chrysodeixis includens*).

A surprising feature of the TIC3668-type proteins is the presence of a N-terminal amino acid segment corresponding to amino acid position 1 to 23 for TIC3668, TIC3669, TIC3670, TIC4076, TIC4078, TIC4260, TIC4346, TIC4826, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535; 1 to 12 for TIC4861; and 1 to 21 for TIC4862. Each of these N-terminal amino acid segments may be omitted from the respective protein and the polynucleotide sequence encoding the respective segment may also be omitted. When expressed in planta, omission of these respective segments surprisingly resulted in an increase of insecticidal activity against corn rootworm species compared to expression of the full-length protein toxin containing the omitted segment. Protein toxin segments lacking the N-terminal amino acid segments referred to above are referred to herein as "mature TIC3668-type toxin proteins". In general, reference to the mature version of a TIC3668-type protein is annotated herein with the letter "m" preceding the name of the toxin to differentiate reference to the mature sequence from the full length native sequence. For example, the mature version of the amino acid sequence for TIC3668 (SEQ ID NO: 2) is mTIC3668 (SEQ ID NO:23). The mature versions for TIC3668 (SEQ ID NO:2), TIC3669 (SEQ ID NO:4), TIC3670 (SEQ ID NO:6), TIC4076 (SEQ ID NO:8), TIC4078 (SEQ ID NO:10), TIC4346 (SEQ ID NO:14), TIC4826 (SEQ ID NO:16), TIC4861 (SEQ ID NO:18), TIC4862 (SEQ ID NO:20), TIC4863 (SEQ ID NO:22), TIC11239 (SEQ ID NO:74), TIC11243 (SEQ ID NO:76), TIC11256 (SEQ ID NO:78), TIC4544 (SEQ ID NO:80), TIC4545 (SEQ ID NO:82), TIC6871 (SEQ ID NO:84), TIC7429 (SEQ ID NO:86), TIC7497 (SEQ ID NO:88), TIC7511 (SEQ ID NO:90), TIC7513 (SEQ ID NO:92), TIC7518 (SEQ ID NO:94), TIC7524 (SEQ ID NO:96), TIC7526 (SEQ ID NO:98), TIC7528 (SEQ ID NO:100), and TIC7535 (SEQ ID NO:102) are mTIC3669 (SEQ ID NO:24), mTIC3670 (SEQ ID NO:25), mTIC4076 (SEQ ID NO:26), mTIC4078 (SEQ ID NO:27), mTIC4260 (SEQ ID NO:28), mTIC4346 (SEQ ID NO:29), mTIC4826 (SEQ ID NO:30), mTIC11239 (SEQ ID NO:104), mTIC11243 (SEQ ID NO:106), mTIC11256 (SEQ ID NO:108), mTIC4544 (SEQ ID NO:110), mTIC4545 (SEQ ID NO:112), mTIC6871 (SEQ ID NO:114), mTIC7429 (SEQ ID NO:116), mTIC7497 (SEQ ID NO:118), mTIC7511 (SEQ ID NO:120), mTIC7513 (SEQ ID NO:122), mTIC7518 (SEQ ID NO:124), mTIC7524 (SEQ ID NO:126), mTIC7526 (SEQ ID NO:128), mTIC7528 (SEQ ID NO:130), and mTIC7535 (SEQ ID NO:132), respectively. The full-length proteins TIC4861 (SEQ ID NO: 18), TIC4862 (SEQ ID NO:20) and TIC4863 (SEQ ID NO:22) are sequence length variants of each other and differ only in the length of their N-terminal amino acid segment. Removal of the N-terminal amino acid segment in TIC4861, TIC4862, and TIC4863 creates an identical mature amino acid sequence for mTIC4861, mTIC4862, and mTIC4863. Thus, the amino acid sequences for mTIC4861, mTIC4862, and mTIC4863 are encoded by the same polynucleotide sequence (mTIC4861, SEQ ID NO:31). The mature TIC3668-like protein sequences are encoded by SEQ ID NO:64 (encoding mTIC3668), SEQ ID NO:65 (encoding mTIC3669), SEQ ID NO:66 (encoding mTIC3670), SEQ ID NO:67 (encoding mTIC4076), SEQ ID NO:68 (encoding mTIC4078), SEQ ID NO:69 (encoding mTIC4260), SEQ ID NO:70 (encoding mTIC4346), SEQ ID NO:71 (encoding mTIC4826), SEQ ID NO.72 (encoding mTIC4861, mTIC4862, and mTIC4863), SEQ ID NO:103 (encoding mTIC11239), SEQ ID NO:105 (encoding mTIC11243), SEQ ID NO:107 (encoding mTIC11256), SEQ ID NO: 109 (encoding mTIC4544), SEQ ID NO: 111 (encoding mTIC4545), SEQ ID NO:113 (encoding mTIC6871), SEQ ID NO:115 (encoding mTIC7429), SEQ ID NO:117 (encoding mTIC7497), SEQ ID NO:119 (encoding mTIC7511), SEQ ID NO:121 (encoding mTIC7513), SEQ ID NO:123 (encoding mTIC7518), SEQ ID NO:125 (encoding mTIC7524), SEQ ID NO:127 (encoding mTIC7526), SEQ ID NO:129 (encoding mTIC7528), and SEQ ID NO: 131 (encoding mTIC7535) for expression in bacterial hosts.

Additional members to the TIC3668-type family can be created by using the naturally occurring amino acid variations from some or all family members to create novel proteins of a higher level of amino acid sequence diversity and with novel properties. Variants of the TIC3668-type protein toxin class were produced by aligning the amino acid sequences of TIC3668-type family members and combining differences at the amino acid sequence level into a novel amino acid sequence and making appropriate changes to the polynucleotides encoding these variants. One such example is TIC4260. SEQ ID NO:11 is the polynucleotide sequence encoding the TIC4260 protein (SEQ ID NO:12). The mature protein (mTIC4260, SEQ ID NO:28) is encoded by the polynucleotide sequence of SEQ ID NO:43.

Fragments of the TIC3668-type protein toxins can be truncated forms wherein one or more amino acids are deleted from the N-terminal end, C-terminal end, the middle of the protein, or combinations thereof with insect inhibitory activity. These fragments can be naturally occurring or synthetic variants of TIC3668, TIC3669, TIC3670, TIC4260, TIC4076, TIC4078, TIC4346, TIC4826, TIC4861, TIC4862 TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, or TIC7535 but should retain or improve the insect inhibitory activity of TIC3668, TIC3669, TIC3670, TIC4260, TIC4076, TIC4078, TIC4346, TIC4826, TIC4861, TIC4862 TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, or TIC7535. Truncated N-terminal or C-terminal deletion variants include, but are not limited to, TIC3668, TIC3669, TIC3670, TIC4260, TIC4076, TIC4078, TIC4346, TIC4826, TIC4861, TIC4862 TIC4863, TIC11239, TIC1243, TIC11256, TIC4544, TIC4545, TIC6871, TIC7429, TIC7497, TIC7511, TIC7513, TIC7518, TIC7524, TIC7526, TIC7528, or TIC7535 proteins that lack amino acid residues from either the N-terminus and/or the C-terminus. For example, N-terminal amino acid residues 1 to 23 of a TIC3668 protein can be deleted resulting in a toxin protein having amino acids 24-317 of SEQ ID NO:2. Removing 10 or 20 amino acids from the C-terminal amino acid end of a TIC3668 protein resulted in a loss of insecticidal activity, while removing a single amino acid did not affect activity.

Proteins of the TIC3668-type protein class, and proteins that resemble the proteins of the TIC3668-type protein class, can be identified by comparison to each other using various computer based algorithms known in the art (see Tables 1 and 2). Amino acid sequence identities reported herein are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al. (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran insect species is a member of the TIC3668-type protein toxin class if the protein is used in a query, e.g., in a Clustal W alignment, and at least one of the proteins of the present invention as set forth as mTIC4260 is identified as hits in such alignment in which the query protein exhibits at least about 85% to about 100% amino acid sequence identity along the length of the query protein, that is 85%, 86%, 87%, 88%, 89%, 90%, 91%, 92%, 93%, 94%, 95%, 96%, 97%, 98%, 99%, 100%, or any fraction percentage in this range; or at least one of the proteins of the present invention as set forth as mTIC3668 is identified as hits in such alignment in which the query protein exhibits at least about 89% to about 100% amino acid sequence identity along the length of the query protein, that is 89%, 90%, 91%, 92%, 93%, 94%, 95%, 96%, 97%, 98%, 99%, 100%0, or any fraction percentage in this range; or at least one of the proteins of the present invention as set forth as mTIC3669 and/or mTIC3670 are identified as hits in such alignment in which the query protein exhibits at least about 90% to about 100% amino acid sequence identity along the length of the query protein, that is 90%, 91%, 92%, 93%, 94%, 95%, 96%, 97%, 98%, 99%, 100%, or any fraction percentage in this range; or at least one of the proteins of the present invention as set forth as mTIC4826 is identified as a hit in such alignment in which the query protein exhibits at least about 91% to about 100% amino acid sequence identity along the length of the query protein, that is 91%, 92%, 93%, 94%, 95%, 96%, 97%, 98%, 99%, 100%, or any fraction percentage in this range.

It is intended that a protein exhibiting insect inhibitory activity against a Coleopteran insect species is a member of the TIC3668-type protein toxin class if the protein is used in a query, e.g., in a Clustal W alignment, and at least one of the proteins of the present invention as set forth as mTIC3668, mTIC3669, mTIC3670, mTIC4076, mTIC4078, mTIC4260, mTIC4346, mTIC4826, mTIC4861, mTIC4862, mTIC4863, mTIC11239, mTIC11243, mTIC11256, mTIC4544, mTIC4545, mTIC6871, mTIC7429, mTIC7497, mTIC7511, mTIC7513, mTIC7518, mTIC7524, mTIC7526, mTIC7528, and mTIC7535 are identified as hits in such alignment in which the query protein exhibits at least about 35% to about 100% amino acid identity along the length of the query protein that is about 35%, 40%, 50%, 60%, 70%, 75%, 76%, 77%, 78%, 79%, 80%, 81%, 82%, 83%, 84%, 85%, 85%, 87%, 88%, 89%, 90%, 91%, 92%, 93%, 94%, 95%, 96%, 97%, 98%, 99%, 100%, or any fraction percentage in this range.

Exemplary proteins of the TIC3668-type protein toxin class were aligned with each other using a Clustal W algorithm. A pair-wise matrix of percent amino acid sequence identities for each pair of the full-length proteins, TIC3668, TIC3670, TIC3669, TIC4076, TIC4346, TIC4861, TIC4862, TIC4863, TIC4826, TIC4078, and TIC4260 was created, as reported in Table 1. A pair-wise matrix of percent amino acid sequence identities for each pair of the mature-length proteins, mTIC4076, mTIC4346, mTIC4826, mTIC4861, mTIC4862, mTIC4863, mTIC3668, mTIC3670, mTIC3669, mTIC4078, and mTIC4260 was created, as reported in Table 2. A pair-wise matrix of percent amino acid sequence identities for the mature-length proteins, mTIC11239, mTIC11243, mTIC11256, mTIC4544, mTIC4545, mTIC6871, mTIC7429, mTIC7497, mTIC7511, mTIC7513, mTIC7518, mTIC7524, mTIC7526, mTIC7528, mTIC7535 in comparison with mTIC3670 was created, as reported in Table 3.

TABLE 1

Pair-wise matrix display of exemplary full-length proteins

| SEQ ID NO: | M | N: 2 | 6 | 4 | 8 | 14 | 18 | 20 | 22 | 16 | 10 | 12 |
|---|---|---|---|---|---|---|---|---|---|---|---|---|
| 2 | TIC3668 | — | 99.4 (315) | 97.8 (310) | 96.2 (305) | 97.2 (308) | 93.1 (295) | 95.6 (303) | 96.5 (306) | 97.2 (308) | 94.3 (299) | 96.2 (305) |
| 6 | TIC3670 | 99.4 (315) | — | 98.4 (312) | 96.8 (307) | 97.2 (308) | 93.7 (297) | 96.2 (305) | 97.2 (308) | 97.8 (310) | 95 (301) | 95.6 (303) |
| 4 | TIC3669 | 97.8 (310) | 98.4 (312) | — | 96.8 (307) | 96.8 (307) | 93.4 (296) | 96.2 (305) | 97.2 (308) | 97.5 (309) | 94.6 (300) | 95.3 (302) |
| 8 | TIC4076 | 96.2 (305) | 96.8 (307) | 96.8 (307) | — | 98.4 (312) | 94.3 (299) | 97.2 (308) | 98.1 (311) | 98.1 (311) | 96.2 (305) | 93.4 (296) |
| 14 | TIC4346 | 97.2 (308) | 97.2 (308) | 96.8 (307) | 98.4 (312) | — | 94.3 (299) | 97.2 (308) | 98.1 (311) | 98.7 (313) | 96.2 (305) | 93.7 (297) |
| 18 | TIC4861 | 96.4 (295) | 97.1 (297) | 96.7 (296) | 97.7 (299) | 97.7 (299) | — | 99.7 (305) | 99.7 (305) | 98.4 (301) | 95.4 (292) | 92.5 (283) |
| 20 | TIC4862 | 96.2 (303) | 96.8 (305) | 96.8 (305) | 97.8 (308) | 97.8 (308) | 96.8 (305) | — | 99.7 (314) | 98.4 (310) | 95.2 (300) | 92.4 (291) |
| 22 | TIC4863 | 96.5 (306) | 97.2 (308) | 97.2 (308) | 98.1 (311) | 98.1 (311) | 96.2 (305) | 99.1 (314) | — | 98.7 (313) | 95.6 (303) | 92.7 (294) |
| 16 | TIC4826 | 97.2 (308) | 97.8 (310) | 97.5 (309) | 98.1 (311) | 98.7 (313) | 95 (301) | 97.8 (310) | 98.7 (313) | — | 95.9 (304) | 93.4 (296) |
| 10 | TIC4078 | 94.3 (299) | 95 (301) | 94.6 (300) | 96.2 (305) | 96.2 (305) | 92.1 (292) | 94.6 (300) | 95.6 (303) | 95.9 (304) | — | 96.2 (305) |
| 12 | TIC4260 | 96.2 (305) | 95.6 (303) | 95.3 (302) | 93.4 (296) | 93.7 (297) | 89.3 (283) | 91.8 (291) | 92.7 (294) | 93.4 (296) | 96.2 (305) | — |

Table Description: Clustal W alignment between (X) versus (Y) are reported in a pair-wise matrix.
Columns under (N) refer to SEQ ID NO. Column (M) refers to protein name (TIC#).
The percent amino acid identity between all pairs is calculated and is represented by the first number in each box.
The second number (in parentheses) in each box represents the number of identical amino acids between the pair.

TABLE 2

Pair-wise matrix display of exemplary mature proteins

| SEQ ID NO: | M | N: 26 | 29 | 30 | 31 | 23 | 25 | 24 | 27 | 28 |
|---|---|---|---|---|---|---|---|---|---|---|
| 26 | mTIC4076 | — | 98.3 (290) | 98 (289) | 98 (289) | 96.3 (284) | 96.9 (286) | 96.6 (285) | 96.3 (284) | 93.2 (275) |
| 29 | mTIC4346 | 98.3 (290) | — | 98.6 (291) | 98 (289) | 97.3 (287) | 97.3 (287) | 96.6 (285) | 96.3 (284) | 93.6 (276) |
| 30 | mTIC4826 | 98 (289) | 98.6 (291) | — | 98.6 (291) | 97.3 (287) | 98 (289) | 97.3 (287) | 95.9 (283) | 93.2 (275) |
| 31 | mTIC4861<br>mTIC4862<br>mTIC4863 | 98 (289) | 98 (289) | 98.6 (291) | — | 96.6 (285) | 97.3 (287) | 96.9 (286) | 95.6 (282) | 92.5 (273) |
| 23 | mTIC3668 | 96.3 (284) | 97.3 (287) | 97.3 (287) | 96.6 (285) | — | 99.3 (293) | 98 (289) | 93.9 (277) | 95.9 (283) |
| 25 | mTIC3670 | 96.9 (286) | 97.3 (287) | 98 (289) | 97.3 (287) | 99.3 (293) | — | 98.6 (291) | 94.6 (279) | 95.3 (281) |
| 24 | mTIC3669 | 96.6 (285) | 96.6 (285) | 97.3 (287) | 96.9 (286) | 98 (289) | 98.6 (291) | — | 94.6 (279) | 95.3 (281) |
| 27 | mTIC4078 | 96.3 (284) | 96.3 (284) | 95.9 (283) | 95.6 (282) | 93.9 (277) | 94.6 (279) | 94.6 (279) | — | 95.9 (283) |
| 28 | mTIC4260 | 93.2 (275) | 93.6 (276) | 93.2 (275) | 92.5 (273) | 95.9 (283) | 95.3 (281) | 95.3 (281) | 95.9 (283) | — |

Table Description: Clustal W alignment between (X) versus (Y) are reported in a pair-wise matrix.
Columns under (N) refer to SEQ ID NO. Column (M) refers to protein name (TIC#).
The percent amino acid identity between all pairs is calculated and is represented by the first number in each box.
The second number (in parentheses) in each box represents the number of identical amino acids between the pair.

TABLE 3

Pair-wise matrix display of exemplary mature proteins in comparison to mTIC3670

| SEQ ID NO: | M | N: 128 | 132 | 114 | 106 | 118 | 25 | 126 | 130 | 108 | 136 | 112 | 116 | 110 | 134 | 122 | 124 |
|---|---|---|---|---|---|---|---|---|---|---|---|---|---|---|---|---|---|
| 128 | mTIC7518 | — | 99.7 (294) | 99.7 (294) | 98.3 (290) | 98 (289) | 97.3 (287) | 97.3 (287) | 97.6 (288) | 96.9 (286) | 96.6 (285) | 96.3 (284) | 96.9 (286) | 97.6 (288) | 97.6 (288) | 97.3 (287) | 95.6 (282) |
| 132 | mTIC7526 | 99.7 (294) | — | 99.3 (293) | 98 (289) | 97.6 (288) | 96.9 (286) | 96.9 (286) | 97.3 (287) | 96.6 (285) | 96.3 (284) | 95.9 (283) | 96.6 (285) | 97.3 (287) | 97.3 (287) | 96.9 (286) | 95.3 (281) |
| 114 | mTIC4545 | 99.7 (294) | 99.3 (293) | — | 98.6 (291) | 98.3 (290) | 97.6 (288) | 97.6 (288) | 98 (289) | 97.3 (287) | 96.9 (286) | 96.6 (285) | 97.3 (287) | 98 (289) | 98 (289) | 97.6 (288) | 95.9 (283) |
| 106 | mTIC11239 | 98.3 (290) | 98 (289) | 98.6 (291) | — | 99 (292) | 99 (292) | 99 (292) | 99.3 (293) | 98.6 (291) | 98.3 (290) | 98 (289) | 98.6 (291) | 98 (289) | 98.6 (291) | 98.3 (290) | 96.6 (285) |
| 118 | mTIC7429 | 98 (289) | 97.6 (288) | 98.3 (290) | 99 (292) | — | 99 (292) | 99 (292) | 99 (292) | 98.6 (291) | 98.3 (290) | 98 (289) | 98.6 (291) | 98 (289) | 98.6 (291) | 98.3 (290) | 96.6 (285) |
| 25 | mTIC3670 | 97.3 (287) | 96.9 (286) | 97.6 (288) | 99 (292) | 99 (292) | — | 100 (295) | 99.7 (294) | 99.7 (294) | 99.3 (293) | 98.3 (290) | 99 (292) | 98.6 (291) | 99 (292) | 98.6 (291) | 96.9 (286) |
| 126 | mTIC7513 | 97.3 (287) | 96.9 (286) | 97.6 (288) | 99 (292) | 99 (292) | 100 (295) | — | 99.7 (294) | 99.7 (294) | 99.3 (293) | 98.3 (290) | 99 (292) | 98.6 (291) | 99 (292) | 98.6 (291) | 96.9 (286) |

TABLE 3-continued

Pair-wise matrix display of exemplary mature proteins in comparison to mTIC3670

| SEQ ID NO: | M | N: 128 | 132 | 114 | 106 | 118 | 25 | 126 | 130 | 108 | 136 | 112 | 116 | 110 | 134 | 122 | 124 |
|---|---|---|---|---|---|---|---|---|---|---|---|---|---|---|---|---|---|
| 130 | mTIC7524 | 97.6 (288) | 97.3 (287) | 98 (289) | 99.3 (293) | 99 (292) | 99.7 (294) | 99.7 (294) | — | 99.3 (293) | 99 (292) | 98 (289) | 98.6 (291) | 98.3 (290) | 98.6 (291) | 98.3 (290) | 96.6 (285) |
| 108 | mTIC11243 | 96.9 (286) | 96.6 (285) | 97.3 (287) | 98.6 (291) | 98.6 (291) | 99.7 (294) | 99.7 (294) | 99.3 (293) | — | 99.7 (294) | 98.6 (291) | 99.3 (293) | 98.3 (290) | 98.6 (291) | 98.3 (290) | 96.6 (285) |
| 136 | mTIC7535 | 96.6 (285) | 96.3 (284) | 96.9 (286) | 98.3 (290) | 98.3 (290) | 99.3 (293) | 99.3 (293) | 99 (292) | 99.7 (294) | — | 98.3 (290) | 99 (292) | 98 (289) | 99 (292) | 98.6 (291) | 96.9 (286) |
| 112 | mTIC4544 | 96.3 (284) | 95.9 (283) | 96.6 (285) | 98 (289) | 98 (289) | 98.3 (290) | 98.3 (290) | 98 (289) | 98.6 (291) | 98.3 (290) | — | 99.3 (293) | 97.6 (288) | 98 (289) | 98.3 (290) | 96.9 (286) |
| 116 | mTIC6871 | 96.9 (286) | 96.6 (285) | 97.3 (287) | 98.6 (291) | 98.6 (291) | 99 (292) | 99 (292) | 98.6 (291) | 99.3 (293) | 99 (292) | 99.3 (293) | — | 98.3 (290) | 98.6 (291) | 98.3 (290) | 96.9 (286) |
| 110 | mTIC11256 | 97.6 (288) | 97.3 (287) | 98 (289) | 98 (289) | 98 (289) | 98.6 (291) | 98.6 (291) | 98.3 (290) | 98.3 (290) | 98 (289) | 97.6 (288) | 98.3 (290) | — | 98 (289) | 97.6 (288) | 96.6 (285) |
| 134 | mTIC7528 | 97.6 (288) | 97.3 (287) | 98 (289) | 98.6 (291) | 98.6 (291) | 99 (292) | 99 (292) | 98.6 (291) | 98.6 (291) | 99 (292) | 98 (289) | 98.6 (291) | 98 (289) | — | 99.7 (294) | 98 (289) |
| 122 | mTIC7497 | 97.3 (287) | 96.9 (286) | 97.6 (288) | 98.3 (290) | 98.3 (290) | 98.6 (291) | 98.6 (291) | 98.3 (290) | 98.3 (290) | 98.6 (291) | 98.3 (290) | 98.3 (290) | 97.6 (288) | 99.7 (294) | — | 98.3 (290) |
| 124 | mTIC7511 | 95.6 (282) | 95.3 (281) | 95.9 (283) | 96.6 (285) | 96.6 (285) | 96.9 (286) | 96.9 (286) | 96.6 (285) | 96.6 (285) | 96.9 (286) | 96.9 (286) | 96.9 (286) | 96.6 (285) | 98 (289) | 98.3 (290) | — |

Table Description: Clustal W alignment between (X) versus (Y) are reported in a pair-wise matrix.
Columns under (N) refer to SEQ ID NO. Column (M) refers to protein name (TIC#).
The percent amino acid identity between all pairs is calculated and is represented by the first number in each box.
The second number (in parentheses) in each box represents the number of identical amino acids between the pair.

The full-length and mature proteins of the TIC3668-type protein toxin class can also be related by primary structure (conserved amino acid motifs), by length (about 295 amino acids for the mature proteins and about 317 amino acids for the full-length proteins) and by other characteristics. The full-length proteins, TIC3668, TIC3670, TIC3669, TIC4076, TIC4346, TIC4861, TIC4862, TIC4863, TIC4826, TIC4078, and TIC4260 from the present invention have a measured mass of about 35 k-Daltons when run on protein gels under denaturing conditions, and the mature proteins have a measured mass of about 32 kDa. Characteristics of the full-length and mature forms of the TIC3668-type protein toxin class, for example, TIC3668, TIC3670, TIC3669, TIC4076, TIC4346, TIC4861, TIC4862, TIC4863, TIC4826, TIC4078, and TIC4260 are reported in Tables 4 and 5.

TABLE 4

Characteristics of Full-length Protein

| Protein | Molecular Weight (in Daltons) | Amino Acid Length | Isoelectric Point | Charge at PH 7.0 | No. of Strongly Basic (—) Amino Acids | No. of Strongly Acidic Amino Acids | No. of Hydrophobic Amino Acids | No. of Polar Amino Acids |
|---|---|---|---|---|---|---|---|---|
| TIC3668 | 34770.96 | 317 | 9.049 | 5.229 | 34 | 29 | 95 | 111 |
| TIC3669 | 34769.91 | 317 | 8.898 | 4.231 | 34 | 30 | 95 | 111 |
| TIC3670 | 34788.89 | 320 | 8.898 | 4.231 | 34 | 30 | 93 | 112 |
| TIC4076 | 34652.83 | 317 | 8.721 | 3.232 | 32 | 29 | 95 | 112 |
| TIC4078 | 34676.86 | 317 | 8.936 | 4.397 | 32 | 28 | 96 | 110 |
| TIC4260 | 34743.98 | 317 | 9.077 | 5.395 | 33 | 28 | 96 | 109 |
| TIC4826 | 34734.97 | 317 | 8.899 | 4.231 | 33 | 29 | 95 | 111 |
| TIC4861 | 33448.24 | 306 | 8.439 | 2.233 | 31 | 29 | 87 | 110 |
| TIC4862 | 34392.43 | 315 | 8.439 | 2.233 | 31 | 29 | 94 | 112 |
| TIC4863 | 34648.77 | 317 | 8.899 | 4.231 | 33 | 29 | 94 | 112 |
| TIC4346 | 34717.95 | 317 | 8.437 | 2.235 | 32 | 30 | 97 | 109 |

TABLE 5

| Characteristics of Mature Protein | | | | | | | | |
|---|---|---|---|---|---|---|---|---|
| Protein | Molecular Weight (in Daltons) | Amino Acid Length | Iso-electric Point | Charge at PH 7.0 | No. of Strongly Basic Amino Acids | No. of Strongly Acidic Amino Acids | No. of Hydrophobic Amino Acids | No. of Polar Amino Acids |
| mTIC3668 | 32317.06 | 295 | 8.722 | 3.064 | 32 | 29 | 83 | 104 |
| mTIC3669 | 32303.95 | 295 | 8.436 | 2.067 | 32 | 30 | 82 | 105 |
| mTIC3670 | 32334.99 | 295 | 8.436 | 2.067 | 32 | 30 | 81 | 105 |
| mTIC4076 | 32186.87 | 295 | 8.000 | 1.068 | 30 | 29 | 82 | 106 |
| mTIC4078 | 32222.96 | 295 | 8.466 | 2.233 | 30 | 28 | 84 | 103 |
| mTIC4260 | 32290.07 | 295 | 8.747 | 3.230 | 31 | 28 | 84 | 102 |
| mTIC4826 | 32269.01 | 295 | 8.436 | 2.066 | 31 | 29 | 82 | 105 |
| mTIC4861 | 32182.81 | 295 | 8.436 | 2.066 | 31 | 29 | 81 | 106 |
| mTIC4862 | | | | | | | | |
| mTIC4863 | | | | | | | | |
| mTIC4346 | 32251.99 | 295 | 7.092 | 0.071 | 30 | 30 | 84 | 103 |

The proteins of the disclosed TIC3668-type protein toxin class represent a new class of insecticidal proteins. With reference to Table 6, all of the numbers above the diagonal line corresponding to 100% identity, represent the number of amino acid differences between the corresponding proteins being compared at the intersection of that particular row and column. The numbers below the diagonal line corresponding to 100% identity represent the percent identity of the corresponding proteins being compared at the intersection of that particular row and column. The mature length members of this protein class exhibit no greater than 90.54% amino acid identity to any other insecticidal protein known in the art, as demonstrated in the alignment provided in Table 6. The insecticidal protein exhibiting the nearest identity to any of the mature length proteins of the present invention is SEQ ID NO:50 in U.S. Patent Application Publication number 20110030093 (AXMI-209) with 90.5% sequence identity to mTIC4076, mTIC4346, mTIC4826, and mTIC4863. This disclosure only teaches activity against Lepidoptera, while exemplary proteins of the present invention demonstrate activity against Coleoptera. HOUDD3_BRELA, F7TVP6_BRELA, and U4WSU1_BRELA are unannotated protein sequences predicted from the open reading frame in genome sequences reported as having been obtained from *B. laterosporous*. No insecticidal activity is reported for these proteins.

TABLE 5

| Alignment of Mature Length TIC3668 Proteins to Prior Art Proteins | | | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| mTIC3668 | 1 | 100 | 6 | 2 | 11 | 18 | 12 | 8 | 8 | 10 | 36 | 32 | 32 | 33 |
| mTIC3669 | 2 | 98.0 | 100 | 4 | 10 | 16 | 14 | 10 | 8 | 9 | 35 | 32 | 32 | 32 |
| mTIC3670 | 3 | 99.3 | 98.6 | 100 | 9 | 16 | 14 | 8 | 6 | 8 | 34 | 30 | 30 | 31 |
| mTIC4076 | 4 | 96.3 | 96.6 | 97.0 | 100 | 11 | 20 | 5 | 6 | 6 | 30 | 28 | 30 | 29 |
| mTIC4078 | 5 | 93.9 | 94.6 | 94.6 | 96.3 | 100 | 12 | 11 | 12 | 13 | 37 | 34 | 36 | 34 |
| mTIC4260 | 6 | 95.9 | 95.3 | 95.3 | 93.2 | 95.9 | 100 | 19 | 20 | 22 | 48 | 44 | 44 | 43 |
| mTIC4346 | 7 | 97.3 | 96.6 | 97.3 | 98.3 | 96.3 | 93.6 | 100 | 4 | 6 | 30 | 26 | 28 | 29 |
| mTIC4826 | 8 | 97.3 | 97.3 | 98.0 | 98.0 | 95.9 | 93.2 | 98.6 | 100 | 4 | 30 | 24 | 24 | 25 |
| mTIC4863 | 9 | 96.6 | 97.0 | 97.3 | 98.0 | 95.6 | 92.5 | 98.0 | 98.6 | 100 | 30 | 28 | 28 | 27 |
| AXMI-209 | 10 | 88.6 | 89.0 | 89.3 | 90.5 | 88.3 | 84.9 | 90.5 | 90.5 | 90.4 | 100 | 6 | 8 | 7 |
| H0UDD3_BRELA | 11 | 89.9 | 89.9 | 90.5 | 91.2 | 89.3 | 86.1 | 91.8 | 92.4 | 91.2 | 98.1 | 100 | 2 | 3 |
| F7TVP6_BRELA | 12 | 89.9 | 89.9 | 90.5 | 90.5 | 88.6 | 86.1 | 91.2 | 92.4 | 91.2 | 97.5 | 99.4 | 100 | 3 |
| U4WSU1_BRELA | 13 | 89.6 | 89.9 | 90.2 | 90.9 | 89.3 | 86.4 | 90.9 | 92.1 | 91.5 | 97.8 | 99.1 | 99.1 | 100 |

Table 7 below presents additional TIC3668-related toxins. With reference to Table 7, all of the numbers above the diagonal line corresponding to 100% identity, represent the number of amino acid differences between the corresponding proteins being compared at the intersection of that particular row and column. The numbers below the diagonal line corresponding to 100% identity represent the percent identity of the corresponding proteins being compared at the intersection of that particular row and column. The mature length members of these proteins in the TIC3668-related toxin class also exhibit no greater than 90.5% amino acid identity to AXMI-209 (SEQ ID NO:50 in U.S. Patent Application Publication number 20110030093).

TABLE 7

Alignment of Mature Length TIC3668 Proteins to Axmi_209

| Mature Toxin | | 1 | 2 | 3 | 4 | 5 | 6 | 7 | 8 | 9 | 10 | 11 | 12 | 13 | 14 | 15 | 17 |
|---|---|---|---|---|---|---|---|---|---|---|---|---|---|---|---|---|---|
| mTIC7513 | 1 | 100 | 1 | 3 | 3 | 1 | 2 | 5 | 3 | 4 | 3 | 4 | 8 | 9 | 7 | 34 | 9 |
| mTIC7524 | 2 | 99.7 | 100 | 2 | 3 | 2 | 3 | 6 | 4 | 5 | 4 | 5 | 7 | 8 | 6 | 35 | 10 |
| mTIC11239 | 3 | 99 | 99.3 | 100 | 3 | 3 | 5 | 6 | 4 | 5 | 4 | 6 | 5 | 6 | 4 | 35 | 10 |
| mTIC7429 | 4 | 99 | 99 | 99 | 100 | 3 | 5 | 6 | 4 | 5 | 4 | 6 | 6 | 7 | 5 | 33 | 10 |
| mTIC11243 | 5 | 99.7 | 99.3 | 98.6 | 98.6 | 100 | 1 | 4 | 2 | 5 | 4 | 5 | 9 | 10 | 8 | 35 | 10 |
| mTIC7535 | 6 | 99.3 | 99 | 98.3 | 98.3 | 99.7 | 100 | 5 | 3 | 4 | 3 | 6 | 10 | 11 | 9 | 36 | 9 |
| mTIC4544 | 7 | 98.3 | 98 | 98 | 98 | 98.6 | 98.3 | 100 | 2 | 5 | 6 | 7 | 11 | 12 | 10 | 36 | 9 |
| mTIC6871 | 8 | 99 | 98.6 | 98.6 | 98.6 | 99.3 | 99 | 99.3 | 100 | 5 | 4 | 5 | 9 | 10 | 8 | 34 | 9 |
| mTIC7497 | 9 | 98.6 | 98.3 | 98.3 | 98.3 | 98.3 | 98.6 | 98.3 | 98.3 | 100 | 1 | 7 | 8 | 9 | 7 | 34 | 5 |
| mTIC7528 | 10 | 99 | 98.6 | 98.6 | 98.6 | 98.6 | 99 | 98 | 98.6 | 99.7 | 100 | 6 | 7 | 8 | 6 | 33 | 6 |
| mTIC11256 | 11 | 98.6 | 98.3 | 98 | 98 | 98.3 | 98 | 97.6 | 98.3 | 97.6 | 98 | 100 | 7 | 8 | 6 | 31 | 10 |
| mTIC7518 | 12 | 97.3 | 97.6 | 98.3 | 98 | 96.9 | 96.6 | 96.3 | 96.9 | 97.3 | 97.6 | 97.6 | 100 | 1 | 1 | 30 | 13 |
| mTIC7526 | 13 | 96.9 | 97.3 | 98 | 97.6 | 96.6 | 96.3 | 95.9 | 96.6 | 96.9 | 97.3 | 97.3 | 99.7 | 100 | 2 | 31 | 14 |
| mTIC4545 | 14 | 97.6 | 98 | 98.6 | 98.3 | 97.3 | 96.9 | 96.6 | 97.3 | 97.6 | 98 | 98 | 99.7 | 99.3 | 100 | 31 | 12 |
| AXMI-209 | 15 | 89.3 | 89 | 89 | 89.6 | 89 | 88.6 | 88.6 | 89.3 | 89.3 | 89.6 | 90.2 | 90.5 | 90.2 | 90.2 | 100 | 29 |
| mTIC7511 | 16 | 96.9 | 96.6 | 96.6 | 96.6 | 96.6 | 96.9 | 96.9 | 96.9 | 98.3 | 98 | 96.6 | 95.6 | 95.3 | 95.9 | 29 | 100 |

The TIC3668 proteins disclosed in this application exhibit activity in diet bioassays against Coleoptera, including WCR. In some cases Lepidopteran activity is also observed.

As described further in the Examples of this application, polynucleotide sequences encoding TIC3668 toxin proteins were designed for use in plants. Exemplary polynucleotides that were designed for expression in plants and encode the full-length of the insect inhibitory TIC3668, TIC3669, TIC3670, TIC4260, TIC4076, TIC4078, TIC4346, TIC4826, TIC4861, TIC4862, and TIC4863 proteins are set forth in SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51. Exemplary polynucleotides that were designed for expression in plants and encode a mature form of the insect inhibitory mTIC3668, mTIC3669, mTIC3670, mTIC4260, mTIC4076, mTIC4078, mTIC4346, mTIC4826, mTIC4861, mTIC4862, and mTIC4863 proteins are set forth in SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49.

Expression cassettes and vectors containing these polynucleotide sequences were constructed and introduced into corn plant cells in accordance with transformation methods and techniques known in the art. Transformed cells were regenerated into transformed plants that were observed to be expressing TIC3668 toxin proteins. To test pesticidal activity, bioassays were performed in the presence of Lepidopteran or Coleopteran pest larvae using plant leaf disks obtained from the transformed plants.

The insect inhibitory activity of exemplary members of the TIC3668-type protein toxin class is described in more detail in the Examples. The exemplary proteins are related by common function and exhibit insecticidal activity towards Coleoptera and Lepidoptera insect species, including adults, pupae, larvae and neonates.

Recombinant polynucleotide compositions that encode TIC3668-type proteins are contemplated. For example, TIC3668-type proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the TIC3668-type protein encoding sequences for expression of the protein in plants or a Bt-functional promoter operably linked to a TIC3668-type protein encoding sequence for expression of the protein in a Bt bacterium or other *Bacillus* species. Other elements can be operably linked to the TIC3668-type protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, and SEQ ID NO:101 that encodes the respective polypeptides or proteins having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, and SEQ ID NO:102. The codons of a recombinant polynucleotide molecule encoding for proteins disclosed herein can be substituted by synonymous codons (known in the art as a silent substitution). Non-limiting examples for modified polynucleotides encoding any of the TIC3668-type proteins disclosed in this application are set forth in SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51 for the full-length protein sequences and SEQ ID NOs:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49 for the mature protein sequences.

A recombinant DNA construct comprising TIC3668-type protein encoding sequences can further comprise a region of DNA that encodes for one or more insect inhibitory agents which can be configured to concomitantly express or co-express with a DNA sequence encoding a TIC3668-type protein, a protein different from a TIC3668-type protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The proteins of this invention can be expressed from a multi-gene expression system in which one or more proteins of the TIC3668-proteins are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules Recombinant polynucleotides or recombinant DNA constructs comprising a TIC3668-type protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC3668-type protein encoding sequence in a host cell, or subsequent expression of the encoded polypeptide. An exogenous recombinant polynucleotide or recombinant DNA construct that comprises a TIC3668-type protein encoding sequence and that is introduced into a host cell is referred herein as a "transgene".

Transgenic bacteria, transgenic plant cells, transgenic plants, and transgenic plant parts that contain a recombinant polynucleotide that expresses any one or more of the TIC3668-type protein encoding sequences are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a monocotyledon, dicotyledon, alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera- or Lepidoptera-inhibitory amounts of a TIC3668-type protein are provided. Such plants can be made by introducing a recombinant polynucleotide that encodes any of the TIC3668-type proteins provided in this application into a plant cell, and selecting a plant derived from said plant cell that expresses an insect, Coleoptera- or Lepidoptera-inhibitory amount of the TIC3668-type proteins. Plants can be derived from the plant cells by regeneration, seed, pollen, or meristem transformation techniques. Methods for transforming plants are known in the art.

Processed plant products, wherein the processed product comprises a detectable amount of a TIC3668-type protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC3668-type protein.

Plants expressing the TIC3668 proteins can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

TIC3668-type protein-encoding sequences and sequences having a substantial percentage identity to TIC3668-type protein-encoding sequences can be identified using methods known to those of ordinary skill in the art such as polymerase chain reaction (PCR), thermal amplification and hybridization. For example, the proteins of the TIC3668-type protein toxin class can be used to produce antibodies that bind specifically to this class of proteins, and can be used to screen for and to find other members of the class.

Further, nucleotide sequences encoding the TIC3668-type protein toxin class (and reverse complement sequences) can be used as probes and primers for screening to identify other members of the class using thermal-cycle or isothermal amplification and hybridization methods. Specifically, oligonucleotides derived from sequences as set forth in any of SEQ ID NOs:52 through 61 can be used to determine the presence or absence of a TIC3668-type transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61 can be used to detect a TIC3668, TIC3669, TIC3670, TIC4076, TIC4078, or TIC4260 transgene in commodity products derived from pooled sources where only a fraction of the commodity product is derived from a transgenic plant containing any of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. It is further recognized that such oligonucleotides can be used to introduce nucleotide sequence variation in each of SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, and SEQ ID NO:61. Such "mutagenesis" oligonucleotides are useful for identification of TIC3668, TIC3669, TIC3670, TIC4076, TIC4078, or TIC4260, amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes an insecticidal protein or insecticidal fragment thereof and hybridizes under stringent hybridization conditions to the second nucleotide sequence. In such case, the second nucleotide sequence can be any of the nucleotide sequences disclosed in the TIC3668-type protein toxin class under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions are known in the art and may vary according to the desired application and outcome and may encompass a variety of reagents and conditions. For instance, washes at higher temperatures constitute more stringent conditions. In certain embodiments, hybridization conditions of the present invention may comprise at least hybridization at 42° C. followed by two washes for five minutes each at room temperature with 2×SSC, 0.1% SDS, followed by two washes for thirty minutes each at 65° C. in 0.5×SSC, 0.1% SDS; or hybridization at 68° C., followed by washing at 68° C., in 2×SSC containing 0.1% SDS; or hybridization from 4 to 12 hours in 50% formamide, 1 M NaCl, and 1% SDS at 37 C, and a wash in 0.1×SSC at 60 C-65 C.

One skilled in the art will recognize that, due to the redundancy of the genetic code, many other sequences are capable of encoding such related proteins, and those sequences, to the extent that they function to express insecticidal proteins either in *Bacillus* strains or in plant cells, are embodiments of the present invention, recognizing of course that many such redundant coding sequences will not hybridize under these conditions to the native *Bacillus* sequences encoding TIC3668. This application contemplates the use of these, and other identification methods known to those of ordinary skill in the art, to identify TIC3668-type protein-encoding sequences and sequences having a substantial percentage identity to TIC3668-type protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC3668-type proteins to derive additional useful embodiments including assembly of segments of TIC3668-type proteins with segments of diverse proteins different from TIC3668 and related proteins. The TIC3668-type protein class may be subjected to alignment to each other and to other *Bacillus* pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity and/or expanded target pest spectrum compared to the parent proteins from which each such segment in the chimera was derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera or Coleoptera infestations of crop plants, with proteins from the TIC3668 toxin protein class are also disclosed in this application. Such methods can comprise growing a plant comprising an insect-, Coleoptera- or Lepidoptera-inhibitory amount of a protein of the TIC3668 toxin protein class. In certain embodiments, such methods can further comprise any one or more of: (i) applying any composition comprising or encoding a protein of the TIC3668-type protein toxin class to a plant or a seed that gives rise to a plant; and (ii) transforming a plant or a plant cell that gives rise to a plant with a polynucleotide encoding a protein of the TIC3668-type protein toxin class. In general, it is contemplated that any protein in the TIC3668-type protein toxin class can be provided in a composition, provided in a microorganism, or provided in a transgenic plant to confer insect inhibitory activity against Lepidopteran or Coleopteran insects.

In certain embodiments, a recombinant polypeptide of the TIC3668-type protein toxin class is the insecticidally active ingredient of an insect inhibitory composition prepared by culturing recombinant *Bacillus* or any other recombinant bacterial cell transformed to express a TIC3668-type protein toxin under conditions suitable to express and produce proteins of the TIC3668-type protein toxin class. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising one or more proteins from the TIC3668-type protein toxin class can further comprise at least one additional polypeptide that exhibits insect inhibitory activity against the same Lepidopteran or Coleopteran insect species, but which is different from the TIC3668-type protein toxin. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. Patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869 and TIC1100, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC400, TIC800, TIC834, TIC1415, Vip3A, VIP3Ab, VIP3B, AXMI-184, AXMI-196, DIG-3, DIG-4, DIG-5, DIG-11, AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and other Lepidopteran-inhibitory proteins known to those of ordinary skill in the art. Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, Axmi184, Axmi205, AxmiR1, TIC407, TIC417, TIC431, TIC807, TIC853, TIC901, TIC1201, TIC3131, DIG-10, eHIPs (U.S. Patent Application Publication No. 2010/0017914) and other Coleopteran-inhibitory proteins known to those of ordinary skill in the art.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Application Publication No. 2013/0097735), TIC807 (U.S. Pat. No. 8,609,936), TIC834 (U.S. Patent Application Publication No. 2013/0269060) and other Hemipteran-active proteins known to those of ordinary skill in the art. Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC3668-type protein toxin class.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

Examples

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of the TIC3668-Related Protein Toxin Class

Bacterial strains exhibiting distinctive attributes, e.g., inferred toxicity, proteomic diversity, and morphological variations when compared with each other, were identified and prepared for genome sequencing using methods well known in the art. A protein TIC3668 (SEQ ID NO:2) exhibiting inhibitory activity against Coleopteran insects in in vitro bioassays was discovered from a *Brevibacillus laterosporus* (*B. laterosporus*) strain EG5552. Other strains were also found to contain proteins that resemble TIC3668. Polynucleotide segments encoding these proteins were cloned, and inserted into a recombinant host strain to test for expression.

Thermal amplification primers were designed to amplify a full-length copy of the gene from the total genomic DNA of different *B. laterosporus* bacterial strains, including EG5552. Separate thermal amplification products (amplicons) were generated from each strain and these were analyzed for the presence of open reading frames that could encode TIC3668-related proteins. Each amplicon was determined to have a single open reading frame, containing a translation initiation codon, followed in frame by a contiguous open reading frame, that terminated with an in-frame translation termination codon. The deduced amino acid sequences obtained from each of these additional different bacterial strains are set forth respectively in SEQ ID NO:2 (TIC3668), SEQ ID NO:4 (TIC3669), SEQ ID NO:6 (TIC3670), SEQ ID NO:8 (TIC4076), SEQ ID NO:10 (TIC4078), SEQ ID NO:14 (TIC4346), SEQ ID NO:16 (TIC4826), SEQ ID NO:18 (TIC4861), SEQ ID NO:20 (TIC4862), SEQ ID NO:22 (TIC4863) SEQ ID NO:74 (TIC11239), SEQ ID NO:76 (TIC11243), SEQ ID NO:78 (TIC11256), SEQ ID NO:80 (TIC4544), SEQ ID NO:82 (TIC4545), SEQ ID NO:84 (TIC6871), SEQ ID NO:86 (TIC7429), SEQ ID NO:88 (TIC7497), SEQ ID NO:90 (TIC7511), SEQ ID NO:92 (TIC7513), SEQ ID NO:94 (TIC7518), SEQ ID NO:96 (TIC7524), SEQ ID NO:98 (TIC7526), SEQ ID NO:100 (TIC7528), and SEQ ID NO:102 (TIC7535). These amplicons were cloned into a recombinant *Bacillus thuringiensis* (Bt) plasmid expression vector downstream of a sporulation specific expression promoter and transformed into an acrystalliferous Bt host cell. The amplicons were also cloned into an *E. coli* expression system. The resulting recombinant strains were observed to express a recombinant protein.

Example 2

Coleopteran Activity of TIC3668-Related Protein Toxin Class

This Example illustrates inhibitory activity exhibited by TIC3668-like proteins against Coleoptera.

Protein preparations produced from recombinant bacteria as described in Example 1, for the full-length proteins of TIC3668, TIC3669, TIC3670, TIC4260, TIC4076 and TIC2462 were submitted for insect diet-overlay bioassays against Colorado Potato Beetle (*Leptinotarsa decemlineata*, CPB) and against at least one corn rootworm species. Known members of corn rootworm species are *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR) and a Brazilian Corn Rootworm complex (BCR) consisting of *Diabrotica viridula* and *Diabrotica speciosa*).

As demonstrated in Table 8, the results show that TIC3668, TIC3669, TIC3670, TIC4260, and TIC4076 exhibited mortality against corn rootworm. TIC2462 (SEQ ID NO:62 encoding SEQ ID NO:63), a protein closely related to the AXMI-209 protein (compared to TIC2462, >99% identical at the amino acid level, and exhibiting only two amino acid differences), did not exhibit mortality against corn rootworm, thus distinguishing the activity of the TIC3668-like protein toxin class from proteins resembling AXMI-209. Surprisingly, mortality against Colorado Potato Beetle, a species typically tested in bioassays as an indicator of Coleopteran activity, was not observed for any of the proteins tested.

TABLE 8

Observed Mortality against Coleopteran Insect Pests of Exemplary Proteins.

| Toxin | Corn Rootworm | CPB |
|---|---|---|
| TIC2462 | − | − |
| TIC3668, TIC3669, TIC3670 | + | − |
| TIC4260, TIC4076 | + | − |
| TIC4078 | NT | − |
| TIC4346 | + | + |
| TIC4826, TIC4861, TIC4862, TIC4863 | NT | NT |

+ = Mortality observed
− = Mortality not observed
NT = Not tested

Example 3

Mature Form of the TIC3668 Protein Toxin

This Example illustrates the presence of a membrane transiting peptide at the amino terminus of the native proteins within the TIC3668 protein toxin class and the discovery of active mature toxin proteins of the TIC3668 protein toxin class.

Bioinformatic analysis using a SignalP program (Petersen, et. al (2011), *Nature Methods,* 8:785-786) of the amino acid sequence translation from the TIC3668 coding sequence (SEQ ID NO: 1) predicted the presence of a membrane transiting segment corresponding to the N-terminal first 23 amino acids.

Experiments were designed to confirm the presence of a membrane transiting segment within each member of the TIC3668-like protein toxin class. TIC3668 was cloned into a Bt host cell behind a non-sporulation specific Bt promoter. The resultant culture supernatants were tested for insecticidal activity. Three forms of protein corresponding to TIC3668 were recovered as a mixture from the supernatant. These different fragments of less than full length TIC3668 protein were later determined by mass spectrometry and N-terminal sequence analysis to contain at their respective amino termini, either amino acid 16, 19, or 24, as set forth in SEQ ID NO:2. Only a small amount of these three truncated forms of TIC3668 were detected in the culture media. The most abundant form of the protein detected was observed to have at its amino terminus the serine at position 24, as set forth in SEQ ID NO:2. Concentrated and purified protein from the culture supernatant exhibited bioactivity against WCR when tested in artificial diet bioassay.

Different expression constructs were created for identifying the smallest peptide segment for each TIC3668-type protein exhibiting insecticidal activity. These constructs were introduced into an acrystalliferous *B. thuringiensis* strain or an *E. coli* strain. One construct was designed for expression of the full length TIC3668 protein, as set forth in SEQ ID NO:2 from amino acid 1 through 317, in an acrystalliferous strain of Bt. Constructs were designed for expression of the full-length TIC3668 protein, and various shorter variant forms of the TIC3668 protein, in an *E. coli* expression system having a carboxy terminal HIS tag sequence (HHHHAHHH). The constructs designed for expression in *E. coli* consisted of: (1) a construct designed to express the full length TIC3668 protein as set forth in SEQ ID NO:2 from amino acid position 1 through 317; (2) a construct designed to express a TIC3668 variant protein having from amino acid 16 through 317 as set forth in SEQ ID NO:2; (3) a construct designed to express a TIC3668 variant protein from amino acid 24 through 317 as set forth in SEQ ID NO:2; (4) a construct designed to express a TIC3668 variant protein from amino acid 26 through amino acid 317 as set forth SEQ ID NO:2; (5) a construct designed to express TIC3668 variant protein from amino acid 28 through 317 as set forth in SEQ ID NO:2. Additionally a TIC3668 protein with an N-terminal 10-his tag and a TVMV (tobacco vein mottling virus) protease site (MHHHHHHHHHHGTETVRFQ) was obtained from an *E. coli* expression system to produce a TIC3668 protein with a start at residue no. 24 as set forth in SEQ ID NO:2.

Protein was obtained from the supernatant of the Bt expression system and subjected to mass spectrometry and N-terminal sequence analysis. The Bt expression system produced the predicted TIC3668 mature toxin from acid 24-317 as set forth in SEQ ID NO:2. Protein was not observed in the *E. coli* supernatants. Protein was obtained from each of the respective *E. coli* expression constructs by osmotic shock to release proteins from the periplasm. Proteins produced from the constructs that were designed to contain amino acid 16 or 24 at the amino terminus of the less than full length protein were confirmed to contain these amino acids at their respective amino terminus. Protein produced from the construct designed to express the full length TIC3668 produced the mature length protein, containing the serine at position 24 as set forth in SEQ ID NO:2 at the amino terminus. Proteins produced from the constructs designed to contain either amino acid 26 or amino acid 28 as set forth in SEQ ID NO:2 as the N-terminal amino acid each surprisingly contained only amino acid 28 as the N-terminal amino acid, suggesting that processing that maintains amino acid number 24 as set forth in SEQ ID NO:2 at the N-terminus may be important for toxin stability.

Protein samples obtained from these expression system analyses were submitted for testing against Western Corn Rootworm larvae in insect diet-overlay bioassays, as described in Example 2. Certain N-terminal truncations from this study were determined to exhibit decreased bioactivity. Specifically, it was observed that the insecticidal activity was significantly reduced when the amino terminal amino acid was 26 or 28, as set forth in SEQ ID NO:2. It can be extrapolated that other TIC3668 protein family members that are N-terminally truncated to be shorter than the mature protein (starting at amino acid residue no. 24 for TIC3668, TIC3669, TIC3670, TIC4076, TIC4078, TIC4260, TIC4346, TIC4826, TIC4863, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535; starting at amino acid 13 for TIC4861; and starting at amino acid 22 for TIC4862), are the shortest version of the tested TIC3668-type proteins to show insecticidal activity against WCR. All variants of TIC3668 of equal length or longer than the mature protein showed high activity against WCR, even at relatively low concentrations. The data also demonstrates that the *E. coli* processing of TIC3668 varies by construct design.

Example 4

Synthesis of Genes Encoding TIC3668-Type Proteins for Expression in Plants

Nucleotide sequences encoding full-length and mature versions of a TIC3668 protein, a TIC3669 protein, a TIC3670, a TIC4076, TIC4078, a TIC4260 protein, a TIC4346 protein, a TIC4826 protein, a TIC4861 protein, a TIC4862 protein, and a TIC4863 protein were designed. Nucleotide sequences encoding TIC3668, TIC3669, and TIC3670 were synthesized according to methods generally described in U.S. Pat. No. 5,500,365, avoiding certain inimical problem sequences such as ATTTA and A/T rich plant polyadenylation sequences while preserving the amino acid sequence of the native *B. laterosperous* protein. These nucleotide sequences are provided herein as SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, and SEQ ID NO:51 for the full-length sequences and SEQ ID NO:33, SEQ ID NO:35, SEQ ID NO:37, SEQ ID NO:39, SEQ ID NO:41, SEQ ID NO:43, SEQ ID NO:45, SEQ ID NO:47, and SEQ ID NO:49 for the mature sequences.

Example 5

Expression Cassettes for Expression of TIC3668-Type Proteins in Plants

A variety of plant expression cassettes were designed with the sequences as set forth in SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated with the native N-terminal segment. Another set of expression cassettes was designed to allow the expression of the protein without the N-terminal segment (i.e., the mature length protein). Another set of expression cassettes was designed to have a transit peptide expressed in-frame and operably linked to the mature length toxin protein, to allow targeting to an organelle of the cell such as the chloroplast or plastid. All expression cassettes were designed to begin at the 5' end with a promoter which can be comprised of multiple contiguously linked promoter elements, enhancer elements or other expression elements known to those of ordinary skill in the art to boost the expression of the transgene. The promoter sequence was usually followed contiguously with one or more leader sequences 3' to the promoter. An intron sequence was provided 3' to the leader sequence to improve expression of the transgene. A coding sequence for the toxin or transit peptide and coding sequence for the toxin was located 3' of the promoter, leader and intron configuration. A 3'UTR sequence was provided 3' of the coding sequence to facilitate termination of transcription and provides sequences important for the polyadenylation of the resulting transcript. All of the elements described above were arranged contiguously with often additional sequence provided for the construction of the expression cassette such as restriction endonuclease sites or ligation independent cloning sites.

Example 6

Transformation Vectors Containing TIC3668-Type Protein Expression Cassette

*Agrobacterium*-mediated transformation vectors were constructed to deliver DNA to the plant genome that expresses the TIC3668, mTIC3668, TIC3669, mTIC3669, TIC3670, and mTIC3670 proteins. Expression cassettes were cloned into suitable vectors between the *Agrobacterium* border sequences such that they would be transferred to the genome of a host plant cell by *Agrobacterium* hosts containing the construct vectors along with a selectable marker gene. More specifically, the restriction fragment containing the entire cytosolic expression cassette encoding one of the proteins referenced above was cloned into an *Agrobacterium* plant transformation vector. Similarly, the restriction fragment containing the entire plastid targeted expression cassette was cloned into an *Agrobacterium* plant transformation vector. The vectors containing the TIC3668-type protein expression cassettes (i.e., untargeted cassette or targeted cassettes) are introduced into *Agrobacterium* by electroporation or by tri-parental mating.

Expression cassettes containing artificial genes encoding TIC4076, TIC4078, TIC4260, TIC4346, TIC4826, TIC4861, TIC4862, and TIC4863, each with and without sequences encoding the N terminal 23 amino acids present in the native *B. laterosperous* open reading frame (amino acids 1-23 as set forth in SEQ ID NO:2), are cloned into suitable vectors between the *Agrobacterium* border sequences so that they are transferred to the genome of a host cell and tested for expression and bioactivity of the encoded protein.

Example 7

Coleopteran Activity of TIC3668-Type Proteins in Plants

This Example illustrates inhibitory activity exhibited by TIC3668-like proteins against Coleoptera, such as corn rootworm larvae, when expressed in plants and provided as a diet to the respective insect pest.

R0 transgenic corn plants expressing TIC3668, mTIC3668, TIC3669, mTIC3669, TIC3670, and mTIC3670 proteins were produced using vectors containing the expression cassettes described in Example 5.

F1 transgenic corn plants were grown from seed produced by pollinating ears of non-transformed wild-type commercial germplasm plants with pollen from R0 transformants. After being transferred to soil in caged pots, F1 plants were infested with neonate corn rootworm insects and grown for 13 days under controlled conditions. Root damage ratings (RDR) were determined using the Oleson, et al. rating scale of 0-3, where 0 means no injury and 3 means three or more nodes are pruned to within 1.5 inches of the stalk (J. D. Oleson, Y-L. Park, T. M. Nowatzki, J. J. Tollefson, "Node-Injury Scale to Evaluate Root Injury by Corn Rootworms", *Journal of Economic Entomology,* 98(1):1-8, 2005). Insect mortality was assessed by counting the number of third instar larvae remaining at the end of the growth period.

In a first set of experiments, plants expressing the full-length TIC3668, TIC3669, and TIC3670 proteins were tested against WCR. Some of the events showed a statistical significant reduction in node injury compared to the negative control with an average root damage rating (RDR) value between 2 and 2.5, but no commercially significant activity was observed for the full-length proteins.

Figure 3:
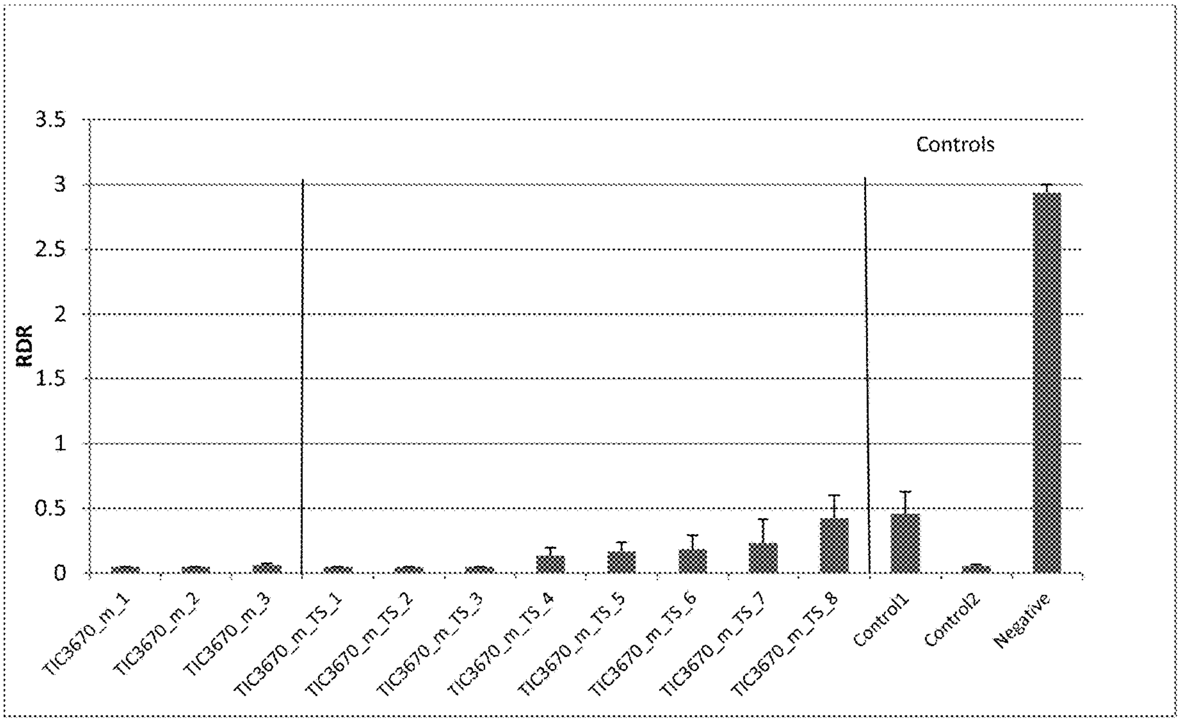
FIG. 3 illustrates in planta WCR inhibitory activity of an exemplary chloroplast targeted and non-targeted mature length TIC-3668-type protein.

In a second set of experiments, mature proteins mTIC3668 (SEQ ID NO:23), mTIC3669 (SEQ ID NO:24), and mTIC3670 (SEQ ID NO:25), with or without a chloroplast targeting peptide, were expressed in corn plants and tested against WCR. Significant WCR mortality was observed which each mature protein. Each plant expressing mTIC3668, mTIC3669, and mTIC3670, in the presence and absence of additional targeting sequences, showed a statistical significant reduction of node injury compared to the negative control. FIG. 2 depicts the average RDR values for several events for mTIC3668 and mTIC3669 proteins and FIG. 3 depicts the average RDR value for several events for mTIC3670 when expressed in F1 corn plants regardless of whether the protein was targeted to the chloroplast. "TS" in the event name of FIGS. 2 and 3 indicates the presence of a targeting sequence. Commercially significant activity was observed for many of these events expressing mature proteins mTIC3668, mTIC3669, and mTIC3670.

Surprisingly, removal of the membrane transiting segment (amino acids 1-23 as set forth in SEQ ID NO:2) from TIC3668-like proteins increased the efficacy against corn rootworm when expressed in corn plants. When expressed in plants, the mature length TIC3668-like proteins demonstrated higher levels of insecticidal activity against Coleopteran pests than the full-length proteins.

Example 8

Insecticidal Activity of TIC3668-Related Proteins, Expressed in Corn, Against Cry3Bb1 Resistant WCR This Example illustrates insecticidal activity exhibited by TIC3668-like proteins against a strain of Western Corn Rootworm (WCR) that has developed resistance to the Bt toxin Cry3Bb1. F1 transgenic corn plants expressing mTIC3668, mTIC3669 or mTIC3670, produced using methods as described in Example 7, were infested with 2000 WCR eggs of the Hopkinton strain per plant.

The Hopkinton strain of Western Corn Rootworm (*Diabrotica virgifera virgifera* LeConte) is a non-diapausing strain with field-evolved resistance to Cry3Bb1 expressed in corn plants. The strain originated from adult WCR samples obtained from fields that had been planted to Cry3Bb1 corn for seven consecutive years. The population was back-crossed with a non-diapausing WCR strain three times and selected for Cry3Bb1 resistance three times (Gassmann, et al. (2011) PLoS ONE 6(7): e22629; Gassmann, et al. (2012) GM Crops Food 3(3): 235-244). The colony was obtained from the laboratory of Dr. Aaron Gassman at Iowa State University, and is maintained by the Monsanto Biotech Entomology group in Chesterfield, Mo.

Following infestation, the WCR-Hopkinton strain eggs hatched within 48 hours and the neonates began feeding on the roots. After 24 days, the roots were removed from the soil and corn root damage was evaluated as described in Example 7, using the 0-3 scale. As shown in Table 9, the plants expressing mTIC3668, mTIC3669 and mTIC3670 were highly effective at protecting corn roots from damage in the presence of Hopkinton strain WCR neonates compared to control plants, thus overcoming the WCR resistance to the Cry3Bb1 toxin.

TABLE 9

Average RDR in Transgenic Corn Plants Infested with Cry3Bb1 Resistant WCR

| Toxin | N | Average RDR (0-3) | Standard Error |
|---|---|---|---|
| mTIC3668 | 18 | 0.06 | 0.004 |
| mTIC3669 | 15 | 0.05 | 1.82e−10 |
| mTIC3670 | 14 | 0.05 | 1.95e−10 |
| Negative Control | 6 | 2.14 | 0.24 |

N: number of plants evaluated

Example 9

Insecticidal Activity of TIC3668-Related Proteins, Expressed in Corn, Against Natural Infestation of WCR in Field Test Sites This Example illustrates reduced root damage effectiveness exhibited by transgenic corn plants expressing TIC3668-like proteins against natural WCR infestations in Midwestern U.S. farm fields.

F1 transgenic corn plants expressing mTIC3668, mTIC3669 or mTIC3670, produced using methods as described in Example 7, were planted at five locations in Midwestern U.S. during late April to early May. Trials at these locations relied on existing natural infestations for corn rootworm pressure. Root digging, for damage assessment, was completed by the end of July. Rootworm damage was determined according to the node-injury scale, as described in Example 7.

Results from the root dig trials indicated that under practical conditions for farming in an open field, plants expressing mTIC3668, mTIC3669 and mTIC3670 were highly effective at protecting corn roots from damage in the presence of natural corn rootworm pressure. Table 10 shows the number of plants evaluated (N), the mean RDR and standard error for test plants when locations are combined.

TABLE 10

Mean RDR in Transgenic Corn Plants Tested in Farm Field with Natural WCR Infestation

| Toxin | N | Mean RDR (0-3) | Standard Error |
|---|---|---|---|
| mTIC3668 | 755 | 0.144 | 0.009 |
| mTIC3669 | 1108 | 0.159 | 0.008 |
| mTIC3670 | 1311 | 0.120 | 0.007 |
| Negative Control | 362 | 1.426 | 0.047 |

Example 10

Lepidopteran Activity of TIC3668-Related Protein Toxin Class

This Example illustrates inhibitory activity exhibited by TIC3668-like proteins against Lepidoptera. Protein preparations, as described in Example 1, for the full-length proteins of TIC3668, TIC3669 TIC3670, TIC4076, and TIC4078 were submitted for insect diet-overlay bioassays against Black Cutworms (BCW, *Agrotis ipsilon*), Western Bean Cutworm (WBC, *Striacosta albicosta*), Corn Earworms (CEW, *Helicoverpa zea*), European Corn Borers (ECB, *Ostrinia nubilalis*), Sugarcane Borer (SCB, *Diatraea* saccharalis), Southwestern Corn Borer (SWC, *Diatraea grandiosella*), cabbage looper (CLW, *Trichoplusia ni*, soybean looper (SBL, *Chrysodeixis* includes), and Fall Armyworm (FAW, *Spodoptera frugiperda*). Protocols and methods of preparing and performing inhibitory protein bioassays are known in the art.

Activity against certain Lepidopteran insect pests was observed for certain TIC3668-type proteins as demonstrated in Table 11.

TABLE 11

Observed Stunting against Lepidopteran Insect Pests of Exemplary Proteins.

| Toxin | ECB | SWC | BCW | FAW | CEW | SBL |
|---|---|---|---|---|---|---|
| TIC3668 | ++ | + | NT | − | − | − |
| TIC3669 | + | + | NT | − | − | − |
| TIC3670 | ++ | ++ | NT | − | − | + |
| TIC4076 | − | +++ | − | − | − | + |
| TIC4346 | + | + | NT | + | + | + |
| TIC4078 | NT | NT | NT | − | − | + |
| TIC4260, TIC4826 TIC4861. | NT | NT | NT | NT | NT | NT |

+ = Stunting observed
++ = Stunting and mortality
− = Mortality not observed
NT = Not tested

Example 11

Lepidopteran Activity of TIC3668-Type Proteins in Plants

This example illustrates the inhibitory activity of the TIC3668-type proteins to ECB, SWC, BCW, FAW, CEW, SBL when expressed in plants and provided as a diet to respective insect pest.

Bioassays against Lepidopteran pests using plant leaf disks were performed similarly as described in U.S. Pat. No. 8,344,207 on TIC3668, TIC3669, and TIC3670 expressing R0 corn plants. The leaf damage rating (LDR) was assigned a rating score based upon the percent of the leaf disc devoured by the insect on a scale from 0 (0% eaten) to 11 (greater than 50%) eaten. Rating score steps increase incrementally by 5%. R0 plants which do not contain insecticidal proteins served as negative controls. The cytosolic expression of the full-length TIC3668-type protein reduced feeding damage against CEW, FAW and SWC relative to the untransformed control. Cytosolic expression of the TIC3670 protein reduced feeding damage against SWC relative to the untransformed control.

Example 12

Creation of the Collage Protein TIC4260

This Example teaches the creation of a novel gene sequence based on the family members of TIC3668. The amino acid variation from five of the native TIC3668-type proteins was combined to create a novel collage protein, TIC4260 (SEQ ID NO:12), that exhibits a different amino acid sequence diversity compared to the naturally occurring proteins. FIG. 1 depicts the alignment of five native TIC3668-type proteins with TIC4260. Positions of sequence diversity are highlighted in gray shading in this sequence alignment. An artificial polynucleotide sequence was constructed (SEQ ID NO: 11) that encodes the TIC4260 protein. The mature TIC4260 protein (mTIC4260, SEQ ID NO:28) is encoded by the polynucleotide sequence as set forth in SEQ ID NO:43.

Similar alignments of other TIC3668-type proteins can be made in order to create novel proteins exhibiting Lepidoptera and/or Coleoptera toxic activity. These novel proteins are expressed, purified and tested against Lepidopteran and Coleopteran inspects in diet bioassays. Expression cassettes for these novel proteins are created and transformed into plants to express these proteins to control Lepidopteran and Coleopteran pests of plants.

Example 13

Assay of Activity of Full-Length and Mature TIC3668-Type Proteins

This Example illustrates the bioactivity of additional TIC3668-type toxin proteins, TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 against at least one corn rootworm species. Known members of corn rootworm species are *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR) and a Brazilian Corn Rootworm complex (BCR) consisting of *Diabrotica viridula* and *Diabrotica speciosa*).

Coding sequences encoding full length and mature forms of TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 were expressed in *Bacillus thuringiensis* (Bt) and *Escherichia coli* (*E. coli*) and used in a diet bioassay against at least one corn rootworm species. The full length toxins TIC11239, TIC11243, TIC11256, TIC4544, TIC4545, TIC6871, TIC7429, TIC7497, TIC7511, TIC7513, TIC7518, TIC7524, TIC7526, TIC7528, and TIC7535 were expressed in Bt, while the mature toxins, mTIC11239, mTIC111243, mTIC11256, mTIC4544, mTIC4545, mTIC6871, mTIC7429, mTIC7497, mTIC7511, mTIC7513, mTIC7518, mTIC7524, mTIC7526, mTIC7528, and mTIC7535 were expressed in *E. coli*. Preparations of each toxin protein were added to an insect diet and presented to corn rootworm neonates. Mortality and stunting were evaluated by comparing the growth and development of the neonates on the diet and compared to untreated controls fed a diet lacking toxin. The bioactivity for each full length and mature protein is provided in Table 12 below, wherein "+" indicates activity (mortality and growth inhibition), "NA" indicates no activity was observed for the sample, and "NT" indicates not tested.

TABLE 12

Activity of TIC3668-type proteins against corn rootworm species.

| Full Length Toxin | | | Mature Toxin | | |
|---|---|---|---|---|---|
| Toxin | Protein SEQ ID NO: | Corn Rootworm | Toxin | Protein SEQ ID NO: | Corn Rootworm |
| TIC11239 | 74 | + | mTIC11239 | 104 | + |
| TIC11243 | 76 | NA | mTIC11243 | 106 | + |
| TIC11256 | 78 | + | mTIC11256 | 108 | + |
| TIC4544 | 80 | + | mTIC4544 | 110 | NT |
| TIC4545 | 82 | + | mTIC4545 | 112 | NT |
| TIC6871 | 84 | + | mTIC6871 | 114 | NT |
| TIC7429 | 86 | + | mTIC7429 | 116 | NT |
| TIC7497 | 88 | + | mTIC7497 | 118 | + |
| TIC7511 | 90 | + | mTIC7511 | 120 | + |
| TIC7513 | 92 | + | mTIC7513 | 122 | NT |
| TIC7518 | 94 | + | mTIC7518 | 124 | NT |
| TIC7524 | 96 | NA | mTIC7524 | 126 | + |
| TIC7526 | 98 | + | mTIC7526 | 128 | + |
| TIC7528 | 100 | + | mTIC7528 | 130 | + |
| TIC7535 | 102 | NA | mTIC7535 | 132 | + |

As can be seen in Table 12, the full length toxins, TIC11239, TIC11256, TIC4544, TIC4545, TIC6871, TIC7429, TIC7497, TIC7511, TIC7513, TIC7518, TIC7526, and TIC7528 demonstrated activity against at least one corn rootworm species when expressed in Bt. The mature toxins, mTIC11239, mTIC11243, mTIC11256, mTIC7497, mTIC7511, mTIC7524, mTIC7526, mTIC7528, and mTIC7535 also demonstrated activity against at least one corn rootworm species.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

It should be apparent to those skilled in the art that these different, improved sequence variations can be combined to create variants which are also within the scope of this invention.

All publications and published patent documents cited in the specification are incorporated herein by reference to the same extent as if each individual publication or patent application was specifically and individually indicated to be incorporated by reference.

What is claimed is:

1. A recombinant polynucleotide molecule encoding an insect inhibitory polypeptide, wherein the polypeptide comprises:

(a) the amino acid sequence of SEQ ID NO:74; or (b) an amino acid sequence comprising at least 99.3% identity to the amino acid sequence of SEQ ID NO:74, and wherein the recombinant polynucleotide molecule is operably linked to a heterologous promoter.

2. The recombinant polynucleotide molecule of claim 1 comprising:

(a) the nucleotide sequence of SEQ ID NO:73;

(b) a nucleotide sequence comprising at least 80% identity to the nucleotide sequence of SEQ ID NO:73; or (c) a nucleotide sequence that hybridizes under stringent conditions to the reverse complement of the nucleotide sequence from position 4-885 of the sequence of SEQ ID NO:73;

wherein said stringent conditions comprise hybridization from 4 to 12 hours in 50% formamide, 1 M NaCl, and 1% SDS at 37 C, and a wash in 0.1×SSC at 60 C-65 C.

3. An insect inhibitory recombinant polypeptide encoded by the recombinant polynucleotide molecule of claim 1.

4. The insect inhibitory recombinant polypeptide of claim 3, wherein said insect inhibitory recombinant polypeptide comprises an amino acid sequence comprising at least 99% identity to the amino acid sequence of SEQ ID NO:74.

5. The insect inhibitory recombinant polypeptide of claim 3, wherein said insect inhibitory recombinant polypeptide exhibits inhibitory activity against Western Corn Rootworm, Southern Corn Rootworm, Northern Corn Rootworm, Mexican Corn Rootworm, Brazilian Corn Rootworm, or Brazilian Corn Rootworm complex consisting of *Diabrotica viridula* and *Diabrotica speciosa.*

6. A host cell comprising the recombinant polynucleotide molecule of claim 1, wherein said host cell is selected from the group consisting of a bacterial host cell and a plant host cell.

7. An insect inhibitory composition comprising the recombinant polynucleotide molecule of claim 1.

8. The insect inhibitory composition of claim 7, further comprising a nucleotide sequence encoding at least one other pesticidal agent that is different from said insect inhibitory polypeptide.

9. The insect inhibitory composition of claim 8, wherein said at least one other pesticidal agent is selected from the group consisting of an insect inhibitory protein, an insect inhibitory dsRNA molecule, and an ancillary protein.

10. The insect inhibitory composition of claim 9, wherein said at least one other pesticidal agent exhibits activity against one or more pest species of the orders Lepidoptera, Coleoptera, or Hemiptera.

11. The insect inhibitory composition of claim 10, wherein said at least one other pesticidal agent is selected from the group consisting of a Cry1A, Cry1Ab, Cry1Ac, Cry1A.105, Cry1B, Cry1C, Cry1D, Cry1E, Cry1F, Cry1G, Cry1H, Cry1I, Cry1J, Cry1K, Cry1L, Cry2A, Cry2Ab, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, VIP3A, and VIP3B protein.

12. An insect inhibitory composition comprising the insect inhibitory recombinant polypeptide of claim 3 in an insect inhibitory effective amount.

13. A method of controlling a corn rootworm pest, said method comprising contacting said pest with an insect inhibitory amount of the insect inhibitory recombinant polypeptide of claim 3.

14. A seed comprising the recombinant polynucleotide molecule of claim 1.

15. A commodity product comprising the host cell of claim 6, said commodity product comprising a detectable amount of said recombinant polynucleotide or an insect inhibitory recombinant polypeptide encoded by said recombinant polynucleotide.

16. A method of producing seed comprising the recombinant polynucleotide molecule of claim 1, said method comprising:

(a) planting at least one seed comprising said recombinant polynucleotide molecule;

(b) growing plants from said seed; and (c) harvesting seed from said plants, wherein said harvested seed comprises said recombinant polynucleotide molecule.

17. A recombinant vector comprising the recombinant polynucleotide molecule of claim 1.

18. The recombinant vector of claim 17, wherein said vector is selected from the group consisting of a plasmid, a bacmid, a phagemid, and a cosmid.

19. A plant resistant to insect infestation, wherein the cells of said plant comprise the recombinant polynucleotide molecule of claim 1.

* * * * *